United States Patent [19]

Claussner et al.

[11] Patent Number: 5,149,696
[45] Date of Patent: Sep. 22, 1992

[54] 19→NOR→STEROIDS

[75] Inventors: André Claussner, Villemomble; Lucien Nedelec, Le Raincy; Daniel Philibert, La Varenne Saint Hilaire; Patrick Van De Velde, Paris, all of France

[73] Assignee: Roussel Uclaf, Paris, France

[21] Appl. No.: 484,424

[22] Filed: Feb. 23, 1990

[30] Foreign Application Priority Data

Feb. 24, 1989 [FR] France ................. 89 02384

[51] Int. Cl.$^5$ .................. C07J 1/00; C07J 5/00; A61K 31/565; A61K 31/57
[52] U.S. Cl. .................. 514/179; 514/182; 552/540; 552/548; 552/554; 552/558; 552/598; 552/610; 552/626; 552/646; 540/107; 540/108; 540/13
[58] Field of Search ........... 552/626, 540, 548, 554, 552/558, 598, 610, 626, 646; 514/182, 178, 179

[56] References Cited

U.S. PATENT DOCUMENTS

| | | | |
|---|---|---|---|
| 3,922,292 | 11/1975 | Torelli et al. | 552/517 |
| 4,447,424 | 5/1984 | Toutsch et al. | 552/615 |
| 4,540,686 | 9/1985 | Philibert et al. | 552/648 |
| 4,634,695 | 1/1987 | Torelli et al. | 514/178 |

OTHER PUBLICATIONS

Hadley, Endocrinology, (Englewood, N.J., Prentice Hall, 1984) p. 430.
Grant and Hack's Chemical Dictionary, 5th Ed. (1987), McGraw-Hill Book Co., New York, p. 313.

Primary Examiner—Mukund J. Shah
Assistant Examiner—Philip Datlow
Attorney, Agent, or Firm—Bierman and Muserlian

[57] ABSTRACT

Novel 19-nor-steroids of the formula

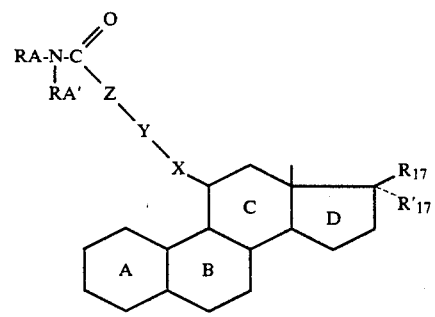

wherein the A and B rings have a structure selected from the group consisting of

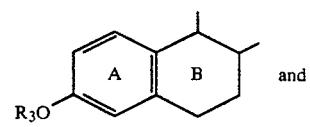 and

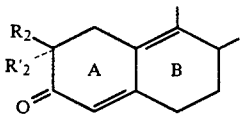

having hormonal properties and their preparation and intermediates.

11 Claims, No Drawings

19→NOR→STEROIDS

STATE OF THE ART

Related prior art are U.S. Pat. No. 4,477,445; No. 4,540,686 and No. 3,922,292 and French Patent No. 2,582,654.

OBJECTS OF THE INVENTION

It is an object of the invention to provide the novel compounds of formula I and a novel process and novel intermediates for their preparation.

It is another object of the invention to provide novel hormonal compositions and novel methods of inducing hormonal reactions in warm-blooded animals.

These and other objects and advantages of the invention will become obvious from the following detailed description.

THE INVENTION

The novel compounds of the invention are 19-nor-steroids of the formula

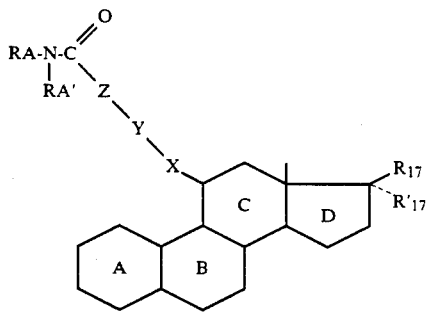

wherein the A and B rings have a structure selected from the group consisting of

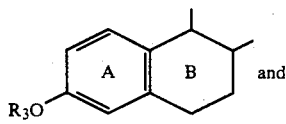

and

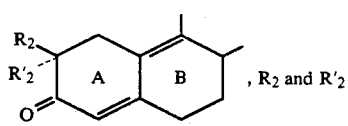

, $R_2$ and $R'_2$ are individually selected from the group consisting of hydrogen and alkyl of 1 to 4 carbon atoms, $R_3$ is selected from the group consisting of hydrogen, alkyl of 1 to 4 carbon atoms and acyl of an organic carboxylic acid of 1 to 7 carbon atoms, $R_{17}$ and $R_{17}'$ together form =O or $R_{17}$ is —OH or acyloxy and $R_{17}'$ is selected from the group consisting of hydrogen, alkyl of 1 to 8 carbon atoms and alkenyl and alkynyl of 2 to 8 carbon atoms, all optionally substituted, X is selected from the group consisting of —CH$_2$—, —CH$_2$O—, arylene and arylenoxy linked to the C ring through a carbon atom, Y is selected from the group consisting of a simple bond and saturated and unsaturated aliphatic of 1 to 18 carbon atoms optionally interrupted with at least one member of the group consisting of arylene, —O— and optionally oxidized —S— and optionally terminated with aryl, Z is a simple bond or —CH$_2$O— linked to Y by a carbon atom, $R_A$ and $R_A'$ being individually selected from the group consisting of hydrogen and alkyl of 1 to 8 carbon atoms optionally substituted with at least one member of the group consisting of aryl, alkylamino, dialkylamino, —OH, halogen and esterified carboxyl or $R_A$ and $R_A'$ taken together with nitrogen to which they are attached form a 5 to 6 ring heterocycle optionally containing at least one heteroatom selected from the group consisting of —S—, —O— and —N— optionally substituted with alkyl of 1 to 4 carbon atoms with the proviso 1) that both of $R_A$ and $R_A'$ are not hydrogen and 2) when Z and Y are both simple bonds, X is not —CH$_2$— or —CH$_2$O—.

Examples of $R_3$, $R_2$ and/or $R_2'$ as alkyl are methyl, ethyl, propyl, isopropyl, butyl, tert.-butyl and isobutyl, preferably methyl. Examples of $R_3$ as acyl are acetyl, propionyl, butyryl and benzoyl.

When $R_{17}$ is an acyloxy, it is a derivative of an aliphatic or cycloaliphatic carboxylic acid, saturated or unsaturated and especially alkanoic acids such as for example, acetic acid, propionic acid, butyric acid or isobutyric acid, valeric acid or undecylic acid, a hydroxyalkanoic acid such as hydroxyacetic acid; cycloalkylcarboxylic acids or cycloalkylalkanoic acids such as cyclopropylcarboxylic acid, cyclopentylcarboxylic acid or cyclohexyl carboxylic acid, cyclopentyl or cyclohexyl acetic acid or propionic acid, benzoic acid, salicylic acid or a phenylalkanoic acid such as phenylacetic acid or phenylpropionic acid, an amino acid such as diethylaminoacetic acid or aspartic acid or formic acid. It is preferably a derivative of acetic acid, propionic acid or butyric acid.

When $R_{17}'$ is alkyl, it is preferably methyl, ethyl, propyl, isopropyl, butyl, isobutyl, n-pentyl, n-hexyl, 2-methyl pentyl, 2,3-dimethyl butyl, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl and most preferably, methyl.

When $R_{17}'$ is alkenyl, it is preferably vinyl, propenyl, isopropenyl, allyl, 2-methylallyl, butenyl or isobutenyl and most preferably vinyl or propenyl. When $R_{17}'$ is alkynyl, it is preferably ethynyl, propynyl, propargyl, butynyl or isobutynyl and most preferably ethynyl or propynyl.

The expression optionally substituted applied to the alkyl, alkenyl or alkynyl includes at least one member of the group consisting of halogen, such as fluorine, chlorine, bromine or iodine, alkoxy such as methoxy, ethoxy, propoxy, isopropoxy, butoxy, alkylthio such as methylthio, ethylthio, propylthio, isopropylthio, butylthio, amino, alkylamino such as methylamino or ethylamino, dialkylamino such as dimethylamino, diethylamino or methyl ethylamino, each of the dialkylaminos being optionally in the oxidized form; aminoalkyl such as aminomethyl or aminoethyl, dialkylaminoalkyl such as dimethylaminomethyl or ethyl, dialkylaminoalkoxy such as dimethylaminoethoxy, optionally acylated hydroxyl, for example acetoxy or

in which n=2 to 5, such as acetyl, propionyl, butyryl, benzoyl, free or esterified carboxy and alkoxycarbonyl, for example methoxycarbonyl or ethoxycarbonyl, cyano, trifluoromethyl, aryl such as phenyl, furyl, thienyl or aralkyl such as benzyl, these being optionally substituted by alkyl such as methyl, ethyl, propyl, isopropyl, butyl, isobutyl, tert-butyl or by alkoxy, alkylthio, alkylamino or di-alkylamino indicated above.

When X is arylene, it is preferably phenylene and when X is arylenoxy, it is preferably phenylenoxy.

When Y is saturated or unsaturated linear or branched aliphatic chain, it can be methylene, ethylene, propylene, isopropylene, butylene, isobutylene, or tert-butylene, n-pentylene, n-hexylene, 2-methyl pentylene, 2,3-dimethyl butylene, n-heptylene, 2-methylhexylene, 2,2-dimethylpentylene, 3,3-dimethyl pentylene, 3-ethylpentylene, n-octylene, 2,2-dimethylhexylene, 3,3-dimethylhexylene, 3-methyl 3-ethylpentylene, nonylene, 2,4-dimethyl heptylene, n-decylene, n-undecylene, n-dodecylene, n-tridecylene, n-tetradecylene, n-pentadecylene, n-hexadecylene n-heptadecylene or n-octadecylene, preferably n-nonylene or n-decylene. Equally it can be one of the following, vinylene, isopropylene, allylene, 2-methylallylene or isobutenylene, and when the chain is interrupted or terminated by one or more arylenes, it is preferably phenylene, it being understood that terminated relates to anyone of the two extremities of Y.

When RA or RA' is alkyl, it can be methyl, ethyl, propyl, isopropyl, butyl, isobutyl or tert.-butyl, n-pentyl, n-hexyl, 2-methyl pentyl, 2,3-dimetyl butyl, n-heptyl, 2-methylhexyl, 2,2-dimethylpentyl, 3,3-dimethylpentyl, 3-ethylpentyl, n-octyle, 2,2-dimethylhexyl, 3,3-dimethylhexyl, 3-methyl-3-ethylpentyl.

The aforementioned radicals can be substituted by one or more aryl such as phenyl, furyl, thienyl, preferably phenyl; by one of or more alkylamino or dialkylamino such as dimethylamino or by one or more esterified carboxyl such as by methoxycarbonyl or an ethoxycarbonyl, by one or more halogen atoms for example, fluorine, chlorine or bromine. 2,2,3,3,4,4,4-heptafluorobutyl or 2-chloro-2-methylpropyl can notably be cited.

When RA and RA' form with the nitrogen atom to which they are linked a heterocycle with 5 to 6 links, it is a saturated heterocycle, preferably pyrrolidine or piperidine optionally substituted by alkyl such as methyl, ethyl, propyl or isopropyl, preferably methyl or ethyl or an unsaturated heterocycle, preferably pyrrole or pyridine optionally substituted by alkyl such as methyl, optionally containing another heteroatom, preferably morpholine, piperazine or pyrimidine, optionally substituted by alkyl, preferably methyl or ethyl.

The preferred compounds of formula I of the invention are those wherein the A and B rings are

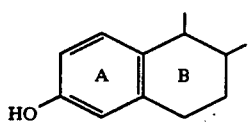

and those wherein A and B are

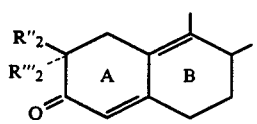

in which $R_2''$ or $R_2'''$ are hydrogen or methyl, preferably hydrogen, those in which Z is a simple bond and those in which $R_{17}$ is hydroxyl, those in which $R_{17}'$ is hydrogen, ethynyl or propynyl, those in which X is methylene and Y is saturated linear chain of 5 to 10 carbon atoms optionally interrupted by an oxygen atom and those in which X is phenylene and Y is a saturated linear chain of 3 to 10 carbon atoms optionally interrupted by an oxygen atom and those in which X is phenylenoxy and Y is saturated linear chain of 3 to 10 carbon atoms optionally substituted by an oxygen or sulfur atom.

Among the preferred compounds of the invention are those in which either RA and RA' are both methyl or RA is hydrogen or methyl and RA' is butyl, or RA is methyl and RA' is isopropyl, dimethylaminoethyl, benzyl or heptafluorobutyl or RA and RA' form together a piperazine optionally N-substituted or a pyrrolidine.

Among the specific preferred compounds of the invention are 11β-N-(2-dimethylaminoethyl)-17β-hydroxy-N-methyl-3-oxo-$\Delta^{4,9}$-estradien-undecanamide, N-butyl-4-(3,17β-dihydroxy-$\Delta^{1,3,5(10)}$-estratrien-11β-yl)-N-methyl-benzene octanamide, 3,17β-dihydroxy-N-methyl-N-isopropyl-11β-$\Delta^{1,3,5(10)}$-estratrien-undecanamide, N-butyl-3,17β-dihydroxy-N-methyl-19-nor-11β-(17α-$\Delta^{1,3,5(10)}$-pregnatrien-20-yn)-undecanamide, 3,17β-dihydroxy-N-methyl-N-isopropyl-19-nor-11β-17α-$\Delta^{1,3,5(10)}$-pregnatrien-20-yn)-undecanamide, [[8-(3,17β-dihydroxy-$\Delta^{1,3,5(10)}$-estratrien-11β-yl)-octyl]-oxy]-N-methyl-N-isopropyl-acetamide, N-butyl-8-[4-(3,17β-dihydroxy $\Delta^{1,3,5(10)}$-estratrien-11β-yl)-phenoxy-N-methyl octanamide, N-butyl-[5-[4-(3,17β-dihydroxy-$\Delta^{1,3,5(10)}$-estratrien-11β-yl)-phenoxy]-pentoxy]-N-methyl acetamide, 2-[(7-[4-(3,17β-dihydroxy-$\Delta^{1,3,5(10)}$-estratrien-11β-yl)-phenyl]-6-heptyl]-oxy]-N-butyl-N-methyl acetamide, 3,17β-dihydroxy-N-(2,2,3,3,4,4,4-heptafluorobutyl)-N-methyl-$\Delta^{1,3,5(10)}$-estratrien-11β-yl undecanamide and 8-[4-(3,17β-dihydroxy-$\Delta^{1,3,5(10)}$-estratrien-11β-yl)-phenyl]-N-butyl-N-methyl octynamide.

The novel process of the invention for the preparation of the compounds of formula I comprises reacting a compound of the formula

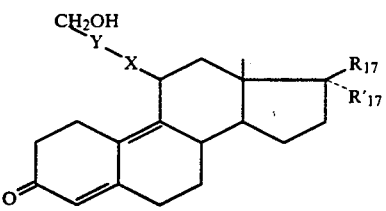

wherein X, Y, $R_{17}$ and $R_{17}'$ have the above definitions with $R_{17}$ being other than —OH either with an oxidizing agent to obtain a product of the formula

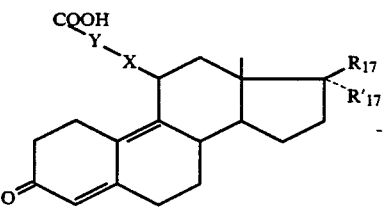

reacting the latter with an agent permitting the activation of the carboxylic function, then with a compound of the formula

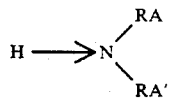

wherein RA and RA' have the above definitions to obtain the product of formula Ia corresponding to the compound of formula I in which Z is a simple bond and the rings A and B are

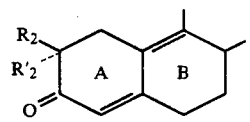

wherein $R_2$ and $R_2'$ are hydrogen or with a compound capable of introducing

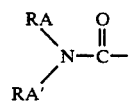

to obtain a compound of formula I'a which is a compound of formula I wherein Z is —CH$_2$O— and A and B rings have the definition of formula $I_a$, the compounds of formulae $I_a$ or $I_a'$ optionally being reacted with a reducing agent when $R_{17}$ and $R_{17}'$ together form =O, then if appropriate, reacting the 17-hydroxylated compound with an acylation agent, or with a saponification agent when $R_{17}$ is an acyloxy, to obtain a product of formula Ia or $I_a'$ in which $R_{17}$ has the above meaning, then if desired, reacting one of the products of formula Ia or $I_a'$, either to obtain an alkylation at position 2, when at least one of $R_2$ and $R_2'$ is hydrogen, or reacts with an aromatization agent of ring A, then to a saponification agent to obtain the products of formula Ib corresponding to products of formula Ia and the products of formula $I_b'$ corresponding to the products of formula $I_a'$ in which the rings A and B are

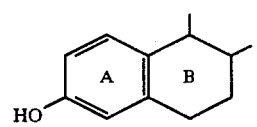

optionally reacting the products of formula Ib and Ib' to an alkylation or acylation reaction of the 3-hydroxy, then, if desired, either, when $R_{17}$ and $R_{17}'$ together form =O to a reducing agent or to a metallic complex of the formula

  M-$R_{17}'$      V wherein M is a metallic ion and $R_{17}'$ has the above definition other than hydrogen, or when $R_{17}$ is a hydroxy reacting with an acylation agent selective at position 17, then, if desired, with one of the products of formula I obtained above, or when RA or RA' is hydrogen with an appropriate alkylation agent.

The compounds of formula I are 19-nor steroids having: either a chain at the 11β-position containing a substituted amide function which compounds are then chosen from among the compounds of formulae Ia and Ib, or a chain at the 11β-position containing a substituted carbamate function which compounds are chosen from among the compounds of formulae Ia' and Ib'.

The compounds of formula $I_a'$ are obtained by reacting a compound of formula II either with an activator of the hydroxyl such as phosgene, then with a primary or secondary amine of formula IV in a neutral solvent such as methylene chloride or tetrahydrofuran in the presence of a base such as potassium carbonate or methylamine, or with an isocyanate of the formula RA-N=C=O to obtain a product in which RA' is hydrogen.

The compounds of formula Ia are obtained by reacting a compound of formula III activated, for example in the form of the mixed anhydride with an agent such as chloroformate, for example, isobutyl chloroformate, in the presence of a base such as a tertiary amine like N-methylmorpholine in an annydrous solvent such as a chlorinated solvent, i.e., methylene chloride with the amine of formula IV.

The product of formula III is obtained by using an oxidizing agent such as, for example, the mixture CrO$_3$-sulfuric acid in a neutral solvent such as acetone.

In a preferred embodiment of the invention:

The compounds of formula II contain a 11β chain terminated by an alcohol function selected from the following Table:

| X | Y | —CH$_2$OH |
|---|---|---|
| ![phenyl] | —(CH$_2$)$_7$ | —CH$_2$OH |
| " | —C≡C—(CH$_2$)$_5$ | —CH$_2$OH |
| " | —C≡C—(CH$_2$)$_5$—O—CH$_2$ | —CH$_2$OH |
| ![phenyl-O] | —(CH$_2$)$_5$—O—CH$_2$ | —CH$_2$OH |
| " | —(CH$_2$)$_7$ | —CH$_2$OH |
| —CH$_2$ | —(CH$_2$)$_9$ | —CH$_2$OH |
| " | —(CH$_2$)$_7$—O—CH$_2$ | —CH$_2$OH | as illustrated in the examples hereafter.

The compounds of formula III contain a 11β-chain terminated by a carboxylic acid corresponding to the oxidation product of a chain chosen from among the 11β-chains terminated by one of the alcohol functions cited above.

The compound of formula IV is chosen from the following amines: butylamine, methylbutylamine, dimethylamine, methylisopropylamine, methyldimethylaminoethylamine, methylbenzylamine, pyrrolidine or N-methylpiperazine which are known products.

When the compound of formulae Ia or $I_a'$ has a 17β-ketone, the corresponding 17β-hydroxyl steroid is obtained by the action of a reducing agent such as sodium borohydride in a neutral solvent such as methanol or triterbutoxylithium aluminium hydride in tetrahydrofuran.

When the compound of formulae Ia or $I_a'$ has a 17β-hydroxy, the corresponding 17-acyloxylated steroid is obtained by the action of an acylation agent, for example an acetylation agent such as acetic anhydride in pyridine, optionally in the presence of 4-dimethylamino-pyridine.

When the compounds of formulae Ia or I$_a$' have 17β-acyloxy, the corresponding 17β-ol steroid is obtained with a saponification agent such as potassium hydroxide in an alcoholic medium.

When the compounds of formulae Ia or I$_a$' has one or two hydrogen atoms at position 2 or/and 2', the corresponding mono or dialkylated steroid at position 2 and 2' is obtained by the action of an alkylation agent, preferably a methylation agent such as methyl iodide.

The compounds of formulae Ib and I$_b$' which are steroid derivatives of estradiol having a 11β-chain containing a substituted amide function or a substituted carbamate function are obtained starting with the compounds of formulae Ia and I$_a$' respectively, by the action of an aromatization agent such as palladium hydroxide on magnesia in methanol or a mixture of acetyl bromide and acetic anhydride at a temperature not exceeding that of ambient followed by a saponification reaction using, for example, potassium hydroxide in methanol, sodium bicarbonate or methanol in the presence of hydrochloric acid.

When the compounds of formulae Ib or I$_b$' have a 3-hydroxy, the corresponding alkylated steroids is obtained with an alkylation reagent such as alkyl iodide or an alkyl sulfate, for example, methyl sulfate or the corresponding acylated steroid by the action, of a standard acylation reagent such as an acyl halide like acetyl chloride.

When the compounds of formula Ib or I$_b$' have a 17 ketone, the corresponding 17β-hydroxyl steroids are obtained under the conditions described above for Ia or I$_a$', for example by the action of a reducing agent such as sodium borohydride in a neutral solvent such as methanol and the corresponding compound of formulae Ib or I$_b$' wherein R$_{17}$' is alkyl, alkenyl or alkynyl optionally substituted are obtained by using as a complex, for example, a lithium complex according to the process of EP Patent Application 57,115.

When the compounds of formula Ib or I$_b$' have a 17β-hydroxy, the acyloxyl steroids can be obtained by the action of a selective acylation agent such as acetic anhydride in pyridine.

When RA or RA' is hydrogen, the corresponding alkylated product may be obtained by the action of an alkyl halide, for example methyl or ethyl iodide, methyl or ethyl bromide in a solvent such as tetrahydrofuran. It is well understood that if R$_{17}$' contains an alkyl, alkenyl or alkynyl substituted by a reactive function, this can be provisionally protected by the usual methods.

The novel process of the invention for the preparation of compounds of formula I' wherein X is arylene and Y is aliphatic optionally linked to arylene by a double or triple bond and having at least 3 carbon atoms or linked to arylene through an oxygen atom comprises reacting a compound of the formula

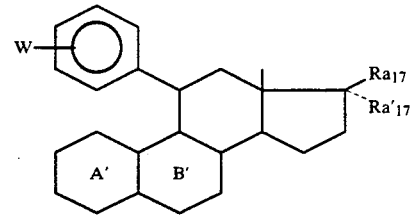

wherein W is either —OH or —C≡CH, the rings A' and B', Ra$_{17}$ and Ra$_{17}$' having the same meanings as indicated above for rings A and B, R$_{17}$ and R$_{17}$' and in which the 3- and 17-reactive functions are optionally protected or, when W is —C≡CH reacted with a halogenation agent of the formula

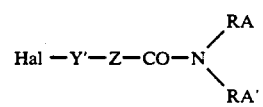

wherein Hal is halogen, Z, RA, and RA' have the above definitions and Y' is aliphatic Y having 2 carbon atoms missing, in the presence of a strong base, and optionally to the action of a deprotection agent to obtain a product of the formula

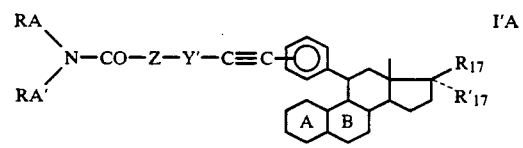

which optionally is reacted with a partial or total reducing agent of the triple bond to obtain a product of the formula

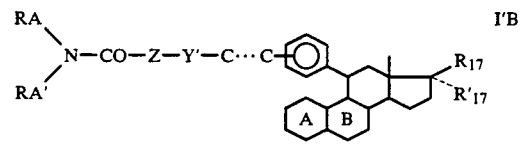

or, in the case where W is -OH to the action of a halogenated derivative of the formula

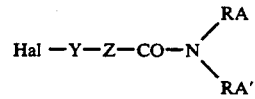

in which Hal, Y, Z, RA and RA' have the above definitions in the presence of an alkaline agent, and optionally reacting with a deprotection agent to obtain a product of the formula

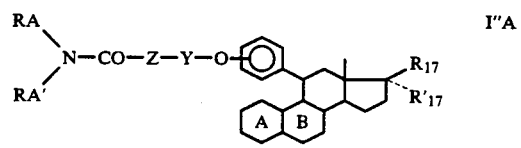

which optionally, when Y is an unsaturated aliphatic is reacted with a partial or total reducing agent, and the products of formula $I_A'$, $I_B'$ or $I_A''$ may be subjected to any one of the reactions indicated above for Ia, Ia', Ib and Ib'

In a preferred process of the invention, the optional protection groups of the 3- or 17-hydroxyl are selected from the standard groups such as tetrahydropyranyl and tert.-butyl and the halogen of Hal may be bromine, chlorine or idodine. The strong base used is, for example, butyllithium or sodium hydride and the alkaline agent used is an alkali metal hydroxide such as sodium hydroxide. The deblocking of the protected functions may be effected using of a standard hydrolysis agent such as hydrochloric acid and the optional reduction of the triple bond is effected either using hydrogen in the presence of palladium on activated charcoal, barium sulfate and optionally a base such as pyridine or quinoline in the case of a partial reduction. Palladium hydroxide is used alone in the case of a total reduction. In the compounds of formula X used initially, W is in the para position.

In a variation of the processes, the products of formula I wherein Z is a simple bond and Y is a linear aliphatic terminated by vinylene before the amide function, a compound of the formula

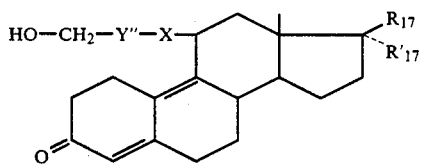

II' corresponding to the product of formula II in which Y''' is the aliphatic chain Y containing 2 carbon atoms missing, is reacted with an oxidation agent to obtain the corresponding aldehyde which is reacted with a phosphorane of the formula

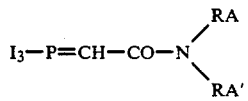

The products of formula I in which Y is a branched aliphatic chain can be prepared by alkylation of the products of formula I in which Y is a linear aliphatic chain after having, if appropriate, blocked the 3- and/or 17- reactive functions. The alkylation is effected by using an alkyl halide such as methyl iodide in the presence of lithium diisopropylamide. The products of formula III can be prepared by alkaline hydrolysis of the corresponding products containing at 11β position a a —X—Y—CN chain products obtained starting with products of formula II' as defined above in which one protects the hydroxyl functions, then is reacted with a halogenation agent such as an alkali metal halide, for example, sodium iodide and then an alkali metal cyanide such as potassium cyanide.

The novel hormonal compositions of the invention are comprised of an hormonally effective amount of at least one compound of formula I and an inert pharmaceutical carrier or excipient. The compositions may be in the form of tablets, dragees, capsules, granules, suppositories, pessaries, ointment, creams, gels, microspheres, implants, patches and injectable solutions or suspensions.

Examples of suitable excipients are talc, arabic gum, lactose, starch, magnesium stearate, cocoa butter, aqueous or non-aqueous vehicles, fatty substances of animal or vegetable origin, paraffin derivatives, glycols, various wetting agents, dispersants and emulsifiers and preservatives.

The compositions containing compounds of formula I present interesting pharmacological properties. The study of products on the hormonal receptors has brought to the fore that the compounds of formulae Ia and Ia' possess glucocoticoid or antiglucocorticoid, progrestomimetic or antiprogestomimetic, androgen or antiandrogen, antimineralocorticoid, estrogen or antiestrogen activity and the compounds of formulae Ib and I'b possess particularly a remarkable anti-estrogen activity and anti-proliferative properties as shown by the results of tests given intra.

These properties make the compositions containing compounds of formula Ia and I'a useful for combatting the side effects of glucocorticoids and permit the combatting of disorders due to a hypersecretion of glucocorticoids and notably the combatting of aging in general and more particularly the combatting of hypertension, atherosclerosis, osteoporosis, diabetes, obesity as well as the depression of immunity and insomnia. These compositions are equally of interest in the treatment of certain hormonal-dependent tumors.

The compositions containing compounds of formulae Ia and I'a which possess antiprogestomimetic properties can be used for the preparation of original contraceptives or as abortion agents and are useful for inducing (menstrual) periods in women and more generally in warm-blooded female animals. The compositions are administered during the periods where progesterone plays an essential physiological role, i.e., during the luteal phase of the cycle, at the moment of nidation (or implanation of the embryo) and during pregnancy. One method of contraception of the invention consists of administering to the woman at least one of the products of formula Ia or Ia' over 1 to 5 days, preferably at the end of the cycle. This product is then preferably administered orally or in vagino but it can also be administered parenterally and endonasally.

The compositions containing the compounds of formulae Ia and Ia' possessing anti-progestomimetic properties are also useful against hormone irregularities and, are of interest in the treatment of hormono-dependent tumors. Their actions on hypophysial secretions make the products usable in the menopause and these compositions can be used in the synchronization of estrus in farm animals, particularly cattle and sheep and for controlling the fertility of pets such as dogs or cats. Equally the compositions containing compounds of formulae Ia and Ia' can have progestomimetic properties and can be used in the treatment of amenorrhea, dysmenorrhea and luteal insufficiencies.

The compositions of compounds of formulae Ia and Ia' which possess anti-androgenic properties can be used in the treatment of hypertrophia and cancer of the prostate, hyperandrogenia, anemia, hirsutism and acne. Equally they can be used for male contraceptives.

The compositions of compounds of formulae Ia and Ia' which possess estrogenic properties make them useful in the treatment of disorders linked to a hypofolliculinia for example amenorrhea, dysmenorrhea, repeated miscarriages, premenstrual troubles as well as in the treatment of the menopause and of osteoporosis.

The anti-estrogen and anti-proliferation properties of compositions containing the compounds of formulae Ib and Ib' make them useful in the treatment of mammary carcinomas and their metastases and in the treatment of benign tumors of the breast.

Among the preferred compositions of the invention are those containing the compounds of Examples 8, 16, 19, 21, 35, 37, 43, 46, 55, 71 and 75.

The novel method of inducing hormonal activity in warm-blooded animals, including humans, comprises administering to warm-blooded animals an hormonally effective amount of at least one compound of formula I. The compounds may be administered orally, rectally or parenterally and the usual daily dose is 0.013 to 1.33 mg/kg depending upon the method of administration, the condition being treated and the specific compound being administered.

The compounds of formulae II and III are novel intermediates and an object of the invention.

The compounds of formula II may be prepared by reacting a magnesium derivative of a halogenated alcohol of the formula

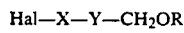

Hal—X—Y—CH$_2$OR    VI wherein X and Y have the above definitions, Hal is a halogen and R is hydrogen or an alcohol protecting groups such as

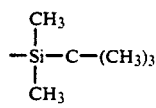

in the presence of a copper salt with a compound of the formula

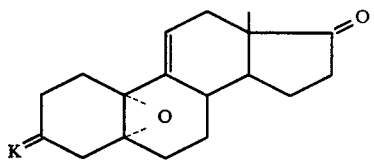

VII wherein K is a ketone protector group such as a cyclic ketal to obtain a compound of the formula

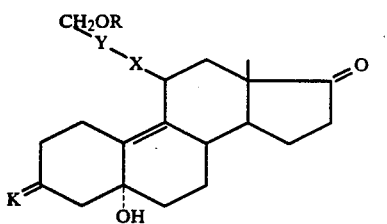

VIII optionally reacting the latter with a lithium derivative of a compound of the formula

H—R$_{17}$'    IX wherein R$_{17}$' has the above definition other than hydrogen or with a reducing agent, then optionally with an acylation agent and then to a dehydration and hydrolysis agent capable of liberating the 3-keto-Δ$^4$ function and the alcohol function to obtain the compound of formula II.

The products of formula VII are known products and their preparation is described, for example, in EP Patent No. 0,057,115. The products of formula X are described notably in European Patent Application No. EP 0,245,170 and specific examples of the preparation of products of formula X are described hereinafter in the examples. Examples of the preparation of products of formulae XI and XII are in the experimental part.

Among the preferred new products of formula II of the invention are 17β-acetyloxy-11β-[(8-hydroxyoctyl)phenyl]-Δ$^{4,9}$-estradien-3-one, 11β-(12-hydroxydodecyl)-Δ$^{4,9}$-estradiene-3,17-dione and 11β-(8-hydroxyoctyl)-Δ$^{4,9}$-estradien-3,17-dione.

Among the preferred products of formula III of the invention are 17β-acetyloxy-3-oxo-11β-Δ$^{4,9}$-estradiene-undecanoic acid, 3,17-dioxo-11β-Δ$^{4,9}$-estradiene undecanoic acid and 17β-hydroxy-3-oxo-17α-(1-propynyl)-11β-Δ$^{4,9}$-estradiene undecanoic acid.

The following products are products able to be obtained within the scope of the present invention:

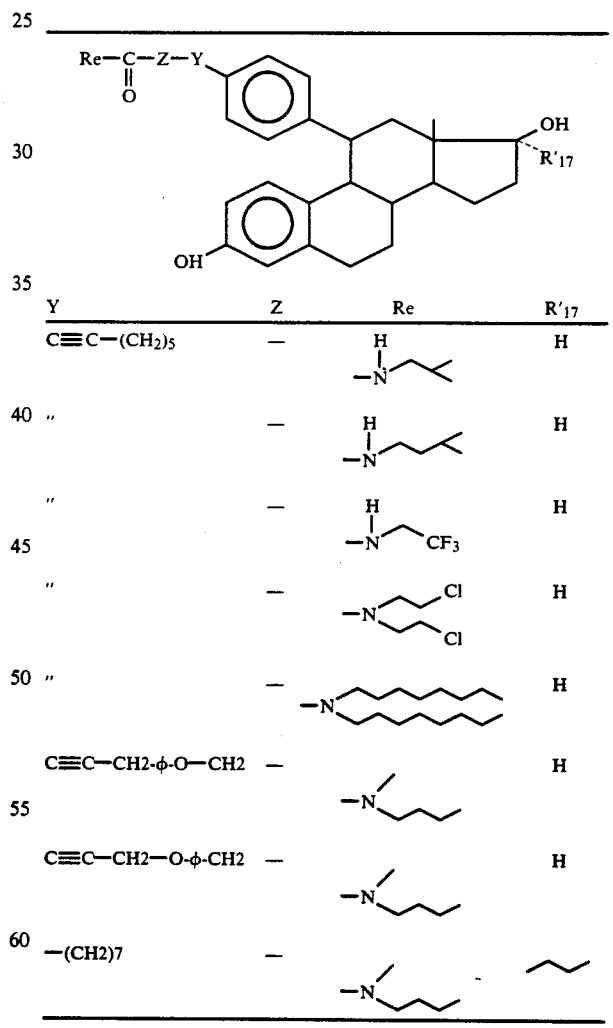

In the following examples there are described several preferred embodiments to illustrate the invention. However, it should be understood that the invention is not intended to be limited to the specific embodiments.

PREPARATION 1

17β-acetyloxy-11β-[4-(2-hydroxymethyl)-phenyl]-Δ$^{4,9}$-estradiene-3-one

Step A (5α,11β)-3-(1,2-ethanediyl cyclic acetal) of 5α-hydroxy-11β-[4-[2-[[(1,1-dimethylethyl)-dimethylsilyl]-oxy]-methyl]-phenyl]-Δ$^9$-estrene-3,17-dione Preparation of the Magnesium Reagent To a suspension of 1.4 g of magnesium turnings in 20 ml of tetrahydrofuran, 19.9 g of the brominated derivative obtained from preparation 9 in solution in 60 ml of tetrahydrofuran were added dropwise followed by stirring for 1 hour at 50° C. to obtain a solution with a titer=0.85 mole/liter.

Condensation

For 10 minutes at ambient temperature, a solution of 4.5 g of 3-(1,2-ethanediyl cyclic acetal) of 5α,10α-epoxy-Δ$^{9,11}$ estrene-3,17-dione [EP 0,057,115 (Example 7)] in 45 ml of tetrahydrofuran and 0.4 g of cupric chloride was stirred and over a period of 20 minutes, 50 ml of the magnesium reagent above were added without exceeding 27° C. After 90 minutes of stirring, the mixture was poured into an ice-cooled solution of ammonium chloride. The aqueous phase was extracted once with ethyl acetate and 3 times with methylene chloride to obtain 15.423 g of a product which was chromatographed over silica (eluant: cyclohexane-ethyl acetate (7-3)) to obtain 6.29 g of the desired product.

| IR Spectrum: (CHCl$_3$) | |
|---|---|
| OH at 5 | 3508 cm$^{-1}$ |
| C=O | 1733 cm$^{-1}$ |
| Aromatic | 1510 cm$^{-1}$ |
| O—Si probable | |

Step B 3-(1,2-ethanediyl cyclic acetal) of 5α,17β-dihydroxy-11β-[4-2-[[(1,1-dimethylethyl)-dimethylsilyl]-oxy]-methyl]-phenyl]-Δ$^9$-estren-3-one To a solution of 6.15 g of the product of Step A in 100 ml of methanol, 6 g of sodium boron hydride were added over 15 minutes and the mixture was stirred for two hours and poured into 500 ml of water and extracted with methylene chloride. The organic phase was evaporated to dryness to obtain 6.17 g of the desired product which was used as such in the following step.

| IR Spectrum: (CHCl$_3$) | |
|---|---|
| OH at 17 | 3611 cm$^{-1}$ |
| OH at 5 | 3508 cm$^{-1}$ |
| Aromatic | 1509 cm$^{-1}$ |
| O—Si probable | |

Step C

17β-acetyloxy 11β-[4-(2-methyl)-phenyl]-Δ$^{4,9}$-estradien-3-one a) Acetylation To a solution of 6.1 g of the product of Step B in 52 ml of pyridine and 1.15 g of 4-dimethylamino-pyridine, 5.2 ml of acetic anhydride were added and the mixture was stirred for 20 minutes and poured into 200 ml of an ice-cooled solution of sodium bicarbonate. The mixture was stirred for 10 minutes and extracted with methylene chloride. The organic phase was evaporated to dryness to obtain 6.828 g of the expected amorphous product.

b) Hydrolysis

The said product was taken up in 40 ml of 2N hydrochloric acid and 50 ml of ethanol and was stirred for 1 hour at ambient temperature and concentrated to half-volume under reduced pressure. The mixture was diluted with 100 ml of water, and extracted with methylene chloride. The organic phase was evaporated to dryness under reduced pressure and the residue was chromatographed over silica (eluant: cyclohexane-ethyl acetate (1-1)) to obtain 3.39 g of the desired product.

| IR Spectrum: CHCl$_3$ (on Nicolet) | |
|---|---|
| OH | 3618 cm$^{-1}$ |
| C=O | 1728 cm$^{-1}$ OAc |
| Dienone | 1656 |
| | 1602 |
| Aromatic | 1509 cm$^{-1}$ |

PREPARATION 2

3,17-dioxo-11β-Δ$^{4,9}$-estradiene-pentanoic acid

Step A 3-(1,2-ethanediyl cyclic acetal) of 11β-(5-hydroxy-pentyl)-Δ$^9$-estrene-5α-ol-3,17-dione Preparation of the Magnesium Reagent of 1-Chloro-5-Pentanol To a solution of 24.6 ml of 1-chloro-5-propanol in 246 ml of tetrahydrofuran, 300 ml of a 0.67M/liter solution of the magnesium reagent of 2-chloropropane in tetrahydrofuran was added over 20 minutes at −20° C. and the mixture was stirred for 20 minutes at −20° C. 7.3 g of the magnesium reagent in shavings were added followed by 0.5 ml of dibromoethane. The mixture was refluxed for 1 hour, 0.5 ml of dibromoethane were added and then reflux was continued for two hours. The mixture returned to ambient temperature to obtain the solution of the desired magnesium reagent titering 0.18M/liter.

Condensation

To a mixture of 12 g of the 5,10 epoxy compound of EP 0,057,115 (Example 7) and 600 mg of cuprous chloride in 150 ml of tetrahydrofuran, 570 ml of the magnesium reagent were added dropwise at −5° C. and the mixture was stirred for a further 30 minutes and poured into a mixture of 250 ml of a saturated solution of ammonium chloride and 250 g of ice. The mixture was extracted with chloroform and the organic phase was washed with a saturated solution of sodium chloride, dried and evaporated to to dryness under reduced pressure. The 35 g of the residue were chromatographed over silica (eluant: methylene chloride-acetone (85-15)) to obtain 13.5 g of the desired product.

| IR Spectrum: (CHCl$_3$) | |
|---|---|
| 17 keto | 1733 cm$^{-1}$ |
| OH primary | 3623 cm$^{-1}$ |
| OH at 5 | 3567 cm$^{-1}$ |

| IR Spectrum: (CHCl₃) | |
|---|---|
| C=C | 1625 cm⁻¹ |

Step B

11β(5-hydroxy pentyl)-Δ⁴,⁹-estradiene-3,17-dione

For 90 minutes, a mixture of 5 g of the product of Step A, 110 ml of ethanol and 28 ml of 2N hydrochloric acid was stirred and the mixture was made alkaline to pH of about 9 with concentrated ammonia. The mixture was washed with water, with a saturated solution of sodium chloride, dried and evaporated to dryness under reduced pressure. The 4.8 g of residue were chromatographed over silica (eluant: methylene chloride-acetone (85-15)) to obtain 3.97 g of the expected product.

| IR Spectrum: (CHCl₃) | |
|---|---|
| OH primary | 3264 cm⁻¹ |
| Ketone at 17 | 1736 cm⁻¹ |
| Dienone | 1656 cm⁻¹–1602 cm⁻¹ |

Step C 3,17-dioxo-11β-Δ⁴,⁹-estradiene-pentanoic acid

To a solution of 2.9 g of the product of Step B in 140 ml of acetone cooled down to −4° C., 1 ml of Heilbron-Jones reagent were added over 25 minutes at 0° to −4° C. and the mixture was stirred for a further 5 minutes at 0° C. The excess reagent was destroyed by the addition of 2.5 ml of methanol and a solution of 22 g of barium carbonate in 220 ml of water was added. The mixture was stirred for 1 hour at ambient temperature and filtered to remove the mineral salts which were washed 5 times with 200 ml of acetone. The acetone was evaporated and the aqueous phase was extracted 4 times with 200 ml of methylene chloride. The organic phase was washed with water, with sodium chloride in saturated solution and evaporated to dryness under reduced pressure to obtain 3.4 g of the desired product used as such in the following step.

| IR Spectrum: (CHCl₃) | |
|---|---|
| 17 keto | 1736 cm⁻¹ |
| C=O | 1709 cm⁻¹ |
| Conjugated ketone | 1657 cm⁻¹ |
| C=C | 1602 cm⁻¹ |

PREPARATION 3

3,17-dioxo-11β-Δ⁴,⁹-estradiene-heptanoic acid

Step A 3-(1,2-ethanediyl cyclic acetal) of 11β-(7-hydroxy heptyl)-Δ⁹-estrene-5α-ol-3,17-dione Using the procedure of Step A of Preparation 2, 14.4 g of 1-chloro-7-heptanol [obtained in Preparation 10 starting from 13.9 g of the 5α, 10α-epoxide of EP 0,057,115 Example 7] yielded. 26.9 g of crude product which was chromatographed over silica (eluant: methylene chloride-acetone-triethylamine (85-15-0.4)) to obtain 9 g of the desired product. The latter was chromatographed once more (eluant: ethyl acetate-cyclohexane-triethylamine (60-40-0.4)) to obtain 8.17 g of the desired product.

| IR Spectrum: (CHCl₃) | |
|---|---|
| 17 keto | 1733 cm⁻¹ |
| Primary alcohol | 3622 cm⁻¹ |
| Tertiary alcohol OH | 3508 cm⁻¹ |

Step B

11β-(7-hydroxyheptyl)-Δ⁴,⁹-estradiene-3,17-dione

Using the procedure of Step B of Preparation 2, 2.5 g of the product of Step A were reacted and after chromatography over silica (eluant: cyclohexane-diethyl acetate (1—1)), 1.935 g of the desired product were obtained.

| IR Spectrum: | |
|---|---|
| CH₂OH | 3626 cm⁻¹ |
| 17 keto | 1734 cm⁻¹ |
| Dienone | 1654–1602 cm⁻¹ |

STEP C 3,17-dioxo-11β-Δ⁴,⁹-estradiene heptanoic acid

Using the procedure of Step C of Preparation 2, 3.2 g of the product of Step B were reacted to obtain 3.04 g of the desired product which was used as such in the following step.

PREPARATION 4

17β-acetyloxy-11β-[4-(8-hydroxy octyl)-phenyl]-Δ⁴,⁹-estradiene-3-one

Step A 3-(1,2-ethanediyl cyclic acetal) of 11β-[4-[8-[[(1,1-dimthyl ethyl)-dimethylsilyl]-oxy]-octyl]-phenyl]-Δ⁹-estrene-5α-ol-3,17-dione Using the procedure of Step A of Preparation 1, 3.171 g of the epoxide of EP 0,057,115 (Example 7) and 9.9 g of dimethyl tert.-butyl silyl octanyloxy bromobenzene (of Preparation 11) were reacted to obtain after chromatography over silica (eluant: cyclohexane-ethyl-acetate (6-4)), 4.127 g of the desired product.

| IR Spectrum: (CHCl₃) | |
|---|---|
| OH type 5-OH | 3510 cm⁻¹ |
| Aromatic | 1510 cm⁻¹ |
| $O-\underset{\underset{Me}{\vert}}{\overset{\overset{Me}{\vert}}{Si}}-Me$ | 836 cm⁻¹ |
| 17 keto | 1733 cm⁻¹ |

Step B 3-(1,2-ethanediyl cyclic acetal) of 11β-[4-[8-[[(1,1-dimethyl ethyl)-dimethylsilyl]-oxy]-octyl]-phenyl]-Δ⁹-estren-5α,17β-diol-3-one Using the procedure of Step B of preparation 1, 2.62 g of the product of Step A were reacted to obtain 2.6 g of the desired product for use as is in the following step.

| IR Spectrum: (CHCl₃) on the chromatographed product | |
| --- | --- |
| Absence of C=O | |
| 17-OH | 3612 cm⁻¹ |
| 5-OH | 3508 cm⁻¹ |
| Aromatic | 1509 cm⁻¹–1472 cm⁻¹ |
| O—Si | |

Step C 3-(1,2-ethanediyl cyclic acetal) of 17β-acetyloxy-11β-[4-[8-[[(1,1-dimethyl ethyl)-dimethylsilyl]-oxy]-octyl]-phenyl]-Δ⁹-estren-5α-ol-3-one Using the procedure of (a) Step C of preparation 1, the product of Step B was reacted to obtain after chromatography on silica (eluant: cyclohexane-ethyl acetate (6-4)), 2.58 g of the desired product.

| IR Spectrum: (CHCl₃) | |
| --- | --- |
| C=O | 1728 cm⁻¹ |
| 5-OH | 3508 cm⁻¹ |
| Aromatic | 1508 cm⁻¹ |
| O—Si | |

Step D

17β-acetyloxy-11β-[4-(8-hydroxy-octyl)-phenyl]-Δ⁴,⁹-estradien-3-one

Using the procedure of (b) Step C of preparation 1, the product of Step C was reacted to obtained after chromatography on silica (eluant: cyclohexane-ethyl acetate (5-5)), 1.2 g of the desired product.

| IR Spectrum: (CHCl₃) | |
| --- | --- |
| Absence of O—Si | |
| OH | 3622 cm⁻¹ |
| C=O | 1728 cm⁻¹ |
| dienone | 1656 cm⁻¹ |
| | 1602 cm⁻¹ |
| Aromatic | 1509 cm⁻¹ |

PREPARATION 5

17β-acetyloxy-3-oxo-11β-Δ⁴,⁹-estradiene undecanoic acid

Step A 3-(1,2-ethanediyl cyclic acetal) of 11β-[11-[[dimethyl-(1,1-dimethyl ethyl)-silyl]-oxy]-undecyl]-Δ⁹-estrene-5-ol-3,17-dione Using the procedure of Step A of preparation 1, 17.5 g of the epoxide of EP 0,057,115 (Example 7) and 500 ml of a 0.32M suspension in tetrahydrofuran of 11-(dimethyl-tert-.butylsilyloxy)-undecyl magnesium bromide (prepared by ICI Patent No. 85-100658) were reacted to obtain after chromatography on silica (eluant: cyclohexane-ethyl acetate (95-5 then 5-5)), 15.3 g of the desired product.

| IR Spectrum: (CHCl₃) | |
| --- | --- |
| 5-hydroxy | 3510 cm⁻¹ |
| 17 keto | 1733 cm⁻¹ |

Step B (1,2-ethanediyl cyclic acetal) of 11β-[11-[[dimethyl-(1,1-dimethyl ethyl)-silyl]-oxy]-undecyl]-Δ⁹-estren-5α, 17β-diol-3-one Using the procedure of Step B of preparation 1, 15.2 g of the product of Step A were reacted to obtain 14.863 g of the desired product, which was used as is for the following step.

| IR Spectrum: (CHCl₃) | |
| --- | --- |
| 17-OH | 3613 cm⁻¹ |
| 5-OH | 3508 cm⁻¹ |
| O—Si | |
| Intense aliphatic | |

Step C (1,2-ethanediyl cyclic acetal) of 17β-acetyloxy-11β-[11-[[dimethyl-(1,1-dimethyl ethyl)-silyl]-oxy]-undecyl]-Δ⁹-estren-5α-ol-3-one A mixture of 13.335 g of the product of Step B, 53 ml of pyridine and 26 ml of acetic anhydride was stirred for 4 hours 30 minutes at ambient temperature and was then cooled and neutralized by adding, over 45 minutes, sodium bicarbonate. The mixture was extracted with ethyl acetate, washed with water, dried and evaporated to dryness under vacuum to obtain 15 g of the desired product which was used as is for the following step.

| IR Spectrum: (CHCl₃) | |
| --- | --- |
| 5-OH | 3515 cm⁻¹ |
| C=O | 1728 cm⁻¹ |

Step D

17β-acetoxy-11β-(11-hydroxy undecyl)-Δ⁴,⁹-estradien-3-one

A mixture of 15 g of the product of Step C, 300 ml of methanol and 75 ml of 2N hydrochloric acid was stirred for 2 hours 45 minutes and then 20 ml of concentrated ammonia were added and the methanol was evaporated under vacuum. The mixture was extracted with ethyl acetate and the organic phase was washed with water saturated with sodium chloride, dried and evaporated to dryness under vacuum to obtain 12.75 g of product which was chromatographed on silica (eluant: cyclohexane-ethyl acetate (5-5)) to obtain 8.37 g of the desired product.

| IR Spectrum: (CHCl₃) | |
| --- | --- |
| free and associated OH | 3613 cm⁻¹ |
| C=O | 1729 cm⁻¹ |
| dienone | 1654 cm⁻¹ |

-continued

| IR Spectrum: (CHCl₃) |
|---|
| 1601 cm$^{-1}$ |

Step E

17β-acetoxyloxy-3-oxo-11β-Δ$^{4,9}$-estradiene-undecanoic acid

Using the procedure of Step C of preparation 1, 8.37 g of the product of Step D were reacted to obtain after chromatography on silica (eluant: cyclohexane-ethyl acetate (5-5)), 6.67 g of the desired product.

| IR Spectrum: (CHCl₃) Presence of acid in the OH region ||
|---|---|
| C=O | 1728 cm$^{-1}$ |
|  | 1712 cm$^{-1}$ |
| dienone | 1654 cm$^{-1}$ |
|  | 1600 cm$^{-1}$ |
| aliphatic very intense. ||

PREPARATION 6

3,17-dioxo-11β-Δ$^{4,9}$-estradiene undecanoic acid

Step A

11β-(11-hydroxy undecyl)-Δ$^{4,9}$-estradiene-3,17-dione

A mixture of 1 g of the product of Step A of preparation 5, 20 ml of methanol and 5 ml of 2N hydrochloric acid was stirred for 75 minutes at ambient temperature and the mixture was made alkaline to pH approx. 9 with concentrated ammonia, then was evaporated to dryness under reduced pressure. The residue was taken up in ethyl acetate and the solution was washed with a saturated sodium chloride solution, dried and concentrated to dryness under reduced pressure. The dry extract was chromatographed on silica (eluant: cyclohexane-ethyl acetate (6-4)) to obtain 670 mg of the desired product.

| IR Spectrum: (CHCl₃) The presence of acid in the OH region ||
|---|---|
| OH | 3623 cm$^{-1}$ |
| 17 keto | 1736 cm$^{-1}$ |
| dienone | 1656 cm$^{-1}$ |
|  | 1602 cm$^{-1}$ |

Step B 3,17-dioxo-11β-Δ$^{4,9}$-estradiene undecanoic acid

Using the procedure of Step C of preparation 2, 10.4 g of the product of Step A were reacted to obtain 12.4 g of the desired product which was used as is for the following step.

| IR Spectrum: (CHCl₃) Absence of alcohol ||
|---|---|
| C=O | 1736 cm$^{-1}$ |
|  | 1709 cm$^{-1}$ |
| dienone | 1656 cm$^{-1}$ |
|  | 1601 cm$^{-1}$ |
| Presence of acid in the OH region. ||

PREPARATION 7

17β-hydroxy-3-oxo-17α-(1-propynyl)-11β-Δ$^{4,9}$-esterdiene undecanoic acid

Step A 3,3-dimethyl ketal of 5α,10α-epoxy-Δ$^{9,11}$-estradiene-3,17-dione

To a solution of 5 kg of 3,3-dimethyl ketal-Δ$^{4,9}$-estradien-17-one (French Patent No. 1,514,086) in 25 liters of methylene chloride and 25 ml of pyridine, 430 g of hexachloroacetone and 1.3 liters of 200 volume hydrogen peroxide were added and the mixture was stirred for 24 hours at 16° to 18° C. and poured into a mixture of 1,400 kg of sodium thiosulfate and 50 liters of demineralized water. The mixture was extracted with methylene chloride and the organic phase was evaporated to dryness under reduced pressure to obtain 7.29 kg of the desired product which was used as is for the following step.

Step B 3,3-dimethyl ketal of 11β-(11-dimethyl tert-butyl silyloxy undecyl)-Δ$^9$-estrene-5β-ol-3,17-dione To 600 ml of the magnesium derivative of bromo undecyloxy dimethyl tert-butyl silane (ICI Patent No. 85-100658) in 50 ml of tetrahydrofuran cooled to 0° C., there was added 1.58 g of cuprous chloride and the mixture was stirred for 30 minutes and cooled to −30° C. A solution of 18.17 g of the product of Step A in solution in 87 ml of tetrahydrofuran was added and the mixture was stirred for 3 hours and 30 minutes at ambient temperature, then poured into a solution of ammonium chloride at 0° C. The mixture was stirred for 10 minutes and extracted with ethyl acetate followed by methylene chloride. The organic phases were washed with saturated aqueous sodium chloride, dried and evaporated to dryness under reduced pressure. The 123 g of residue was chromatographed on silica (eluant: methylene chloride-ethyl acetate (9-1) with 1% of triethylamine) to obtain 5.19 g of the desired product used as is in the following step.

Step C

11β-(11-hydroxy undecyl)-17α-(1-propynyl)-Δ$^{4,9}$-estradiene-17β-ol-3-one 84 ml of butyl lithium in hexane (1.6 mol/liter) were cooled to −70° C. and slowly 84 ml of tetahydrofuran were added. Methyl acetylene was bubbled therethrough while maintaining the temperature at −50° C. and after 10 minutes, the temperature fell to the temperature fell to −70° C. The bubbling in was stopped and the mixture was stirred for 30 minutes at −70° C. 4.18 g of the product of Step B in solution in 80 ml of tetrahydrofuran were added and the temperature returned to ambient temperature. The mixture was stirred for 1 hour under these conditions and poured into a solution of ammonium chloride at 0° C. The mixture was extracted with ethyl acetate and then methylene chloride and the organic phases were washed, dried and evaporated to dryness under reduced pressure. The 6 g of residue were redissolved in 50 ml of ethanol and 10 ml of 2N hydrochloric acid and the mixture was stirred for 1 hour at ambient temperature and diluted with 100 ml of water. The mixture was extracted with chloroform and the organic phase was evaporated to dryness. The 4.9 g of residue were chromatographed on silica (eluant: cyclohexane-ethyl acetate (5-5)) to obtain 2.25 g of the desired product.

| Analysis for $C_{32}H_{48}O_3$ | | | |
|---|---|---|---|
| Calculated: | % C 79.95 | % H | 10.06 |
| Found: | 79.9 | | 10.1 |

Step D

17β-acetyloxy-11β-(11-hydroxy undecyl)-17α-(1-propynyl)-$\Delta^{4,9}$-estradien-3-one a) Diacetylation

A solution of 5.07 g of the product of Step C of Example 9 in 48 ml of pyridine, 1 g of 4-dimethylaminopyridine and 17.6 ml of acetic anhydride was stirred for 18 hours at 20° C. and then 200 ml of ice were added all at once. The mixture was neutralized with a saturated sodium bicarbonate solution and stirred for 30 minutes followed by extraction with methylene chloride. The organic phase was evaporated to dryness under reduced pressure and the 8 g of residue were chromatographed on silica (eluant: cyclohexane-ethyl acetate (5-5)) to obtain 2.83 g of the desired product.

b) Mono-Saponification

A solution of 2.8 g of the diacetylated product in 28 ml of methanol with 0.7 g of potassium bicarbonate was heated to 70° C. for 90 minutes and then 100 ml of iced water were added. The mixture was extracted with methylene chloride and the organic phase was evaporated to dryness. The 2.6 g of residue were chromatographed on silica (eluant: cyclohexane-ethyl acetate (5-5)) to obtain 1.18 g of the desired product used as is for the following step.

Step E

17β-acetyloxy-3-oxo-17α-(1-propynyl)-11β-$\Delta^{4,9}$-estradiene undecanoic acid To a solution of 460 mg of the product of Step A in 24 ml of acetone, 0.8 ml of a solution prepared from 57 ml of concentrated sulfuric acid, 67 g of chromic oxide and sufficient water to make to 250 ml were added over 1 hour at 0° C.

8 drops of methanol, 28 ml of water and 8 g of barium carbonate were added to the reaction solution at 0° C. and the mixture was stirred for 1 hour at 0° C. and filtered to remove the insoluble material. The filtrate was extracted with methylene chloride and the organic phase was evaporated to dryness under reduced pressure and the 384 mg of residue were chromatographed on silica (eluant: cyclohexane-ethyl acetate (5-5)) to obtain 198 mg of the desired product.

Step F

17β-hydroxy-3-oxo-17α-(1-propynyl)-11β-$\Delta^{4,9}$-estradiene undecanoic acid A solution of 722 mg of the product of Step B in 8 ml of a 1M solution of methanolic potassium hydroxide was stirred at room temperature for one hour and 10 g of ice, then 10 ml of normal hydrochloric acid were added all at once. The mixture was extracted with methylene chloride and the organic phase was evaporated to dryness under reduced pressure to obtain 593 mg of the desired product used as is for the following step.

PREPARATION 8

11β-(12-hydroxy dodecyl)-$\Delta^{4,9}$-estradiene-3,17-dione

Step A 3-(1,2-ethanediyl cyclic acetal) of 11β-[[12-[(1,1-dimethylethyl)-dimethylsilyl]-oxy]-dodecyl]-$\Delta^9$-estrene-5α-ol-3,17-dione Using the procedure of Step A of preparation 1, 2.97 g of the epoxide of European Patent No. 0,057,115 (Example 7) and 12 g of dodecanoxy dimethyl tert-butyl silane magnesium bromide (preparation 13) were reacted to obtain, after chromatography on silica (eluant: cyclohexane-ethyl acetate (6-4)), 5.24 g of the desired product.

| IR Spectrum: (CHCl₃) | |
|---|---|
| OH | 3510 cm⁻¹ |
| C=O | 1733 cm⁻¹ |
| O—Si< | 836 cm⁻¹ |

Step B

11β-(12-hydroxy-dodecyl-$\Delta^{4,9}$-estradiene-3,17-dione

Using the procedure of Step A of Preparation 6, 5.2 g of the product of Step A were reacted and after chromatography on silica (eluant: cyclohexane-ethyl acetate (6-4)), 2.78 g of the desired product were obtained.

| IR Spectrum: (CHCl₃) | |
|---|---|
| OH | 3625 cm⁻¹ |
| C=O | 1736 cm⁻¹ (17 acetate) |
| Dienone | 1656 cm⁻¹ |
| | 1602 cm⁻¹ |

PREPARATION 9

Phenethoxy dimethyl tert-buty silyl bromide

To a solution of 15 g of 4-bromophenethyl alcohol in 60 ml of tetrahydrofuran at 0° C. to 5° C., 10.6 g of imidazole were added followed by addition over 30 minutes of a solution of of 14.33 g of dimethyl tert-butyl chlorosilane in 20 ml of tetrahydrofuran at 0°±2° C. The mixture was diluted with 40 ml of tetrahydrofuran and was then stirred for 2 hours at ambient temperature and filtered to remove the insoluble material. The filtrate was evaporated to dryness under reduced pressure and the 32.89 g of residue were chromatographed on silica (eluant: cyclohexane-ethyl acetate (95-5)), to obtain 24 g of the desired product.

| IR Spectrum: (CHCl₃) |
|---|
| Absence of OH |
| Presence of O—Si< 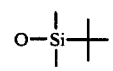 |

PREPARATION 10

1-chloro-7-heptanol (used in Step A of Preparation 3)

A mixture of 44 g of heptane diol, 400 ml of concentrated hydrochloric acid, 150 ml of toluene and 50 ml of water was stirred for two and half hours at reflux. The toluene fraction was removed and 200 ml of toluene were added to the aqueous fraction and the mixture was heated for five hours at 85° C. to 90° C. The toluene was removed and 200 ml of toluene and 100 ml of concentrated hydrochloric acid were added to the aqueous phase. The mixture was heated for five hours, then cooled and the organic fraction was combined with the two preceding toluene fractions. The toluene fraction was washed with water, dried and evaporated to dryness under reduced pressure, then distilled at 70° C. under 0.5 mm of mercury to obtain 37 g of the desired product.

| Analysis: $C_7H_{15}Cl_1O$; molecular weight = 150.65 | | | |
|---|---|---|---|
| Calculated: | % C 55.81 | % H 10.03 | % Cl 23.53 |
| Found: | 55.8 | 10.2 | 23.8 |
| IR Spectrum: (CHCl$_3$) | | | |
| Primary OH | | 3615 cm$^{-1}$ | |

PREPARATION 11

Dimethyl tert-butyl silyl octyloxy bromobenzene

STEP A

Chlorohexyloxy dimethyl tert-butyl silyl

To a mixture of 40.93 g of 1-chlorohexanol, 42.9 g of imidazole and 102 ml of tetrahydrofuran, a solution of 56.07 g of dimethyl tert-butyl silyl chloride in 114 ml of tetrahydrofuran was added at 15° to 18° C. and the mixture was stirred for 15 hours at ambient temperature and then centrifuged to remove the precipitate. Chromatography on silica (eluant: cyclohexane-ethyl acetate (95-5)) obtained 74.28 g of the desired product.

STEP B

Dimethyl tert-butyl silyl octyloxy bromobenzene a) Chlorohexyloxy dimethyl tert-butyl silyl magnesium A solution of 74.82 g of the product of Step A in 300 ml of tetrahydrofuran was added to a suspension of 0.871 g of magnesium and 271 ml of tetrahydrofuran and the mixture was refluxed for 4 hours and cooled to obtain the desired magnesium derivative with a titer approximately 0.375 mol/liter.

50 g of iodoethyl benzene (Preparation 12) in 500 ml of tetrahydrofuran were added at −70° C. over 15 minutes to 640 ml of the magnesium derivative solution and the mixture was stirred while allowing a return to ambient temperature and the stirring was continued for 15 hours. 500 ml of water saturated with ammonium chloride were added and the mixture was stirred for 15 minutes. The decanted organic phase was washed, dried and evaporated to dryness and the 101.3 g of residue were chromatographed on silica (eluant: cyclohexane) obtain 39.5 g of the desired product.

PREPARATION 12

1-p-bromophenethyl iodide

STEP A 1-p-bromophenethyl alcohol

To a solution of 95.2 g of 4-bromophenyl acetic acid in 950 ml of tetrahydrofuran. 49 ml of 10M borane-dimethyl sulfide complex were added over 35 minutes at 15° to 20° C. and the mixture was refluxed over 20 minutes and maintained for 10 minutes, then cooled. 50 ml of water were added and the mixture was extracted with ethyl acetate and evaporated to dryness under reduced pressure. The 102 g of residue were chromatographed on silica (eluant: cyclohexane-ethyl acetate (6-4)) to obtain the desired product.

Step B 1-p-bromophenethyl p-toluene sulfonate

To a solution of 41 g of the alcohol of Step A in 102 ml of pyridine, 77.72 g of tosyl chloride were added over 35 minutes at 5° C.±1° C. and the mixture was stirred for another 30 minutes at 5° C., then allowed to return to ambient temperature. 500 ml of of saturated sodium bicarbonate solution were added and the mixture was extracted with ethyl acetate. The organic phase was evaporated to dryness under reduced pressure to obtain 71.4 g of the desired product melting at 92° C.

Step C 1-p-bromophenethyl iodide

To a solution of 71.4 g of the p-toluene sulfonate of Step B in 1,400 ml of acetone, 45.12 g of sodium iodide were added and the mixture was heated to a slight reflux which was maintained for 2 hours, then cooled. The mixture was centrifuged to remove the precipitate which was washed with acetone. The filtrate was evaporated to dryness under reduced pressure and the 80.5 g of residue were chromatographed on silica (eluant: cyclohexane-ethyl acetate (8-2)) to obtain 60.54 g of the desired product melting approximately at 40° C.

PREPARATION 13

Bromododecanoxy dimethyl tert-butyl silane

To a solution of 10 g of 12-bromo-1-decanol in 40 ml of tetrahydrofuran, 5.48 g of imidazole were added and over 10 minutes a solution of 7.058 g of dimethyl tert-butyl chlorosilane in 10 ml of tetrahydrofuran were added. The mixture was stirred for one hour at ambient temperature and the insoluble material was filtered off. The filtrate was concentrated to dryness under reduced pressure and the residue was chromatographed on silica (eluant: cyclohexane-ethyl acetate (95-5)) to obtain 13.57 g of the desired product usable as is for Step A of Example 15.

| IR Spectrum: (CHCl$_3$) | |
|---|---|
| Little or no OH | |
| Probable O—Si | 1257 cm$^{-1}$ |
| | 837 cm$^{-1}$ |
| Intense aliphatic | |

EXAMPLE 1

4-(17β-hydroxy-3-oxo-Δ$^{4,9}$-estradien-11-yl)-N-methyl-N-benzene acetamide

Step A 4-(17β-acetyloxy-3-oxo-Δ$^{4,9}$-estradien-11β-yl)-N-methyl-N-isopropyl-benzene acetamide a) Oxidation

A solution of 3.3 g of the product of Step C of Preparation 1 in 200 ml of acetone was cooled to 0° C. and 6.36 ml of a solution prepared from 67 g of chromic oxide, 57 ml of sulfuric acid and demineralized water sufficient for 250 ml were added over 20 minutes at +2°-+3° C. and the mixture was stirred for 5 minutes. 4 ml of methanol and 16 g of barium carbonate were added and the mixture was stirred for one hour and permitted to return to ambient temperature. The mixture was filtered, washed with acetone and evaporated to dryness to obtain 3.282 g of residue.

b) Amidification

To a solution cooled to −10° C. of 3.282 g of the above product in 150 ml of methylene chloride, 3 ml of N-methyl morpholine and 3.3 ml of isobutyl chloroformate were added and the mixture was stirred for 30 minutes at −10° C. 3.3 ml of N-isopropyl methylamine were added and the temperature was allowed to rise. After stirring for 30 minutes, the mixture was poured into an iced sodium bicarbonate solution, stirred for 10 minutes and extracted with methylene chloride. The organic phase was evaporated to dryness and the 7.6 g of residue were chromatographed on silica (eluant: methylene chloride-acetone (9-1)) to obtain 2.15 g of the desired product.

| IR Spectrum: CHCl$_3$ (on Nicolet) | |
|---|---|
| C=O | 1728 cm$^{-1}$ OAC |
| Dienone | 1654 cm$^{-1}$ |
| | 1608 cm$^{-1}$ |
| C=O | 1624 cm$^{-1}$ Tertiary amide |
| Aromatic | 1509 cm$^{-1}$ |

Step B 4-(17β-hydroxy-3-oxo-Δ$^{4,9}$-estradien-11β-yl)-N-methyl-N-isopropyl-benzene acetamide A solution of 0.5 g of the product of Step A, 15 ml of methanol and 336 mg of potassium hydroxide was stirred for one hour and then cooled to 0° C. and neutralized by the addition of 7.4 ml of 2N hydrochloric acid. The mixture was extracted with methylene chloride and evaporated to dryness under reduced pressure. The 459 mg of residue were chromatographed on silica (eluant: ethyl acetate-cyclohexane (9-1)) to obtain 0.288 g of the desired product.

| Analysis: C$_{30}$H$_{39}$NO$_3$; molecular weight = 461.65 | | | | | |
|---|---|---|---|---|---|
| Calculated: | % C 78.05 | | % H 8.52 | | % N 3.03 |
| Found: | 77.8 | | 8.6 | | 3.1 |
| IR Spectrum: CHCl$_3$ (on Nicolet) | | | | | |
| OH | | 3612 cm$^{-1}$ | | | |
| C=O | | 1653 cm$^{-1}$ | | | |
| | | 1623 cm$^{-1}$ | | | |
| Aromatic | | 1570 cm$^{-1}$ | | | |
| | | 1509 cm$^{-1}$ | | | |

EXAMPLE 2

4-(3,17β-dihydroxy-Δ$^{1,3,5(10)}$-estratrien-11β-yl)-N-methyl-N-isopropyl-benzene acetamide To a solution of 1.045 g of the product of Step A of Example 1 in 20 ml of methanol, 2 g of palladium hydroxide with 20% magnesium oxide were added and the mixture was refluxed for 30 minutes then filtered off the catalyst. The filtrate was washed with methanol and evaporated to dryness under reduced pressure. The 1.03 g of residue were redissolved in 30 ml of methanol and 980 mg of potassium hydroxide pellets were added. The mixture was stirred for 45 minutes at ambient temperature and 50 g of ice and 20 ml of 2N hydrochloric acid were added. The mixture was extracted with methylene chloride and the organic phase was evaporated to dryness under reduced pressure. The 1.1 g of residue were chromatographed on silica (eluant: ethyl acetate-cyclohexane (8-2)) to obtain 467 mg of the desired product.

| Analysis: C$_{30}$H$_{39}$NO$_3$; molecular weight = 461.641 | | | |
|---|---|---|---|
| Calculated: | % C 78.05 | % H 8.51 | % N 3.03 |
| Found: | 78.2 | 8.5 | 2.9 |
| IR Spectrum: CHCl$_3$ (on Nicolet) | | | |
| OH | 3602 cm$^{-1}$ + associated | | |
| C=O | 1620 cm$^{-1}$ | | |
| | 1580 cm$^{-1}$ (ep.) | | |
| Aromatic | 1513 cm$^{-1}$ | | |
| | 1501 cm$^{-1}$ (max.) | | |

EXAMPLE 3

N-butyl-3,17β-dihydroxy-11βΔ$^{1,3,5(10)}$-estratriene-pentanamide

Step A

N-butyl-3,17-dioxo-11β-Δ$^{4,9}$-estradien-pentanamide

To a solution of 3.4 g of the product of Step C of Preparation 2 in 64 ml of methylene chloride at −10° to −15° C., 3.25 ml of N-methyl morpholine were added dropwise followed by 3.8 ml of isobutyl chloroformate and the mixture was stirred for 30 minutes at −10° to −15° C. and then at this temperature, 4.1 of N-butylamine were added. The mixture was allowed to return to ambient temperature and after 40 mintues, 100 ml of a saturated sodium bicarbonate solution were added. The mixture was stirred for 10 minutes and the decanted aqueous phase was extracted with methylene chloride. The organic phase was washed with a saturated sodium chloride solution, dried and evaporated to dryness under reduced pressure. The 7 g of residue were chromatographed on silica (eluant: methylene chloride-acetone (8-2)) and after evaporation to dryness, 2.3 g of the desired product were obtained.

| IR Spectrum: (CHCl$_3$) | |
|---|---|
| 17 ketone | 1736 cm$^{-1}$ |
| NH | 3349 cm$^{-1}$ |
| Amide II | 1519 cm$^{-1}$ |
| Dienone + C=C | 1602 cm$^{-1}$ |
| | 868 cm$^{-1}$ |

IR Spectrum: (CHCl₃)

| | |
|---|---|
| Dienone + amide | 1658 cm⁻¹ |

Step B

3-acetyloxy-N-butyl-17-oxo-11β-Δ$^{1,3,5(10)}$-estratrien-pentanamide

To a solution of 2.3 g of the product of Step A in 25 ml of methylene chloride at 0° C. to −5° C., 2.5 ml of acetic anhydride and 1.25 ml of acetyl bromide were added and the mixture was stirred for 80 minutes at ambient temperature and then poured into a mixture of 150 ml of saturated sodium bicarbonate solution and 50 g of ice. The mixture was stirred for 15 minutes and extracted with methylene chloride. The organic phase was evaporated to dryness under reduced pressure and washed twice with toluene to obtain 2.9 g of product which was chromatographed on silica (eluant: methylene chloride-acetone (9-1)) to obtain 2.3 g of the desired product.

IR Spectrum: (CHCl₃)

| | | |
|---|---|---|
| Aromatics | | 1610 cm⁻¹ |
| | | 1582 cm⁻¹ |
| | | 1494 cm⁻¹ |
| | NH= | 3349 cm⁻¹ |
| Secondary amide | Amide II | 1518 cm⁻¹ |
| | C=O | 1661 cm⁻¹ |
| 17 ketone | | 1736 cm⁻¹ |
| | | 1408 cm⁻¹ |
| Acetate | | 1760 cm⁻¹ |
| | | 1770 cm⁻¹ |
| Methyl (acetate) | | 1371 cm⁻¹ |

Step C

N-butyl-3,17β-dihydroxy-11β-Δ$^{1,3,5(10)}$-estratrien-pentanamide

To a solution of 1.85 g of the product of Step B in 16 ml of methanol at 0° to 5° C., 192 mg of sodium borohydride were added and the mixture was stirred for 30 minutes. 640 mg of potassium hydroxide pellets were added and after 20 minutes at ambient temperature, 50 g of iced water (1-1) were added and the pH was adjusted to 4-5 with 2N hydrochloric acid. The mixture was saturated with sodium chloride and extracted with ethyl acetate. The organic phase was evaporated to dryness and the residue was chromatographed on silica (eluant: methylene chloride-acetone (75-25)) to obtain 1.56 g of the desired crude product. The latter was dissolved in 5 ml of methanol and 75 ml of methylene chloride were added. The mixture was filtered and concentrated to crystallization. The mixture was refrigerated for 3 hours, and centrifuged to obtain 1.33 g of the desired product melting at ≃100° C. (approximately) with a specific rotation of $[\alpha]_D$+117.5°±2° (c=1% in EtOH).

Analysis: C₂₇H₄₁O₃N; molecular weight = 427.63

| | % C | % H | % N |
|---|---|---|---|
| Calculated: | 75.83 | 9.66 | 3.27 |
| Found: | 75.5 | 9.8 | 3.2 |

IR Spectrum: Nujol

| | |
|---|---|
| Strong absorption in the NH/OH region | 3389 cm⁻¹ |
| | 3202 cm⁻¹ |
| C=O Amide | 1653 cm⁻¹ |

| | |
|---|---|
| Amide II | 1532 cm⁻¹ |
| Aromatics | 1610 cm⁻¹ |
| | 1582 cm⁻¹ |
| | 1502 cm⁻¹ |

EXAMPLE 4

N-butyl-3,17β-dihydroxy-N-methyl-11β-Δ$^{1,3,5(10)}$-estratrien-pentanamide

Step A

N-butyl-3,17-dioxo-N-methyl-11β-Δ$^{4,9}$-estradiene-pentanamide

Using the procedure of Step A of Example 3, 3 g of the acid of Step C of Preparation 2 and 4.1 ml of N-methyl butylamine instead of the N-butylamine were reacted to obtain 2.82 g of the desired product.

IR Spectrum: (CHCl₃)
Absence of acid

| | |
|---|---|
| 17 keto | 1736 cm⁻¹ |
| Tertiary amide | 1630 cm⁻¹ |
| Ketone conjugated with the tertiary amide | 1642 cm⁻¹ |
| C=C | 1603 cm⁻¹ |

Step B

3-acetyloxy-N-butyl-N-methyl-17-oxo-11β-Δ$^{1,3,5(10)}$-estratriene-pentanamide Using the procedure of Step B of Example 3, 2.8 g of the product were reacted to obtain 2.62 g of the desired product.

IR Spectrum: (CHCl₃)

| | |
|---|---|
| 17 keto + phenolic acetate | 1736 cm⁻¹ |
| Tertiary amide | 1627 cm⁻¹ |
| Aromatic | 1586 cm⁻¹ |
| | 1493 cm⁻¹ |

Step C

N-butyl-3,17β-dihydroxy-N-methyl-11β-Δ$^{1,3,5(10)}$-estratriene-pentanamide Using the procedure of Step C of Example 3, 2.5 g of the product of Step B were reacted to obtain 2.026 g of the desired product. An analytical sample was prepared by dissolving 1.8 g of the product in 100 ml of ethyl acetate at 60° C. and after filtration, the filtrate was concentrated to the start of crystallization, then stirred for 3 hours at 0° C., and centrifuged to obtain 1.58 g of the desired product melting at approximately 165° C. and with a specific rotation of $[\alpha]_D$=+113°±2° (c=1% in EtOH).

Analysis: C₂₈H₄₃O₃N; molecular weight = 441.66

| | % C | % H | % N |
|---|---|---|---|
| Calculated: | 76.15 | 9.81 | 3.17 |
| Found: | 76.0 | 10.0 | 3.0 |

IR Spectrum: (CHCl₃)

| | |
|---|---|
| Tertiary amide ketone | 1625 cm⁻¹ |
| OH | 3601 cm⁻¹ |
| Aromatic | 1585 cm⁻¹-1499 cm⁻¹ |

EXAMPLE 5

N-butyl-3,17β-dihydroxy-11β-$\Delta^{1,3,5(10)}$-estratriene-heptanamide

Step A

N-butyl-3,7-dioxo-11β-estra-$\Delta^{4,9}$-estradiene heptanamide

Using the procedure of Step A of Example 3, 2.6 g of the acid of Step C of Preparation 3 were reacted to obtain 1.845 g of the desired product.

| IR Spectrum: (CHCl$_3$) Absence of OH | |
|---|---|
| 17 keto | 1736 cm$^{-1}$ |
| Dienone + amide | 1659 cm$^{-1}$ |
| | 1602 cm$^{-1}$ } for C=C |
| | 864 cm$^{-1}$ |
| NH | 3450 cm$^{-1}$ |
| Amide II | 1519 cm$^{-1}$ |

Step B 3-acetyloxy-N-butyl-17-oxo-11β-$\Delta^{1,3,5(10)}$-estratriene-heptanamide Using the procedure of Step B of Example 3, 2.025 g of the product of Step A were reacted to obtain 1.95 g of the desired product.

| IR Spectrum: (CHCl$_3$) | |
|---|---|
| C=O | 1735 cm$^{-1}$ |
| C=O Amide | 1660 cm$^{-1}$ |
| Amide II | 1518 cm$^{-1}$ |
| NH | 345 cm$^{-1}$ |

Step C

N-butyl-3,17β-dihydroxy-11β-$\Delta^{1,3,5(10)}$-estratriene-heptanamide

Using the procedure of Step C of Example 3, 1.68 g of the product of Step B were reacted to obtain after chromatography on silica (eluant: methylene chloride-acetone (8-9)), 1.277 g of the desired product. A sample for analysis was prepared by crystallization of 1.2 g of the crude product in ethyl acetate to obtain 1.04 g of the desired product melting at approximately 139° C. and having a specific rotation of $[\alpha]_D = +113° \pm 2°$ (c=1% in ethanol).

| Analysis: C$_{29}$H$_{45}$O$_3$N; molecular weight = 455.65 | | | |
|---|---|---|---|
| Calculated: | % C 76.44 | % H 9.95 | % N 3.07 |
| Found: | 76.5 | 10.1 | 3.0 |

| IR Spectrum: (CHCl$_3$) | |
|---|---|
| OH + associated | 3604 cm$^{-1}$ |
| NH | 3448 cm$^{-1}$ |
| C=O | 1657 cm$^{-1}$ |
| Amide II | 1522 cm$^{-1}$ |
| Aromatic | 1620 cm$^{-1}$ |
| | 1609 cm$^{-1}$ |
| | 1584 cm$^{-1}$ |
| | 1499 cm$^{-1}$ |

EXAMPLE 6

N-butyl-3,17β-dihydroxy-N-methyl-11β-$\Delta^{1,3,5(10)}$-estratriene-heptanamide

Step A

N-butyl-3,17-dioxo-N-methyl-11β-$\Delta^{4,9}$-estradiene-heptanamide

Using the procedure of Step A of Example 5, 3.04 g of the acid of Step C of Preparation 3 and 3.8 ml of N-methyl butylamine was reacted to obtain 3 g of the desired product.

| IR Spectrum: (CHCl$_3$) Absence of OH | |
|---|---|
| 17 keto | 1736 cm$^{-1}$ |
| C=O complex | 1656 cm$^{-1}$ (conjugated ketone) |
| | 1629 cm$^{-1}$ (tertiary amide) |
| C=C | 1603 cm$^{-1}$ |

Step B 3-acetyloxy-N-butyl-N-methyl-17-oxo-11β-$\Delta^{1,3,5(10)}$-estratriene-heptanamide Using the procedure of Step B of Example 5, 2.95 g of the product of Step A were reacted to obtain 2.7 g of the desired product.

| IR Spectrum: (CHCl$_3$) | |
|---|---|
| C=O | 1760 cm$^{-1}$ (ep.) phenolic OAC region |
| | 1736 cm$^{-1}$ (max) 17 keto |
| | 1627 cm$^{-1}$ Amide III |
| Aromatic | 1585 cm$^{-1}$ (ep.) |
| | 1493 cm$^{-1}$ (F) |

Step C

N-butyl-3,17β-dihydroxy-N-methyl-11β-$\Delta^{1,3,5(10)}$-estratriene-heptanamide Using the procedure of Step C of Example 5, 2.6 g of the product of Step B were reacted to obtain 2.067 g of the desired product. A sample for analysis was prepared by crystallizing 1.8 g of the product from chloroform to obtain 1.697 g of the desired product melting at 110° C. and having a specific rotation of $[\alpha]_D = 106.5° \pm 2°$ (c=1% in ethanol).

| Analysis: C$_{30}$H$_{47}$O$_3$N; molecular weight = 469.68 | | | |
|---|---|---|---|
| Calculated: | % C 76.71 | % H 10.09 | % N 2.98 |
| Found: | 76.4 | 10.03 | 2.9 |

EXAMPLE 7

N-butyl-4-(17β-hydroxy-3-oxo-$\Delta^{4,9}$-estradien-11β-yl)-N-methyl benzene octanamide

Step A

N-butyl-N-methyl-4-[17β-acetyloxy-3-oxo-11β-$\Delta^{4,9}$-estradien-11β-yl]-benzene octanamide a) 17β-acetoxy-3-oxo-11β-$\Delta^{4,9}$-estradiene-benzene octanoic acid Using the procedure of Step C of Preparation 2, 970 mg of the product of Step D of Preparation 4 were reacted to obtain 1.219 g of the desired product which was used as is for the amidification.

b) Amidification

Using the procedure of Step A of Example 3, 1.219 g of the above product and 1.1 ml of N-methyl butylamine were reacted to obtain after chromatography on silica (eluant: cyclohexane-ethyl acetate (5-5)), 842 mg of the desired product.

| IR Spectrum: (CHCl$_3$) Absence of acid | |
|---|---|
| C=O | 1728 cm$^{-1}$ (OAC) |
| Aromatic | 1509 cm$^{-1}$ |
| Dienone + Amide III | 1652 cm$^{-1}$ |
| | 1628 cm$^{-1}$ |

Step B

N-butyl-4-[17$\beta$-hydroxy-3-oxo-$\Delta^{4,9}$-estradien-11$\beta$-yl]-N-methyl benzene octanamide Using the procedure of Step B of Example 1, 716 mg of the product of Step A were reacted to obtain after chromatography on silica (eluant: cyclohexane-ethyl acetate (5-5)), 508 mg of the desired product with a specific rotation of $[\alpha]_D = +169°\pm3°$ (c=0.5% in EtOH).

| Analysis: C$_{37}$H$_{53}$NO$_3$; molecular weight = 559.79 | | | |
|---|---|---|---|
| Calculated: | % C 79.38 | % H 9.54 | % N 2.5 |
| Found: | 79.2 | 9.7 | 2.4 |
| IR Spectrum: (CHCl$_3$) | | | |
| OH + Associated | 3612 cm$^{-1}$ | | |
| Dienone + tertiary amide | 1628 cm$^{-1}$ | | |
| | 1643 cm$^{-1}$ | | |
| Aromatic | 1608 cm$^{-1}$ | | |

EXAMPLE 8

N-butyl-4-(3,17$\beta$-dihydroxy-$\Delta^{1,3,5(10)}$-estratrien-11-yl)-N-methyl benzene octanamide Step A N-butyl-4-[3,17-diacetyloxy-$\Delta^{1,3,5(10)}$-estratrien-11$\beta$-yl]-N-methyl benzene octanamide To a solution of 293 mg of the product of Step A of Example 7 in 3 ml of methylene chloride, there was added at 0° C. to 5° C. 0.15 ml of acetyl bromide and 0.3 ml of acetic anhydride, and the mixture was stirred for 2 hours at ambient temperature and then poured into a saturated sodium bicarbonate solution. The mixture was stirred for 30 minutes and extracted with methylene chloride. The organic phase was washed with water, dried and evaporated to dryness under vacuum. The 300 mg of residue were chromatographed on silica (eluant: cyclohexane-ethyl acetate (7-3)) to obtain 217 mg of the desired product.

| IR Spectrum: (CHCl$_3$) | |
|---|---|
| C=O | 1755 cm$^{-1}$ |
| | 1728 cm$^{-1}$ OAC |
| | 1627 cm$^{-1}$ Tertiary amide |
| Aromatic at 11 | 1509 cm$^{-1}$ |
| Aromatic A ring | 1494 cm$^{-1}$ |

Step B

N-Butyl-4-[3,17$\beta$-dihydroxy-$\Delta^{1,3,5(10)}$-estratrien-11$\beta$-yl]-N-methyl benzene octanamide At ambient temperature: 471 mg of the product of Step A in solution in 3.65 ml of methanolic potassium hydroxide was stirred for 40 minutes and then ice was added followed by 2.5 ml of 2N hydrochloric acid. The mixture was extracted with ethyl acetate, washed with water, dried and evaporated to dryness under vacuum. The 460 mg of residue were chromatographed on silica (eluant: cyclohexane-ethyl acetate (5-5)) to obtain 264 mg of the desired product with a specific rotation of $[\alpha]_D = +20°\pm2°$ (c=0.5% in EtOH).

| Analysis: C$_{37}$H$_{53}$O$_3$N; molecular weight = 559.79 | | | |
|---|---|---|---|
| Calculated: | % C 79.38 | % H 9.54 | % N 2.5 |
| Found: | 79.8 | 9.6 | 2.3 |
| IR Spectrum: (CHCl$_3$) | | | |
| OH | 3605 cm$^{-1}$ + Associated | | |
| C=O | 1621 cm$^{-1}$ Tertiary amide | | |
| Aromatic | 1583 cm$^{-1}$ | | |
| | 1500 cm$^{-1}$ | | |

EXAMPLE 9

N,N-dimethyl-17$\beta$-hydroxy-3-oxo-11$\beta$-$\Delta^{4,9}$-estradiene-undecanamide Step A N,N-dimethyl-17$\beta$-acetyloxy-3-oxo-11$\beta$-$\Delta^{4,9}$-estradiene-undecanamide Using the procedure of Step A of Example 3, 2.7 g of the product of Step E of Preparation 5 and 2.28 g of dimethylamine in solution in 20 ml of tetrahydrofuran were reacted to obtain 1.6 g of the desired product.

| IR Spectrum: (CHCl$_3$) Absence of acid | |
|---|---|
| OAC | 1728 cm$^{-1}$ |
| Dienone + Amide III | 1336 cm$^{-1}$ |
| | 1603 cm$^{-1}$ |

Step B

N,N-dimethyl-17$\beta$-hydroxy-3-oxo-11$\beta$-$\Delta$4,9-estradiene-undecanamide Using the procedure of Step B of Example 1, 780 mg of the product of Step A were reacted to obtain after chromatography on silica (eluant: methylene chloride-acetone (8-2)), 485 mg of the desired product with a specific rotation of $[\alpha]_D = -21.5°\pm2.5°$ (c=0.35% in EtOH).

| Analysis: C$_{31}$H$_{49}$NO$_3$; molecular weight = 483.74 | | | |
|---|---|---|---|
| Calculated: | % C 76.97 | % H 10.21 | % N 2.89 |
| Found: | 77.0 | 10.2 | 2.7 |
| IR Spectrum: (CHCl$_3$) | | | |
| OH | 3616 cm$^{-1}$ | | |
| Amide III | 1640 cm$^{-1}$ (complex) | | |
| Dienone | 1604 cm$^{-1}$ C=O | | |
| | 964 cm$^{-1}$ C=C | | |

EXAMPLE 10

N,N-dimethyl-3,17β-dihydroxy-11β-Δ$^{1,3,5(10)}$-estratriene-undecanamide

Step A 3,17β-diacetyloxy-N,N-dimethyl-11β-Δ$^{1,3,5(10)}$-estratriene-undecanamide Using the procedure of Step B of Example 3, 697 mg of the product of Step A of Example 9 were reacted to obtain 660 mg of the desired product.

| IR Spectrum: (CHCl$_3$) Absence of dienone | |
|---|---|
| Acetate | 1726 cm$^{-1}$ |
|  | 1745 cm$^{-1}$ (ep.) |
| Amide III | 1632 cm$^{-1}$ |
| Aromatic | 1494 cm$^{-1}$ |

STEP B 3,17β-dihydroxy-N,N-dimethyl-11β-Δ$^{1,3,5(10)}$-estratriene-undecanamide Using the procedure of Step B of Example 1 and isolating the product by crystallization in isopropanol, there were obtained 369 mg of the desired product melting at 130° C. and a specific rotation of $[\alpha]_D = +100° \pm 2°$ (c=0.95% in EtOH).

| Analysis: C$_{31}$H$_{49}$O$_3$N; molecular weight = 483.74 | | | |
|---|---|---|---|
| Calculated: | % C 76.97 | % H 10.21 | % N 2.89 |
| Found: | 77.0 | 10.4 | 2.7 |

| IR Spectrum: (CHCl$_3$) | |
|---|---|
| OH + Associated | 3605 cm$^{-1}$ |
| Amide III | 1627 cm$^{-1}$ |
| Aromatic | 1528 cm$^{-1}$–1498 cm$^{-1}$ |

EXAMPLE 11

N-butyl-17β-hydroxy-3-oxo-11β-Δ$^{4,9}$-estradiene-undecanamide

STEP A

17β-acetyloxy-N-butyl-3-oxo-11β-Δ$^{4,9}$-estradiene-undecanamide

Using the procedure of Step A of Example 3, 6.67 g of the product of Step E of Preparation 5 were reacted to obtain, after chromatography on silica (eluant: cyclohexane-ethyl acetate (1-1)), 6.911 g of the desired product. A second chromatography of 3.443 g of the product with the same eluant yielded 2.898 g of the purified product.

| Analysis: C$_{35}$H$_{55}$O$_4$N; molecular weight = 553.75 | | | |
|---|---|---|---|
| Calculated: | % C 75.9 | % H 10.01 | % N 2.52 |
| Found: | 75.6 | 10.1 | 2.7 |

| IR Spectrum: (CHCl$_3$) | |
|---|---|
| Little or no acid | |
| —C—NH with =C—N—H<br>‖<br>O | 3450 cm$^{-1}$ |
| Amide II | 1519 cm$^{-1}$ |
| C=O | 1657 cm$^{-1}$ |
| Acetate | 1728 cm$^{-1}$ |
| Dienone | 1255 cm$^{-1}$ |
|  | 1657 cm$^{-1}$ |
|  | 1601 cm$^{-1}$ |

Step B

N-butyl-17β-hydroxy-3-oxo-11β-Δ$^{4,9}$-estradiene-undecanamide 0.5 g of the product of Step A, 5 ml of methanol and 280 mg of potassium hydroxide pellets were stirred for 40 minutes at ambient temperature and 20 ml of ice were added. The mixture was neutralized with 2.5 ml of 2N hydrochloric acid and was extracted with ethyl acetate to obtain after evaporation to dryness 509 mg of product. The latter was chromatographed on silica (eluant: cyclohexane-ethyl acetate (1-1)) to obtain 287 mg of the desired product.

| IR Spectrum: (CHCl$_3$) | |
|---|---|
| OH | 3612 cm$^{-1}$ |
| =C—NH | 3450 cm$^{-1}$ |
| Amide II | 1518 cm$^{-1}$ |
| C=O | 1657 cm$^{-1}$ (secondary amide + dienone) |

| Analysis: C$_{33}$H$_{53}$NO$_3$; molecular weight = 511.8 | | | |
|---|---|---|---|
| Calculated: | % C 77.45 | % H 10.44 | % N 2.74 |
| Found: | 77.1 | 10.7 | 2.7 |

EXAMPLE 12

N-butyl-3,17β-dihydroxy-11β-Δ$^{1,3,5(10)}$-estratriene-undecan-amide

STEP A 3,17β-bis(acetyloxy)-N-butyl-11β-Δ$^{1,3,5(10)}$-estratriene-undecanamide Using the procedure of Step B of Example 3, 3 g of the product of Step A of Example 11 were reacted to obtain 3.66 g of crude product used as is for the following step.

| IR Spectrum: (CHCl$_3$) | | |
|---|---|---|
| —C—<br>‖<br>O | 1749 cm$^{-1}$ (ep.)<br>1726 cm$^{-1}$ (max) | |
| Acetate | 1254 cm$^{-1}$ (F) | |
| —C— amide<br>‖<br>O | 1660 cm$^{-1}$ | O<br>‖<br>—C—NH |
| =C—NH | 3450 cm$^{-1}$ | |
| Amide II | 1518 cm$^{-1}$ | |
| Aromatic | 1612 cm$^{-1}$<br>1583 cm$^{-1}$<br>1494 cm$^{-1}$ | |

STEP B

N-butyl-3,17β-dihydroxy-11β-Δ$^{1,3,5(10)}$-estratrien-undecanamide

To a solution of 2.96 g of the product of Step A in 74 ml of methanol there was added 8.9 ml of a solution of 6 ml of a 11 g % ml methanolic potassium hydroxide and the mixture was stirred for 2 hours at 60° C. and then was iced, and neutralized with 15 ml of normal hydrochloric acid. The methanol was distilled and the mixture was diluted with aqueous saturated sodium chloride and extracted with ethyl acetate. After evaporation to dryness, the 2.7 g of residue were chromatographed on silica (eluant: cyclohexane-ethyl acetate (5-5)) to obtain 1.841 g of the desired product. A sample for analysis was prepared by a second chromatogrphy under the same conditions to obtain 1.547 g of the desired compound with a specific rotation of $[\alpha]_D = +85° \pm 3°$ (c=0.5% in ethanol).

| Analysis: $C_{33}H_{53}NO_3$; molecular weight = 511.75 | | | |
|---|---|---|---|
| Calculated: | % C 77.45 | % H 10.43 | % N 2.73 |
| Found: | 77.5 | 10.7 | 2.9 |
| (lost under vacuum 1.5% at 100° C.) | | | |

| IR Spectrum: (CHCl₃) | |
|---|---|
| HO | 3605 cm$^{-1}$ |
| =C—NH | 3448 cm$^{-1}$ |
| C=O Amide | 1657 cm$^{-1}$ |
| Amide II | 1524 cm$^{-1}$ |
| Aromatic | 1620 cm$^{-1}$ |
|  | 1582 cm$^{-1}$ |
|  | 1498 cm$^{-1}$ |

EXAMPLE 13

N-butyl-3,17β-dihydroxy-N-methyl-11β-Δ$^{1,3,5(10)}$-estratriene-undecanamide

STEP A

N-butyl-3,17β-bis-[(tetrahydro-2H-pyrann-2-yl)-oxo]-11β-Δ$^{1,3,5(10)}$-estratriene-undecanamide A solution of 266 mg of the product of Step B of Example 12, 6.7 ml of sulfuric ether 4.7 ml of dihydropyran and 5 mg of p-toluene sulfonic acid was stirred for 90 minutes and 1 ml of triethylamine was added. The mixture was washed with a sodium bicarbonate solution, then with a saturated sodium chloride solution, dried and evaporated to dryness. The 400 mg of residue were chromatographed on silica (eluant: cyclohexane-ethyl acetate (7-3)) to obtain 286 mg of the desired product.

| IR Spectrum: (CHCl₃) | |
|---|---|
| Absence of OH | |
| Presence of THPO-(aromatic ring) | 1606 cm$^{-1}$ |
|  | 1574 cm$^{-1}$ |
|  | 1497 cm$^{-1}$ |
| NH | 3450 cm$^{-1}$ |
| Amide II | 1518 cm$^{-1}$ |
| C=O | 1660 cm$^{-1}$ |

Step B

N-butyl-3,17β-bis-[(tetrahydro-2H-pyrann-2-yl)-oxy]-N-methyl-11β-Δ$^{1,3,5(10)}$-estratriene-undecanamide 920 mg of the product of Step A with 14 ml of tetrahydrofuran, 2.27 g of tetrabutylammonium bromide, 1.9 g of powdered potassium hydroxide and 14 ml of methyl iodide were stirred for 18 hours at 50° C. under pressure. After refrigeration, the insoluble material was filtered off and washed with 5 changes of 50 ml of tetrahydrofuran. The organic phase was evaporated to dryness under reduced pressure and the 3.4 g of residue were chromatographed on silica (eluant: cyclohexane-ethyl acetate triethylamine (70-30-0.2)) to obtain 850 mg of the desired product used as is for the following step.

| IR Spectrum: (CHCl₃) | |
|---|---|
| No secondary amine | |
| C=O | 1627 cm$^{-1}$ |
| OTHP | Probable |
| Aromatic | 1605 cm$^{-1}$ |
|  | 1572 cm$^{-1}$ |
|  | 1497 cm$^{-1}$ |

Step C

N-butyl-3,17β-dihydroxy-N-methyl-11β-Δ$^{1,3,5(10)}$-estratriene undecanamide 850 mg of the product of Step B, 35 ml of methanol and 3.5 ml of 2N hydrochloric acid were stirred for 1 hour at ambient temperature and the pH was adjusted to 5-6 with 5 ml of concentrated ammonia. The mixture was extracted with methylene chloride, and the organic phase was washed with water, then with a saturated sodium chloride solution, dried and evaporated to dryness under reduced pressure. The 638 mg of residue were chromatographed on silica (eluant: cyclohexane-ethyl acetate (6-4)) to obtain 520 mg of the desired product. A sample of 618 mg of product (98 mg from an earlier preparation was joined to the 520 mg obtained above) was chromatographed on silica (eluant: methylene chloride-acetone (9-1)) to obtain 527 mg of purified product with a specific rotation of $[\alpha]_D = 90.5° \pm 2°$ (c=1% in EtOH).

| Analysis: $C_{34}H_{55}O_3N$; molecular weight = 525.82 | | | |
|---|---|---|---|
| Calculated: | % C 77.67 | %.H 10.54 | % N 2.66 |
| Found: | 77.0 | 10.6 | 2.6 |

| IR Spectrum: (CHCl₃) | |
|---|---|
| Absence of Amide II | |
| HO | 3606 cm$^{-1}$ (+ associated) |
| C=O | 1620 cm$^{-1}$ |
| Aromatic | 1582 cm$^{-1}$ |
|  | 1498 cm$^{-1}$ |

EXAMPLE 14

N-butyl-3,17β-dihydroxy-N-methyl-11β-Δ$^{1,3,5(10)}$-estratriene undecanamide

Step A

17β-acetyloxy-N-butyl-N-methyl-3-oxo-11β-Δ$^{4,9}$-estradiene undecanamide

Using the procedure of Step A of Example 3, 88.5 g of the acid of Step E of Preparaton 5 and 88.5 ml of N-methyl butylamine were reacted to obtain after chromatography on silica (eluant: hexane-ethyl acetate (5-5)) 67.3 g of the desired product.

| IR Spectrum: (CHCl₃) | |
|---|---|
| OAC | 1728 cm$^{-1}$ |
|  | 1255 cm$^{-1}$ |
| Dienone | 864 cm$^{-1}$ |
| Dienone + Amide III | 1628 cm$^{-1}$ |
|  | 1655 cm$^{-1}$ |

Step B 3,17β-bis(acetyloxy)-N-butyl-N-methyl-11β-Δ$^{1,3,5(10)}$-estratriene undecanamide Using the procedure of Step B of Example 3, 67.3 g of the product of Step A were reacted and the dry extract obtained was not chromatographed to obtain 75 g of the desired product used as is for the following step.

Step C

N-butyl-3,17β-dihydroxy-N-methyl-11β-Δ$^{1,3,5(10)}$-estratriene undecanamide 74 g of the product of Step B, 1.850 liters of methanol and 222 ml of methanolic potassium hydroxide at 11 g % ml was stirred for 2 hours at 60° C. and cooled to 0° C. to +5° C. The pH was adjusted to 4–5 by the addition of hydrochloric acid and the methanol was distilled under reduced pressure. The mixture was extracted with methylene chloride and the organic extracts were washed with water, dried and evaporated to dryness under reduced pressure to obtain 65.8 g of resin to which was added 1.7 g made in a previous preparation.

Purfication 67.5 g of crude product were crystallized from 350 ml of ethyl acetate and the mixture was centrifuged at 0° to +5° C. to obtain 45 g of the desired product to which was added 3 g of once-purified product obtained from the mother liquors.

The 48 g of product were crystallized from 4 volumes of ethyl acetate to obtain 46.1 g of the desired product melting at 127° C. and with a specific rotation of $[\alpha]_D = +90.1° \pm 2°$ (c=1% in EtOH).

| Analysis: $C_{34}H_{55}O_3N$; molecular weight = 525.82 | | | |
|---|---|---|---|
| Calculated: | % C 77.67 | % H 10.54 | % N 2.66 |
| Found: | 77.9 | 10.6 | 2.6 |

EXAMPLE 15

17β-hydroxy-N-methyl-N-isoprolyl 3-oxo-11β-Δ$^{4,9}$-estra-diene undecanamide

Step A

N-isopropyl-3,17-dioxo-N-methyl-11β-Δ$^{4,9}$-estradiene undecanamide

Using the procedure of Step A of Example 3, 610 mg of the acid of Preparation 6 and 0.73 ml of N-methyl N-isopropylamine were reacted to obtain after chromatography on silica (eluant: methylene chloride-acetone (9-11)), 455 mg of the desired product.

| IR Spectrum: (CHCl$_3$) | |
|---|---|
| 17 keto | 1736 cm$^{-1}$ |
| Dienone | 1656 cm$^{-1}$ |
| Tertiary Amide | 1621 cm$^{-1}$ |

Step B

17β-hydroxy N-methyl-N-isopropyl 3-oxo-11β-Δ$^{4,9}$ estradiene undecanamide

To a solution of 1.18 g of the product of Step A in 18 ml of tetrahydrofuran, there were added at 0° to −5° C. 707 mg of triterbutoxy aluminium-lithium hydride and the mixture was stirred for 1 hour at 0° to −5° C. and poured into 80 gms of a mixture of equal parts of ice and a saturated ammonium chloride solution. The mixture was stirred for 5 minutes and extracted three times with ethyl acetate. The organic phase was washed with saturated aqueous sodium chloride, dried and evaporated to dryness under reduced pressure. The 1.14 g of residue and 256 mg obtained from a preceding preparation were chromatographed on silica (eluant: methylene chloride-acetone (9-1)) to obtain 640 mg of the desired product with a specific rotation of $[\alpha]_D = -43° \pm 2.5°$ (c=0.4% in ethanol).

| Analysis: $C_{33}H_{53}O_3N$; molecular weight = 511.75 | | | |
|---|---|---|---|
| Calculated: | % C 77.44 | % H 10.44 | % N 2.74 |
| Found: | 77.6 | 10.7 | 2.7 |

| IR Spectrum: (CHCl$_3$) | |
|---|---|
| OH | 3613 cm$^{-1}$ |
| | 1650 cm$^{-1}$ Dienone |
| C=O | 1621 cm$^{-1}$ + Tertiary Amide |

EXAMPLE 16

3,17β-dihydroxy-N-methyl-N-isopropyl-11β-Δ$^{1,3,5(10)}$-estratriene undecanamide

Step A 3-acetyloxy-N-isopropyl-17-oxo-N-methyl-11βΔ$^{1,3,5(10)}$ estratriene undecanamide Using the procedure of Step B of Example 3, 360 mg of the product of Step A of Example 15 were reacted to obtain after chromatography over silica (eluant: methylene chloride-acetone (95-5)) 310 mg of the expected product.

| IR Spectrum: (CHCl$_3$) | |
|---|---|
| Tertiary amide | 1621 cm$^{-1}$ |
| Phenol acetate | 1760 cm$^{-1}$ |
| | 1765 cm$^{-1}$ |
| 17 keto | 1735 cm$^{-1}$ |
| Aromatic | 1493 cm$^{-1}$ |

STEP B

N-isopropyl-3,17β-dihydroxy-N-methyl-11β-Δ$^{1,3,5(10)}$ estratriene undecanamide Using the procedure of Step C of Example 3, 272 mg of the product of Step A were reacted to obtain after chromatography (eluant: methylene chloride-acetone (9-1)), 195 mg of the crude expected product. The said product and 460 mg of product from a previous preparation were purified by passing three times over silica (eluant: acetonitrile) to obtain 460 mg of product which was chromatographed again over silica (eluant: methylene chloride-acetone (9-1)) to obtain 432 mg of the desired product with a specific rotation of $[\alpha]_D = +85°$ C. $\pm 2°$ (c=1% in EtOH).

| Analysis: $C_{33}H_{53}O_3N$; molecular weight = 511.75 | | | |
|---|---|---|---|
| Calculated: | % C 77.44 | % H 10.44 | % N 2.74 |
| Found: | 77.4 | 10.7 | 2.6 |

| IR Spectrum: (CHCl$_3$) | |
|---|---|
| OH | 3606 cm$^{-1}$ + associated |
| C=O | 1618 cm$^{-1}$ |
| | 1583 cm$^{-1}$ |

EXAMPLE 17

N-benzyl-17β-hydroxy-N-methyl-3-oxo-11β-Δ$^{4,9}$-estradiene undecanamide

Step A

N-benzyl-17β-acetoxy-N-methyl-3-oxo-11β-Δ$^{4,9}$-estradiene undecanamide

Using the procedure of Step A of Example 3, 2.1 g of the acid of Step E of Preparation 5 and 2.2 ml of benzyl methylamine were reacted to obtain after chromatography over silica (eluant: cyclohexane-ethyl acetate (1-1)), 1.82 g of the desired product.

| IR Spectrum: (CHCl$_3$) | |
|---|---|
| C=O | 1728 cm$^{-1}$ (OAC) |
| | 1645 cm$^{-1}$ (III amide + Dienone) |
| C=C | 864 cm$^{-1}$ (def.) |
| Aromatic | 1496 cm$^{-1}$ |

Step B

N-benzyl-17β-hydroxy-N-methyl-3-oxo-11β-Δ$^{4,9}$-estradiene undecanamide

Using the procedure of Step B of Example 1, 1 g of the product of Step A were reacted to obtain 670 mg of the desired product.

Analysis: C$_{37}$H$_{53}$O$_3$N; molecular weight = 559.79

| | % C 79.39 | % H 9.54 | % N 2.5 |
|---|---|---|---|
| Calculated: | | | |
| Found: | 79.3 | 9.7 | 2.4 |

| IR Spectrum: (CHCl$_3$) | |
|---|---|
| C=O | 1603 cm$^{-1}$ |
| \C=O/ | 1642 cm$^{-1}$ (dienone + amide III) |
| C=C | 863 cm$^{-1}$ |
| Aromatic | 1496 cm$^{-1}$ |

EXAMPLE 18

N-benzyl-3,17β-dihydroxy-N-methyl-11β-Δ$^{1,3,5(10)}$estratriene undecanamide

Step A 3,17β-diacetyloxy-N-benzyl-N-methyl-11β-Δ$^{1,3,5(10)}$-estratriene undecanamide To a solution of 829 mg of the product of Step A of Example 17 in 8 ml of methylene chloride cooled to 0° to +5° C., 0.6 ml of acetic anhydride and 0.3 ml of acetyl bromide were added and the mixture was stirred for 2 hours, then poured into 60 g of a mixture of ice and a saturated solution of sodium bicarbonate (1-1). The mixture was stirred for 30 minutes and the decanted aqueous phase was extracted with methylene chloride. The organic phase was washed with a saturated solution of sodium chloride, dried and evaporated to dryness under reduced pressure The residue was chromatographed on silica (eluant: cyclohexane-AcOEt (75-25)) to obtain 760 mg of the desired product.

| IR Spectrum: (CHCl$_3$) | |
|---|---|
| Phenol acetate | 1767-1752 cm$^{-1}$ |
| Acetate in position 17 | 1727 cm$^{-1}$ |
| C=O amide III | 1632 cm$^{-1}$ |
| | 1494 cm$^{-1}$ |
| Aromatics | 1585 cm$^{-1}$ |

Step B

N-benzyl-3,17β-dihydroxy-N-methyl-11β-Δ$^{1,3,5(10)}$-estratriene undecanamide 630 mg of the product of Step A, 13 ml of methanol and 910 mg of potassium hydroxide pellets were stirred for 1 hour at ambient temperature and the pH was adjusted to 4–5 by the addition of 2N hydrochloric acid and the mixture was extracted with ethyl acetate. The organic phase was washed with a saturated solution of sodium chloride and evaporated to dryness under reduced pressure. The 555 mg of residue were chromatographed over silica (eluant: methylene chloride-acetone (9-1)) to obtain 390 mg of the desired product with a specific rotation of [α]$_D$=+85.5°±2° (c=0.9% in EtOH).

Analysis: C$_{37}$H$_{53}$O$_3$N; molecular weight = 559.79

| | % C 79.38 | % H 9.54 | % N 2.5 |
|---|---|---|---|
| Calculated: | | | |
| Found: | 79.5 | 9.6 | 2.4 |

| IR Spectrum: (CHCl$_3$) | |
|---|---|
| OH | 3605 cm$^{-1}$ Free and associated |
| C=O Amide III | 1627 cm$^{-1}$ |
| | 1583 cm$^{-1}$ |
| Aromatic | 1497 cm$^{-1}$ |

EXAMPLE 19

N-[2-(dimethylamino)-ethyl]-17β-hydroxy-N-methyl-3-oxo-11β-Δ$^{4,9}$-estradiene undecanamide

Step A

N-[2-dimethylamino)-ethyl]-17β-acetyloxy-N-methyl-3-oxo-11β-Δ$^{4,9}$-estradiene undecanamide Using the procedure of Step A of Example 3, 500 mg of the product of Step E of Preparation 5, 0.5 ml of N-N-N-trimethyl ethylenediamine were reacted to obtain after chromatography over silica (eluant: toluene-triethylamine (8-2)), 380 mg of the desired product.

| IR Spectrum: (CHCl$_3$) | |
|---|---|
| Acetate | 1729 cm$^{-1}$ |
| | 1255 cm$^{-1}$ |
| Dienone + Amide III | 1644 cm$^{-1}$ |
| C=C | 1604 cm$^{-1}$ |
| Bohlmann bands. | |

Step B

N-[2-(dimethylamino)-ethyl]-17β-hydroxy-N-methyl-3-oxo-11β-Δ$^{4,9}$-estradiene undecanamide 800 mg of the product of Step A, 8 ml of methanol and 500 mg of potassium hydroxide pellets were stirred for 1 hour at ambient temperature and the mixture was concentrated to half-volume and a water and ice mixture was added. The mixture was extracted with ethyl acetate and the organic phase was washed with water, then with a saturated solution of sodium chloride, dried and evaporated to dryness under reduced pressure. The 645 mg of residue were chromatographed first over silica (eluant: ethyl acetate-isopropanol-ammonia (80-20-2)), then a second time (eluant: ethyl acetate-triethylamine (6-4)) to obtain 526 mg of the desired product with a specific rotation of $[\alpha]_D = -26° \pm 1.5°$ (c=0.7% in EtOH)

| Analysis: $C_{34}H_{56}O_3N_2$ | | | |
|---|---|---|---|
| Calculated: | % C 75.51 | % H 10.44 | % N 5.18 |
| Found: | 75.3 | 10.6 | 5.2 |
| IR Spectrum: (CHCl$_3$) | | | |

Presence of OH and of Bohlmann band

| | | |
|---|---|---|
| Tertiary amide and N$\langle\begin{smallmatrix}CH_3\\CH_3\end{smallmatrix}$ | | 1642 cm$^{-1}$ |
| C=C | | 1602 cm$^{-1}$ |
| =C—H dif | | 863 cm$^{-1}$ |

EXAMPLE 20

N-[2-(dimethylamino)-ethyl]-3,17β-dihydroxy-N-methyl-11β-$\Delta^{1,3,5(10)}$-estratriene undecanamide

Step A

N-[2-(dimethylamino)-ethyl]-3,17β-diacetyloxy-N-methyl-11β-$\Delta^{1,3,5(10)}$-estratriene undecanamide Using the procedure of Step B of Example 3, 800 mg of the product of Step A of Example 19 were reacted to obtain after chromatography over silica (eluant: toluene-triethylamine (8-2)), 700 mg of the desired product.

| IR Spectrum: (CHCl$_3$) | | |
|---|---|---|
| C=O | Phenolic acetate | 1767-1750 cm$^{-1}$ |
|  | Acetate at 17 | 1727 cm$^{-1}$ |
|  | Tertiary amide | 1630 cm$^{-1}$ |
| Aromatic |  | 1587 cm$^{-1}$ |
| Bohlmann band |  | 1494 cm$^{-1}$ |

Step B

N-[2-(dimethylamino-ethyl]-3,17β-dihydroxy-N-methyl 11β-$\Delta^{1,3,5(10)}$-estratriene undecanamide Using the procedure of Step B of Example 10, 800 mg of the product of Step A were reacted to obtain after chromatography over silica (eluant: toluene-triethylamine (8-2)), 550 mg of product which was chromatographed once more (eluant: ethyl acetate-isopropanol-ammonia (80-2-2)) to obtain 527 mg of the desired product with a specific rotation of $[\alpha]_D = +77.5° \pm 1.5°$ (c=0.9% in EtOH).

| Analysis: $C_{34}H_{56}O_3N_2$; molecular weight = 540.80 | | | |
|---|---|---|---|
| Calculated: | % C 75.51 | % H 10.44 | % N 5.18 |
| Found: | 75.3 | 10.6 | 5.2 |
| IR Spectrum: (CHCl$_3$) | | | |
| OH |  | 3607 cm$^{-1}$ | |
| Amide III |  | 1627 cm$^{-1}$ | |

| | |
|---|---|
| Aromatics | 1582 cm$^{-1}$ |
|  | 1498 cm$^{-1}$ |

EXAMPLE 21

N-butyl-3,17β-dihydroxy-N-methyl-19-nor-11β-$\Delta^{1,3,5(10)}$-pregnatrien-20-yne-undecanamide

Step A

N-butyl-3,17-dioxo-N-methyl-11β-$\Delta^{4,9}$-estradiene undecanamide

Using the procedure of Step A of Example 3, 7.5 g of the acid of Step B of Preparation 6 and 6.4 ml of N-methyl butylamine were reacted to obtain 5.89 g of the desired product.

| IR Spectrum: (CHCl$_3$) | |
|---|---|
| Tertiary amide | 1628 cm$^{-1}$ |

Step B 3-acetyloxy-N-butyl-N-methyl-17-oxo-11β-$\Delta^{1,3,5(10)}$-estratriene undecanamide Using the procedure of Step B of Example 3, 2.63 g of the product of Step A were reacted to obtain 2.91 g of crude product which was used as is in the following step.

| IR Spectrum: (CHCl$_3$) | |
|---|---|
| C=O | 1735 cm$^{-1}$ (17 keto + phenolic OAc) |
| Tertiary amide | 1627 cm$^{-1}$ |
| Aromatic | 1494 cm$^{-1}$ |

Step C

N-butyl-3,17β-dihydroxy-N-methyl-19-nor-11β-$\Delta^{1,3,5(10)}$-pregnatrien-20-yn undecanamide To a solution of 1 g of the product of Step B in 10 ml of ethylenediamine, 1.62 g of lithium acetylide-ethylenediamine complex was added and the mixture was stirred for 4 hours 30 minutes at 50° C., then cooled. 20 g of ice, 10 ml of a saturated solution of ammonium chloride and 30 ml of methylene chloride were added and the mixture was filtered. The aqueous phase was re-extracted with methylene chloride and the combined organic phases were washed with a saturated solution of sodium chloride, dried and evaporated to dryness under reduced pressure, The 0.805 g of residue was chromatographed over silica (eluant: methylene chloride-acetone (9-1)) to obtain 0.58 g of product which was chromatographed again over silica (eluant: methylene chloride-acetone (95-5)) to obtain 0.489 g of the desired product with a specific rotation of $[\alpha]_D = +40.5° \pm 2.5°$ (c=0.5% in EtOH).

| Analysis: $C_{36}H_{55}O_3N$; molecular weight = 549.80 | | | |
|---|---|---|---|
| Calculated: | % C 78.64 | % H 10.08 | % N 2.54 |
| Found: | 78.3 | 10.4 | 2.4 |
| IR Spectrum: CHCl$_3$ (on Nicolet) | | | |

Absence of 17 keto

| | |
|---|---|
| OH | 3599 cm$^{-1}$ + associated |
| C=CH | 3304 cm$^{-1}$ |
| Amide | 1620 cm$^{-1}$ |

EXAMPLE 22

N-butyl-17β-hydroxy-3-oxo-17α-(1-propynyl1)-11β-Δ$^{4,9}$-estradiene undecanamide Using the procedure of Step A of Example 3, 1.37 g of the product of Preparation 7 and 1.4 ml of butylamine were reacted to obtain after chromatography over silica (eluant: cyclohexane-ethyl acetate (5-5)), 744 mg of the desired product.

| Analysis: $C_{35}H_{55}NO_3$; molecular weight = 549.844 | | | |
|---|---|---|---|
| Calculated: | % C 78.64 | % H 10.08 | % N 2.55 |
| (Solvate with 2% ethyl acetate) | 78.15 | 10.46 | 2.49 |
| Found: | 78.2 | 10.4 | 2.4 |
| IR Spectrum: (CHCl$_3$) | | | |
| Secondary amide =C—NH | 3450 cm$^{-1}$ | | |
| Amide II | 1519 cm$^{-1}$ | | |
| C=O | 1657 cm$^{-1}$ + conjugated ketone | | |

EXAMPLE 23

N-butyl-17β-hydroxy-N-methyl-3-oxo-17α-(1-propynyl)-11β-Δ$^{4,9}$-estradiene undecanamide Using the procedure of Step A of Example 3, 962 mg of the acid of Preparation 7 and 1 ml of N-methyl butylamine were reacted to obtain after chromatography over silica (eluant: cyclohexane-ethyl acetate (5-5)), 0.79 g of the desired product.

| Analysis: $C_{37}H_{57}NO_3$; molecular weight = 563.87 | | | |
|---|---|---|---|
| Calculated: | % C 78.81 | % H 10.19 | % N 2.48 |
| Found: | 78.5 | 10.5 | 2.3 |
| IR Spectrum: (CHCl$_3$) | | | |
| Tertiary amide | 1630 cm$^{-1}$ | | |
| OH | 3602 cm$^{-1}$ | | |
| Conjugated ketone | 1643 cm$^{-1}$ with amide III | | |

EXAMPLE 24

N-butyl-3,17β-dihydroxy-N-methyl-11β-Δ$^{1,3,5(10)}$-estratriene dodecanamide

Step A

N-butyl-N-methyl-3,17-dioxo-11β-Δ$^{4,9}$-estradiene dodecanamide

Using the procedure of Step A of Example 1, 1 g of the alcohol of Step B of Preparation 8 and 1.1 ml of N-methyl-butylamine were reacted to obtain after chromatography over silica (eluant: ethyl acetate-cyclohexane (8-2)), 717 mg of the desired product.

| IR Spectrum: (CHCl$_3$) | | |
|---|---|---|
| Little or no OH | | |
| C=O (17 keto) | | 1735 cm$^{-1}$ |
| C=O | Conjugated ketone | 1655 cm$^{-1}$ |
| | | 1643 cm$^{-1}$ |
| | Tertiary amide | 1628 cm$^{-1}$ |
| —C=C | (ep.) | 1603 cm$^{-1}$ |

Step B

N-butyl-N-methyl-17β-hydroxy-11β-Δ$^{4,9}$-estradiene dodecanamide

To a solution of 837 mg of the product of Step A in 17 ml of tetrahydrofuran at 0° C., 494 mg of aluminium lithium tri-terbutoxy hydride were added for 20 minutes at 0° C. 20 ml of a saturated solution of ammonium chloride were added and the mixture was extracted with ethyl acetate and with methylene chloride. The organic phase was evaporated to dryness under mixture was extracted with ethyl acetate and with methylene chloride. The organic phase was evaporated to dryness under reduced pressure and the 836 mg of residue were chromatographed over silica (eluant: ethyl acetate-cyclohexane (6-4)) to obtain 604 mg of the expected product.

| IR Spectrum: (CHCl$_3$) | | |
|---|---|---|
| OH | 3612 cm$^{-1}$ | |
| C=O | 1642 cm$^{-1}$ (ep.) | } Possibly encompassing dienone + tertiary amide |
| Complex | 1628 cm$^{-1}$ (max) | |
| Intense aliphatics | | |

Step C

N-butyl-3,17β-dihydroxy-N-methyl-11β-Δ$^{1,3,5(10)}$-estratriene dodecanamide

To a solution cooled to 0° C. of 0.2 g of the product of Step B in 2.6 ml of methylene chloride, 0.26 ml of acetic anhydride and 0.13 ml of acetyl bromide were added at 0° C. and was allowed to recover to ambient temperature. After 1 hour, 20 ml of sodium bicarbonate in saturated solution were added and the mixture was stirred for 30 minutes and extracted with methylene chloride. The organic phase was evaporated to dryness under reduced pressure and the 250 mg of residue were taken up in 10 ml of methanol. 150 mg of potassium hydroxide pellets were added to the solution which was heated for 2 hours at 40° C., then cooled to 0° C. The mixture was neutralized with concentrated hydrochloric acid and extracted with methylene chloride. The organic phase was evaporated to dryness under reduced pressure and the 188 mg of residue were chromatographed over silica (eluant: cyclohexane-ethyl acetate (6-4)) to obtain 131 mg of the expected product with a specific rotation of $[\alpha]_D = +89°\pm3°$ (c=0.6% in EtOH).

| Analysis: $C_{35}H_{57}NO_3$ | | | |
|---|---|---|---|
| Calculated: | % C 77.87 | % H 10.64 | % N 2.59 |
| Found: | 77.8 | 10.5 | 2.5 |
| IR Spectrum: (CHCl$_3$) | | | |
| OH | 3606 cm$^{-1}$ + associated | | |
| C=O | 1620 cm$^{-1}$ | | |
| Aromatic | 1582 cm$^{-1}$ | | |
| | 1498 cm$^{-1}$ | | |

EXAMPLE 25

1-[11-(17β-hydroxy-3-oxo-Δ$^{4,9}$-estradien-11β-yl)-1-oxo-undecyl]-pyrrolidine

Step A

1-[11-(17β-acetyloxy-3-oxo-Δ$^{4,9}$-estradien-11β-yl)-1-oxo-undecyl]-pyrrolidine Using the procedure of Step A of Example 3, 2.76 g of the acid of Step E of Preparation 5 and 2.5 ml of pyrrolidine were reacted to obtain after chromatography over silica (eluant: cyclohexane-ethyl acetate (4-6)), 2.18 g of the desired product.

| IR Spectrum: (CHCl$_3$) | | |
|---|---|---|
| Little or no acid | | |
| C=O | 1728 cm$^{-1}$ | OAC |
| | 1650 cm$^{-1}$ | Dienone + |
| | 1622 cm$^{-1}$ | tertiary amide |

Step B

1-[11-(17β-hydroxy-3-oxo-Δ$^{4,9}$-estradien-11β-yl)-1-oxo-undecyl]-pyrrolidine

For 40 minutes, a solution of 1.265 g of the product of Step A in 10 ml of N ethanolic potassium hydroxide was stirred and 12 ml of N hydrochloric acid and then 2 ml of concentrated ammonia were added. The mixture was extracted with ethyl acetate, washed with water, dried and evaporated to dryness. The 1.164 g of residue were chromatographed over silica (eluant: ethyl acetate-cyclohexane (8-2)) to obtain 988 mg of the desired product.

| Analysis: C$_{33}$H$_{51}$O$_3$N; molecular weight = 509.78 | | | |
|---|---|---|---|
| Calculated: | % C 77.75 | % H 10.08 | % N 2.74 |
| Found: | 77.4 | 10.4 | 2.7 |

| IR Spectrum: (CHCl$_3$) | |
|---|---|
| OH + associated | 3614 cm$^{-1}$ |
| C=O conjugated | 1643 cm$^{-1}$ |
| Tertiary amide | 1623 cm$^{-1}$ |

EXAMPLE 26

1-[11-(3,17β-dihydroxy-Δ$^{1,3,5(10)}$-estratrien-11β-yl)-1-oxo-undecyl]-pyrrolidine 773 mg of the product of Step A of Example 25 dissolved in 8 ml of methylene chloride at 0° C. to +5° C. were admixed with 0.4 ml of acetyl bromide and 0.8 ml of acetic anhydride and the mixture was stirred for 2 hours while allowing the temperature rise to ambient temperature. After adding ice and neutralizing by addition of sodium bicarbonate, the mixture was washed with water, dried and evaporated to dryness under vacuum to obtain 829 mg of the intermediate diacetate.

The 829 mg of product were reacted as in Step B of Example 25 and after chromatography over silica (eluant: ethyl acetate alone, then ethyl acetate with 20% methanol); 545 mg of the expected crude product were obtained which were crystallized from a methylene chloride-isopropyl ether mixture, then from ethyl acetate to obtain 396 mg of the desired product melting at 150° C. and having a specific rotation of [α]$_D$ = +70°±2.5° (c=0.5% in CHCl$_3$).

| IR Spectrum: (CHCl$_3$) | |
|---|---|
| OH free + associated | 3607 cm$^{-1}$ |
| C=O | 1617 cm$^{-1}$ |
| Aromatics | 1582 cm$^{-1}$ |
| | 1498 cm$^{-1}$ |

PREPARATION OF EXAMPLE 27

11β-[4-(8-hydroxyoctyl)-phenyl]-Δ$^{4,9}$-estradien-3,17-dione

Using the procedure of Step A of preparation 6, 8.5 g of the product of Step A of preparation 4 were reacted to obtain after chromatography on silica (elution with methylene chloride-acetone 9-1), 5.65 g of the desired product.

| IR Spectrum: (CHCl$_3$) | |
|---|---|
| —OH | 3623 cm$^{-1}$ |
| 17 keto | 1733 cm$^{-1}$ |
| non conjugated ketone | 1712 cm$^{-1}$ |
| aromatic | 1605 cm$^{-1}$ |
| | 1506 cm$^{-1}$ |

EXAMPLE 27

4-[3-hydroxy-17-oxo-Δ$^{1,3,5(10)}$-estratrien-11β-yl-N-methyl-N-isoproply-benzene]-octanamide

Step A 4-(3,17-dioxo-Δ$^{4,9}$-estradien-11β-yl)-N-methyl-N-isopropyl-benzene octanamide Using the procedure of Example 1, 7.05 g of the product of preparation 14 and 7.9 ml of N-methyl-isopropylamine for the amidification were reacted, and after chromatography on silica (eluant: methylene chloride-acetone 9-1) obtained 5.99 g of the expected product.

| IR Spectrum: (CHCl$_3$) | |
|---|---|
| amide III | 1621 cm$^{-1}$ |
| 17-keto | 1735 cm$^{-1}$ |
| dienone | 1657 cm$^{-1}$ |
| Aromatics | 1510 cm$^{-1}$ |

Step B 4-(3-acetyloxy-17-oxo-Δ$^{1,3,5(10)}$-estratrien-11β-yl)-N-methyl-N-isopropyl-benzene octanamide Using the procedure of Step B of Example 3, 4 g of the product of Step A and 1.9 ml of acetyl bromide and 3.8 ml of acetic anhydride were reacted to obtain after chromatography on silica (eluant: cyclohexane-ethyl acetate 1-1), 4.2 g of the expected product.

| IR Spectrum: (CHCl$_3$) | |
|---|---|
| Absence of dienone | - |
| Phenolic acetate | 1755 cm$^{-1}$ (ep.) |
| 17-keto | 1731 cm$^{-1}$ |
| amide III | 1621 cm$^{-1}$ |
| Aromatic | 1513 cm$^{-1}$ |
| | 1493 cm$^{-1}$ |

Step C

4-(3-hydroxy-17-oxo-Δ$^{1,3,5(10)}$-estratrien-11β-yl)-N-methyl-N-isopropyl-benzene octanamide Using the procedure of Example 2, 2.3 g of the product of Step B were reacted to obtain after chromatography on silica (eluant: cyclohexane-ethyl acetate 1-1) 2 g of the desired product with a specific rotation of [α]$_D$= −16°±2° (c=0.5% in ethanol).

| IR Spectrum: (CHCl$_3$) | |
|---|---|
| OH | 3600 cm$^{-1}$ |
| 17-keto | 1732 cm$^{-1}$ |
| amide III | 1617 cm$^{-1}$ |
| Aromatics | 1583 cm$^{-1}$ |
|  | 1510 cm$^{-1}$ |
|  | 1501 cm$^{-1}$ |

EXAMPLE 28

4-[3,17β-dihydroxy-Δ$^{1,3,5(10)}$-estratrien-11β-yl]-N-methyl-N-isopropyl-benzene octanamide To a solution of 480 mg of the product of Example 27 and 7.5 ml of anhydrous tetrahydrofuran, there were added at 0° C./+5° C. 563 mg of triterbutoxy lithium aluminium hydride. The mixture was stirred for 50 minutes and 100 mg of the hydride were added. The solution was poured into a 1-1 mixture of ice and of a saturated solution of ammonium chloride and extracted with ethyl acetate. The organic phase was washed with a saturated solution of sodium chloride, dried, filtered and evaporated to dryness. After chromatography on silica (eluant: cyclohexane-ethyl acetate 1-1), 472 mg of desired product with a specific rotation of [α]$_D$= −34.5°±2.5° (c=0.5% in ethanol) were obtained.

| IR Spectrum: (CHCl$_3$) | |
|---|---|
| OH | 3605 cm$^{-1}$ |
| amide III | 1617 cm$^{-1}$ |
| Aromatics | 1583 cm$^{-1}$ |
|  | 1499 cm$^{-1}$ |

EXAMPLE 29

4-[3,17β-dihydroxy-19-nor-17α-Δ$^{1,3,5(10)}$-pregnatrien-20-yn-11β-yl]-N-methyl-N-isopropyl benzene octanamide To a solution of 400 mg of the product of Example 27 in 20 ml of tetrahydrofuran, there were added over 3 hours 30 minutes 825 mg of lithium ethylene diamine acetylide and the mixture was stirred for 4 hours and poured into a 1-1 mixture of ice and a saturated solution of ammonium chloride. The mixture was extracted with ethyl acetate, washed with water saturated with sodium chloride, dried, filtered and evaporated to dryness. The residue was chromatographed on silica twice, each time using eluant: methylene chloride-acetone 93-7, to obtain 115 mg of the desired product with a specific rotation of [α]$_D$= −105°±2° (c=0.9% in ethanol).

| IR Spectrum: (CHCl$_3$) | |
|---|---|
| OH | 3599 cm$^{-1}$ |
| C≡CH | 3304 cm$^{-1}$ |
| amide III | 1617 cm$^{-1}$ |
| Aromatics | 1583 cm$^{-1}$ |
|  | 1500 cm$^{-1}$ |

EXAMPLE 30

4-[3,17β-dihydroxy-17α-methyl-Δ$^{1,3,5(10)}$-estratrien-11β-yl]-N-methyl-N-isopropyl benzene octanamide To a solution of 700 mg of the product of Example 27 in 35 ml of tetrahydrofuran, there were added at 20°/25° C. 12.8 ml of a 0.76M solution of methyl magnesium bromide in tetrahydrofuran. After one hour of reaction, the solution was poured into a 1-1 mixture of ice and of a saturated solution of ammonium chloride and was extracted with ethyl acetate. The extracts were washed with a saturated solution of sodium chloride, dried, filtered and evaporated to dryness. The residue was chromatographed on silica (eluant: methylene chloride-acetone 9-1) to obtain 411 mg of the desired product.

| Analysis: C$_{37}$H$_{53}$NO$_3$; molecular weight = 559.84 | | | |
|---|---|---|---|
| Calculated: | % C 79.38 | % H 9.54 | % N 2.50 |
| Found: | 79.4 | 9.5 | 2.4 |

PREPARATION A OF EXAMPLE 31

4-trimethylsilylethynyl bromo benzene

A mixture of 150 g of 97% bromo iodo benzene, 500 ml of anhydrous dimethylformamide, 100 ml of triethylamine, 50 g of trimethylsilyl acetylene, 2.1 g of copper iodide and 2.22 g of bis-(triphenylphosphine)-palladium (II) dichloride was stirred for 2 hours and then 500 ml of ice-cooled water were added. The mixture was extracted 3 times with 500 ml of ethyl acetate and the organic phase was washed with salt water, then dried over sodium sulfate, and evaporated under reduced pressure to obtain 136.542 g of a brown oil which was purified by distillation under reduced pressure to obtain 106.979 g of the expected product with a boiling point of 75°–82° C. under 0.2 mbar and a melting point of 62° C.

| IR Spectrum: (CHCl$_3$) | |
|---|---|
| Absence of C≡CH | |
| C=C | 2160 cm$^{-1}$ |

PREPARATION B OF EXAMPLE 31

Step A

3-(1,2-ethanediyl cyclic acetal)-5α-hydroxy-11β-[[4-(1,1-dimethylethyl)-dimethylsilyl]-ethynyl-phenyl]-Δ$^9$-estren 3,17-dione Using the procedure of Step A of preparation 1, 30 g of 3-(1,2-ethanediyl cyclic acetal) of 5α,10α-epoxy-Δ$^9$-estren-3,17-dione of EP Patent No. 0,057,115 (Example 7) using, for the preparation of the magnesium compound, 81.254 g of the brominated derivative of preparation A, and 7.96 g of magnesium, then for the condensation, 1.4 g of copper chloride were reacted and after chromatography on silica, the crude product obtained and the product of an operation carried out in the same way starting with 16.52 g of epoxide (eluant: methylene chloride-acetone 98-2) were reacted to obtain 50.8 g of pure product A and 6 g of slightly less pure product B which were used as they are for the following step.

| IR Spectrum: (CHCl$_3$) | |
|---|---|
| OH | 3508 cm$^{-1}$ |
| C≡C | 2156 cm$^{-1}$ |
| Aromatics | 1602 cm$^{-1}$ |
| | 1555 cm$^{-1}$ |
| | 1502 cm$^{-1}$ |

Step B

11β-(4-ethynylphenyl)-Δ$^{4,9}$-estradien-3,17-dione

A suspension of 46.8 g of the product of Step A, 200 ml of ethanol and 8.1 ml of sodium hydroxide was stirred for 30 minutes and 16.7 ml of concentrated hydrochloric acid were added. The mixture was stirred at ambient temperature and then concentrated to half the volume and extracted with methylene chloride. The organic phase was dried and evaporated under reduced pressure. The 38.23 g of residue were chromatographed on silica (eluant: cyclohexane-ethyl acetate 1-1) to obtain 31.06 g of the desired product melting at 184° C.

| IR Spectrum: (CHCl$_3$) | |
|---|---|
| C≡CH | 3302 cm$^{-1}$ |
| C=O | 1736 cm$^{-1}$ (17-keto) |
| | 1659 cm$^{-1}$ |
| | 1640 cm$^{-1}$ dienone |
| Aromatic | 1556, 1506 cm$^{-1}$ |

Step C

3β-hydroxy-11β-(4-ethynyl phenyl)-Δ$^{1,3,5(10)}$-estratrien-17-one

Acetylation at Position 3

Using the procedure of Step B of Example 3, 31 g of the compound of Step B and 47.1 ml of acetic anhydride and 23.8 ml of acetyl bromide were reacted to obtain 31.2 g of 3-acetate which was saponified by using the procedure of Step B of Example 1. After chromatography on silica (eluant: cyclohexane-ethyl acetate 7-3), 27.03 g of crude product were obtained and made into a paste in ether to collect 22.852 g of the desired product melting at 163° C.

| IR Spectrum: (CHCl$_3$) | |
|---|---|
| OH | 3597 cm$^{-1}$ |
| C≡CH | 3303 cm$^{-1}$ |
| C=O | 1733 cm$^{-1}$ |
| Aromatic | 1606, 1582, 1556, 1503 cm$^{-1}$ |

Step D 3,17β-tetrahydropyrannyloxy-11β-(4-ethynylphenyl)-Δ$^{1,3,5(10)}$-estratriene a) Reduction of the 17-ketone Using the procedure of Step B of Example 3, 14 g of the compound of Step C and 10 g of sodium borohydride were reacted.

b) Dihydropyranylation

Using the procedure of Step A of Example 39, 17.3 g of the 17-hydroxy intermediate obtained above and 24.4 ml of dihydropyran and 0.3 g of p-toluene sulfonic acid were reacted to obtain after chromatography on silica, 13.6 g of crude product which was taken up in isopropyl ether to collect 10.23 g of the desired product melting at 213° to 215° C.

| IR Spectrum: (CHCl$_3$) | |
|---|---|
| C≡CH | 3302 cm$^{-1}$ |
| Aromatic | 1607, 1570, 1556, 1498 cm$^{-1}$ |

PREPARATION C OF EXAMPLE 31

1-oxo-6-bromo hexyl morpholine

Using the procedure of Step A of Example 3, 5 g of 6-bromo-benzylic acid and 3.4 ml of N-methyl morpholine, 3.7 ml of isobutyl chloroformate and 3.35 ml of morpholine were reacted to obtain after chromatography on silica (eluant: methylene chloride-acetone 9-1), 7 g of the desired product which was used as is for the following step.

| IR Spectrum: (CHCl$_3$) | |
|---|---|
| C=O | 1635 cm$^{-1}$ |
| | 1115 cm$^{-1}$ |

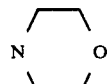

EXAMPLE 31

4-(8-(4-(3,17β-dihydroxy-Δ$^{1,3,5(10)}$-estratrien-11β-yl)-phenyl-1-oxo-7-octynyl)-morpholine To a solution cooled to −30° C. of 800 mg of the compound of Preparation B of Example 31 in 6.5 ml of tetrahydrofuran and 6.5 ml of hexamethylphosphotriamide, 1.7 ml of a 1.1M solution of butyllithium in hexane were added dropwise and after stirring for 5 minutes at −30° C., 508 mg of 1-oxo-6-bromo hexyl morpholine of Preparation C above in solution in 1 ml of tetrahydrofuran at −25° to −30° C. were added. The mixture was stirred for one hour and poured into 30 ml of a sodium chloride solution. The mixture was extracted with ethyl acetate and the extracts were washed, dried and evaporated to dryness under reduced pressure and the 3 g of crude product were chromatographed on silica (eluant: cyclohexane-ethyl acetate 1-1) to obtain 760 mg of the product which was depyranylised for one hour at ambient temperature with a mixture of 8 ml of 2N hydrochloric acid and 40 ml of methanol. The mixture was poured into 50 g of water and ice (1-1), extracted with methylene chloride, and evaporated to dryness under reduced pressure. The 665 mg of residue were chromatographed on silica (eluant: methylene chloride-acetone 8-2) to obtain 502 mg of the desired product which after crystallization from ether had a specific rotation of [α]$_D$= −36.5°±2.5° (c=1% in ethanol).

| IR Spectrum: (CHCl$_3$) | |
|---|---|
| OH | 3603 cm$^{-1}$ |

| | | |
|---|---|---|
| C═O | 1631 cm$^{-1}$ | |
| Aromatic | 1584, 1550, 1505 cm$^{-1}$ | |
| Morpholine | 1115 cm$^{-1}$ | |

Analysis: C$_{36}$H$_{45}$NO$_4$; molecular weight = 555.76
Calculated: % C 77.80   % H 8.16   % N 2.52
Found:            77.8              8.3            2.5

EXAMPLE 32

4-[8-(4-(3,17β-dihydroxy-Δ$^{1,3,5(10)}$-estratrien-11β-yl)-phenyl]-1-oxo octyl)-morpholine To a solution of 290 mg of the product of Example 31 in 15 ml of ethanol, there were added 145 mg of palladium on 10% activated carbon, and hydrogenation was effected under 1300 mbar. The mixture was filtered and the filtrate was evaporated to dryness. The 280 mg of residue were chromatographed on silica (eluant: methylene chloride-acetone 85-15) and taken up in ether to obtain 256 mg of the desired product with a specific rotation of [α]$_D$= −30°±2.5° (c=0.5% in ethanol).

| IR Spectrum: (CHCl$_3$) | |
|---|---|
| OH | 3604 cm$^{-1}$ |
| C═O | 1629 cm$^{-1}$ |
| Aromatic | 1583, 1500 cm$^{-1}$ |
| Morpholine | 1115 cm$^{-1}$ |

Analysis: C$_{36}$H$_{49}$NO$_4$; molecular weight = 559.8
Calculated: % C 77.24   % H 8.82   % N 2.56
Found:            77.5              9.1            2.5

PREPARATION OF EXAMPLE 33

N-dibutyl-6-bromohexanamide

Using the procedure of Step A of Example 3, 4.41 g of 5-bromohexanoic acid and 11.1 g of dibutylamine were reacted to obtain the desired product which after distillation under reduced pressure resulted in 6.141 g of the expected product with a boiling point of 139° C. under 0.5 mbar.

| IR Spectrum: (CHCl$_3$) | |
|---|---|
| C═O | 1623 cm$^{-1}$ (amide III) |

EXAMPLE 33

8-(4-(3,17β-dihydroxy-Δ$^{1,3,5(10)}$-estratrien-11β-yl)-phenyl)-N,N-dibutyl-7-octynamide Using the procedure of Example 31, 0.7 of the compound of Preparation 33 and 0.463 mg of bromo-dibutyl-7-octynamide (Preparation of Example 33) were reacted to obtain after chromatography on silica (eluant: cyclohexane-ethyl acetate 1-1), 657 mg of the expected product with a specific rotation of [α]$_D$= −26°±2° (c=0.5% in ethanol).

| IR Spectrum: (CHCl$_3$) | |
|---|---|
| OH | 3603 cm$^{-1}$ |
| C═O | 1621 cm$^{-1}$ |
| Aromatic | 1582 cm$^{-1}$ |

Analysis: C$_{40}$H$_{55}$NO$_3$; molecular weight = 597.89
Calculated: % C 79.82   % H 9.88   % N 2.33
Found:            79.7              10.1          2.4

EXAMPLE 34

8-(4-(3,17β-dihydroxy-Δ$^{1,3,5(10)}$-estratrien-11β-yl)-phenyl)-N,N-dibutyl-7-octanamide Using the procedure of Example 32, 381 mg of the product of Example 33 and 0.1 g of palladium on activated carbon were reacted to obtain after chromatography on silica (eluant: cyclohexane-ethyl acetate 1-1), 241 mg of the desired product with a specific rotation of [α]$_D$= −26°±2° (c=0.5% in ethanol).

| IR Spectrum: (CHCl$_3$) | |
|---|---|
| OH | 3605 cm$^{-1}$ |
| C═O | 1619 cm$^{-1}$ |
| Aromatic | 1583, 1500 cm$^{-1}$ |

Analysis: C$_{40}$H$_{59}$NO$_3$; molecular weight = 602.92
Calculated: % C 79.82   % H 9.88   % N 2.33
Found:            79.7              10.1          2.4

PREPARATION OF EXAMPLE 35

N-methyl-N-butyl-1-iodo-hexanamide

To a solution of 5.288 g of N-methyl-N-butyl-1-bromo hexanamide (Preparation of Example 33) in 105 ml of acetone, there were added 4.497 g of sodium iodide and the mixture was stirred for 18 hours, then filtered and diluted with water. The mixture was extracted with ethyl acetate and the organic phase was washed, dried and evaporated to dryness under vacuum to obtain 6.139 g of the expected product.

EXAMPLE 35

8-(4-3,17β-dihydroxy-Δ$^{1,3,5(10)}$-estratrien-11β-yl)-phenyl)-N-butyl-N-methyl-7-octynamide Using the procedure of example 33, 692 mg of the product of Preparation 33 and 516 mg of N-methyl-N-butyl-1-iodo-hexanamide (Preparation of Example 35) were reacted to obtain after chromatography on silica (eluant: cyclohexane-ethyl acetate 2-8) to obtain 586 mg of the expected product with a specific rotation of [α]$_D$= −35.5°±2.5° (c=0.5% in ethanol).

| IR Spectrum: (CHCl$_3$) | |
|---|---|
| OH | 3605 cm$^{-1}$ |
| C═O | 1621 cm$^{-1}$ |
| C═C + Aromatic | 1583, 1500 cm$^{-1}$ |

Analysis: C$_{37}$H$_{49}$NO$_3$; molecular weight = 557.81
Calculated: % C 79.95   % H 8.88   % N 2.51
Found:            79.8              9.0            2.5

EXAMPLE 36

(Z) 8-(4-(3,17β-dihydroxy-Δ1,3,5(10)-estratrien-11β-yl)-phenyl-N-methyl-7-octenamide To a solution of 555 mg of the product of Example 35 in 11 ml of ethyl acetate, 50 mg of palladium on barium sulfate and 0.22 ml of pyridine were added and hydrogenation was effected under a pressure of 1500 mbars. The mixture was filtered and evaporated to dryness under reduced pressure to obtain 620 mg of residue which was chromatographed on silica (eluant: cyclohexane-ethyl acetate 1-1) to obtain 360 mg of the desired product which was chromatographed a second time under these conditions to obtain 344 mg of the pure compound with a specific rotation of $[\alpha]_D = -32° \pm 2.5°$ (c=0.5% in ethanol).

| IR Spectrum: (CHCl₃) | |
|---|---|
| —OH | 3605 cm$^{-1}$ |
| C=O | 1621 cm$^{-1}$ |
| C=C + Aromatic | 1583, 1500 cm$^{-1}$ |

| Analysis: | C₃₇H₅₁NO₃; molecular weight = 557.82 | | | | | |
|---|---|---|---|---|---|---|
| Calculated: | % C | 79.66 | % H | 9.21 | % N | 2.5 |
| Found: | | 79.5 | | 9.4 | | 2.4 |

EXAMPLE 37

2-((7-(4-(3,17β-dihydroxy-Δ$^{1,3,5(10)}$-estratrien-11β-yl)-phenyl-6-heptynyl)-oxy)-N-butyl-N-methyl acetamide Using the procedure of Example 33, 0.7 g of the compound of Preparation B of Example 31 and 0.493 g of [(5-bromopentyl)-oxy]-N-butyl-N-methyl acetamide (Preparation 21) were reacted to obtain after chromatography on silica (eluant: ethyl acetate-cyclohexane 8-2), 460 mg of the desired product.

| IR Spectrum: (CHCl₃) | |
|---|---|
| OH | 3603 cm$^{-1}$ + associated |
| C=O | 1634 cm$^{-1}$ |
| Aromatic | 1584, 1554, 1505 cm$^{-1}$ |

| Analysis: | C₃₈H₅₁NO₄; molecular weight = 585.829 | | | | | |
|---|---|---|---|---|---|---|
| Calculated: | % C | 77.91 | % H | 8.78 | % N | 2.39 |
| Found: | | 78.2 | | 8.9 | | 2.5 |

EXAMPLE 38

2-((7-(4-(3,17β-dihydroxy-Δ$^{1,3,5(10)}$-estratrien-11β-yl)-phenyl)-heptyl)-oxy)-N-butyl-N-methyl acetamide Using the procedure of Example 34, 300 mg of the product of Example 37 and 0.1 g of palladium on activated carbon were reacted to obtain after chromatography on silica (eluant: cyclohexane-ethyl acetate 1-1), 201 mg of the desired product with a specific rotation of $[\alpha]_D = -19° \pm 1°$ (c=1% in ethanol).

| IR Spectrum: (CHCl₃) | |
|---|---|
| —OH | 3604 cm$^{-1}$ |
| C=O | 1635 cm$^{-1}$ |
| Aromatic | 1583, 1500 cm$^{-1}$ |

| Analysis: | C₃₈H₅₅NO₄ | | | | | |
|---|---|---|---|---|---|---|
| Calculated: | % C | 77.38 | % H | 9.40 | % N | 2.37 |
| Found: | | 77.2 | | 9.7 | | 2.4 |

EXAMPLE 39

N-butyl-4-[3,17β-dihydroxy-Δ$^{1,3,5(10)}$-estratrien-11β-yl]-α,α-N-trimethyl benzene octanamide

Step A

N-butyl-N-methyl-4-[3,17β-bis-[(tetrahydro-2H-pyran-2-yl)-oxy]-Δ$^{1,3,5(10)}$-estratrien-11β-yl]-benzene octanamide A mixture of 500 mg of the product of Example 8, 20 ml of ether, 15 ml of dihydropyran and 15 mg of p-toluene sulfonic acid was stirred for 150 minutes and then 1 ml of triethylamine was added. The mixture was poured into a 1-1 mixture of ice and saturated solution of sodium bicarbonate and extracted with ether. The organic phase was filtered and evaporated to dryness and the residue was chromatographed on silica (eluant: cyclohexane-ethyl acetate 1-1) to obtain 640 mg of the desired product.

| IR Spectrum: (CHCl₃) | |
|---|---|
| Absence of OH, presence of tetrahydropyranyl ether | |
| amide III | 1627 cm$^{-1}$ |
| Aromatics | 1574 cm$^{-1}$ |
| | 1510 cm$^{-1}$ |
| | 1497 cm$^{-1}$ |

Step B

N-butyl-α-N-dimethyl-4-[3,17β-bis-[(tetrahydro-2H-pyran-2-yl)-oxy-Δ$^{1,3,5(10)}$-estratrien-11β-yl]-benzene octanamide To a solution of 0.7 ml of diisopropylamine in 5 ml of anhydrous tetrahydrofuran, there were added at 5° to 8° C. 2.8 ml of a 1.6M solution of butyllithium in hexane and the mixture was stirred for 10 minutes at +5° C., then cooled to −70° C. and a solution of 630 mg of the product of Step A in 5 ml of anhydrous tetrahydrofuran was added. The mixture was stirred for 30 minutes at −70° C. and after 0.5 ml of methyl iodide were added, the mixture was stirred for 45 minutes. 20 ml of a saturated solution of ammonium chloride were added and the mixture returned to ambient temperature. The mixture was extracted with ethyl acetate, and the organic phase was washed, dried and evaporated to dryness. The residue was chromatographed on silica (eluant: cyclohexane-ethyl acetate 8-2) to obtain 567 mg of the desired product which was used as is for the following step.

NMR Spectrum 300 MHz: -methyl of the amine: 1.07 (d) and 1.08 (d).

Step C

N-butyl-4-[3,17β-dihydroxy-Δ$^{1,3,5(10)}$-estratrien-11β-yl]-α,α-N-trimethyl benzene octanamide a) Dimethylation To a solution of 516 mg of the product of Step B in 11.5 ml of tetrahydrofuran, there were added at 48° C.±2° C. 9 ml of a solution of lithium diisopropylamide (prepared at +5°/+8° C. by addition of 6.2 ml of a 1.6M solution of butyllithium in hexane to a solution of 1.4 ml of diisopropylamine in 10 ml of tetrahydrofuran). Once the addition of the lithium diisopropylamine was complete, the mixture was stirred for 15 minutes and 1.2 ml of methyl iodide were added in one lot. The resulting medium was stirred for 45 minutes and then poured into 50 g of a 1-1 mixture of ice and saturated solution of ammonium chloride. The mixture was extracted with ethyl acetate and the organic phase was washed, dried and evaporated to dryness to obtain 560 mg of intermediate N-butyl-α,α-N-trimethyl-4-[3,17β-bis-(tetrahydro-2H-pyran-2-yl)-oxy]-Δ$^{1,3,5(10)}$-estratrien-11β-yl]-benzene octanamide which was used as is for the depyranylation.

b) Depyranylation

The dry extract obtained above was dissolved in 15 ml of methanol and 2 ml of 2N hydrochloride acid were added. The mixture was stirred for one hour at ambient temperature and poured into a saturated solution of sodium chloride. The mixture was extracted with methylene chloride and the organic phase was dried and evaporated to dryness, and the 465 mg of residue were chromatographed on silica (eluant:methylene chloride-acetone 95-5) to obtain after trituration in ether, 207 mg of the desired product with a specific rotation of $[\alpha]_D = -30°$ C. $\pm 2.5°$ (c=0.5% in ethanol).

| Analysis: | $C_{39}H_{57}NO_3$; molecular weight = 587.85 | | | | | |
|---|---|---|---|---|---|---|
| Calculated: | % C | 79.68 | % H | 9.77 | % N | 2.38 |
| Found: | | 79.8 | | 9.9 | | 2.5 |

PREPARATION OF EXAMPLE 40

4-(3,7-dioxo-$\Delta^{4,9}$-estradien-11$\beta$-yl)-benzene octanol

Using the procedure of Preparation 6A, 3.6 g of the product of Preparation 4A were reacted to obtain after chromatography on silica (eluant: methylene chloride-acetone 95-5), 2.234 g of the expected product.

| IR Spectrum: (CHCl$_3$) | |
|---|---|
| OH | 3623 cm$^{-1}$ |
| C=O | 1735 cm$^{-1}$ |
| Dienone | 1658, 1602 cm$^{-1}$ |
| Aromatic | 1570 (ep.), 1510 cm$^{-1}$ |

EXAMPLE 40

4-[3,17$\beta$-dihydroxy-$\Delta^{1,3,5(10)}$-estratrien-11$\beta$-yl]-N-methyl-N-isopropyl benzene nonamide

Step A 4-(3,17-dioxo-$\Delta^{4,9}$-estradien-11$\beta$-yl)-benzene octane methane sulfonate To a solution of 2.234 g of the product of the Preparation of Example 40 in 20 ml of anhydrous pyridine, there were added 3.36 g of p-toluene sulfonyl chloride and the mixture was stirred for 80 minutes. 30 ml of a saturated solution of sodium bicarbonate were added and the mixture was stirred for 30 minutes and extracted with methylene chloride. The solvents were dried, then evaporated to dryness under reduced pressure. The 2.9 g of residue were chromatographed on silica (eluant: methylene chloride-acetone 9-1) to obtain 2.255 g of the desired product.

| IR Spectrum: (CHCl$_3$) | |
|---|---|
| C=O (17-keto) | 1735 cm$^{-1}$ |
| Dienone | 1658, 1600 cm$^{-1}$ |
| Aromatic | 1510, 1496 cm$^{-1}$ |
| SO$_2$ | 1359, 1496, 1176 cm$^{-1}$ |

Step B 4-(3,17-dioxo-$\Delta^{4,9}$-estradien-11$\beta$-yl)-benzene nonane iodide 2.2 g of the product of Step A in 50 ml of acetone and 0.787 g of sodium iodide were stirred at reflux for one hour and then filtered. The filtrate was evaporated to dryness under reduced pressure and the 3.6 g of residue were taken up in 10 ml of ether and filtered. The filtrate was evaporated to dryness under reduced pressure to obtain 1.722 g of the desired product.

| IR Spectrum: (CHCl$_3$) | |
|---|---|
| C=O | 1735 cm$^{-1}$ |
| Dienone | 1658, 1602 cm$^{-1}$ |
| Aromatic | 1510 cm$^{-1}$ |

Step C 4-(3,17-dioxo-$\Delta^{4,9}$-estradien-11$\beta$-yl)-benzene decane nitrile 3.6 g of the product of Step B in 55 ml of ethanol and 10 ml of water with 0.872 g of potassium cyanide were stirred at reflux for 2 hours and then 50 ml of ice were added. The mixture was extracted with methylene chloride and the organic phase was dried and evaporated under reduced pressure to obtain 1.68 g of the desired product.

| IR Spectrum: (CHCl$_3$) | |
|---|---|
| C≡N | 2245 cm$^{-1}$ |
| C=O | 1735 cm$^{-1}$ |
| Dienone | 1658, 1602 cm$^{-1}$ |
| Aromatic | 1500 cm$^{-1}$ |

Step D 4-(3-acetoxy-17-oxo-$\Delta^{1,3,5(10)}$-estratrien-11$\beta$-yl)-benzene decane nitrile Using the procedure of Step B of Example 3, 1.27 g of the product of Step C were reacted to obtain after chromatography on silica (eluant: cyclohexane-ethyl acetate 1-1), 1.281 g of the desired product.

| IR Spectrum: (CHCl$_3$) | |
|---|---|
| C≡N | 2245 cm$^{-1}$ |
| C=O | 1750 cm$^{-1}$ (OAC) |
| | 1735 cm$^{-1}$ (17-keto) |
| Aromatic | 1606, 1582, 1512, 1413 cm$^{-1}$ |

Step E 4-(3-isobutyl-carbonyloxy-17-oxo-$\Delta^{1,3,5(10)}$-estratrien-11$\beta$-yl)-N-methyl-N-isopropyl-benzene nonamide a) Hydrolysis of the nitrile 1.225 g of the product of Step D, 24 ml of ethanol and 1.5 ml of sodium hydroxide were stirred at reflux for 60 hours and then cooled and poured into a mixture of 73 ml of N hydrochloric acid and 100 ml of ice. The mixture was stirred for 10 minutes and extracted with methylene chloride. The organic phase was dried, filtered and concentrated to dryness under reduced pressure to obtain 1.145 g of the desired product.

b) Amidification

To a solution of 1.145 g of the said product in 50 ml of methylene chloride, there were added 0.3 ml of N-methyl morpholine and 1 ml of isobutyl chloroformate and the mixture was stirred for 10 minutes. 1 ml of isopropyl methylamine was added and the mixture was stirred for 30 minutes at ambient temperature and then poured into 50 ml of a saturated solution of sodium bicarbonate. The mixtue was stirred for 10 minutes and then extracted with methylene chloride. The organic phase was dried and evaporated to dryness under reduced pressure. The 2 g of residue were chromatographed on silica (eluant: cyclohexane ethyl acetate 1-1) to obtain 0.778 g of the desired product.

| IR Spectrum: (CHCl₃) | |
|---|---|
| C=O | 1755 cm⁻¹ (ep.) |
| | 1737 cm⁻¹ (max) |
| | 1621 cm⁻¹ (amide III) |
| Aromatic | 1513, 1493 cm⁻¹ |

Step F

4-[3,17β-dihydroxy-Δ$^{1,3,5(10)}$-estratrien-11β-yl]-N-methyl-N-isopropyl-benzene nonamide a) Reduction of the 17-keto

Into a solution of 0.778 g of the product of Step E in 15 ml of tetrahydrofuran, there were introduced by fractions 0.451 g of tritertbutoxy aluminium-lithium hydride. The mixture was stirred for 30 minutes, then poured into ice-cooled solution of monosodium phosphate. The mixture was stirred for 30 minutes and then extracted with methylene chloride. The organic phase was evaporated to dryness under reduced pressure to obtain 0.9 g of the 17-hydroxy product.

b) Saponification

Using the procedure of Example 2B, the product obtained above was reacted to obtain after chromatography on silica (eluant: ethyl acetate-cyclohexane 6-4), 613 mg of the expected product with a specific rotation of $[\alpha]_D = -17° \pm 1°$ (c=1% in ethanol).

| IR Spectrum: (CHCl₃) | |
|---|---|
| OH | 3604 cm⁻¹ |
| C=O | 1618 cm⁻¹ |
| Aromatic | 1583 cm⁻¹ |
| | 1500 cm⁻¹ |

| Analysis: | C₃₇H₅₃NO₃; molecular weight = 559.84 | | | | | |
|---|---|---|---|---|---|---|
| Calculated: | % C | 79.38 | % H | 9.54 | % N | 2.50 |
| Found: | | 79.3 | | 9.7 | | 2.5 |

PREPARATION OF EXAMPLE 41

3-(1,2-ethanediyl) cyclic acetal of 5α-hydroxy-11β-[4-((6-hydroxy-hexyl)-oxy-phenyl]-Δ⁹-estren-3,17-dione

Step A 3-(1,2-ethanediyl) cyclic acetal of 11β-(4-hydroxyphenyl)-5α-hydroxy-Δ⁹-estren-3,17-dione a) Preparation of the Magnesium Compound

Using the procedure of Step A of Example 1, 7.1 g of magnesium turnings and 50 g of 4-trimethylsilyloxy-bromo-benzene were reacted to obtain an approximately 0.95M solution of magnesium compound in tetrahydrofuran.

b) Condensation

Using the procedure of Step A of Example 1, 10 g 3-(1,2-ethanediyl) cyclic acetal of 5α,10α-epoxy-Δ⁹-estren-3,17-dione obtained by EP 0,057,115 (Example 7) and 110 ml of the magnesium compound solution were reacted to obtain 34.9 g of crude product.

c) Desilylation

The crude product was dissolved in 150 ml of tetrahydrofuran, and after 130 ml of a 1M solution of tetrabutylammonium fluoride were added, the mixture was stirred for 15 minutes at ambient temperature, then poured into water. The mixture was extracted with ethyl acetate and the organic phase was washed with water, dried and evaporated to dryness under reduced pressure to obtain 26.9 g of crude product which was triturated at 40° C. for 30 minutes in 100 ml of an ethyl acetate-methylene chloride mixture (1-1). The mixture was filtered to obtain 5.77 g of the desired product. By chromatography on silica of the mother liquors (eluant: ethyl acetate-methylene chloride 1-1), an additional 5.7 g of the desired product were obtained and the combined batches of product (11.47 g) were crystallized from ethanol to obtain 8 g of the expected product melting at 255° C.

| IR Spectrum: (CHCl₃) | |
|---|---|
| OH region | 3464, 3280 cm⁻¹ |
| C=O | 1720 cm⁻¹ |
| Aromatic | 1613, 1592, 1511 cm⁻¹ |

Step B 3-(1,2-ethanediyl) cyclic acetal of 5α-hydroxy-11β-[4-((6-hydroxy-hexyl)-oxy)-phenyl]-Δ⁹-estren-3,17-dione To a solution of 3.77 g of the product of Step A in 18 ml of acetone, 13.3 ml of 2N sodium hydroxide and then 3 ml of bromohexanol were added and the mixture was heated at 50° C. for 3 hours, then poured into a saturated solution of ammonium chloride. The mixture was extracted with methylene chloride and the organic phase was evaporated to dryness under reduced pressure. The 7.7 g of residue were chromatographed on silica (eluant: methylene chloride-ethyl acetate 6-4 then 1-1) to obtain 4.11 g of the desired compound.

| IR Spectrum: (CHCl₃) | |
|---|---|
| OH— (of the chain) | 3620 cm⁻¹ |
| OH at position 5α | 3509 cm⁻¹ |
| Aromatic | 1609, 1578, 1509 cm⁻¹ |

EXAMPLE 41

7-(4-(3,17β-dihydroxy-Δ$^{1,3,5(10)}$-estratrien-11β-yl)-phenoxy)-N-methyl-N-isopropyl-heptanamide

Step A 3-(1,2-ethanediyl) cyclic acetal of 5α-hydroxy-11β-[4-[(6-[(4-methylphenyl)-sulfonyloxy)-hexyl]-oxy]-phenyl]-Δ⁹-estren-3,17-dione Using the procedure of Step A of Example 40, 4.08 g of the compound of the Preparation of Example 41 and 2.85 g of p-toluene sulfonyl chloride were reacted to obtain after chromatography on silica (eluant: methylene chloride-ethyl acetate 2-1), 4.19 g of the desired product which was used as is for the following step.

Step B 3-(1,2-ethanediyl) cyclic acetal of 5α-hydroxy-11β-[4-[(6-iodohexyl)-oxy]-phenyl]⁹-estrene-3,17-dione Using the procedure of Step B of Example 40, 4.19 g of the product of Step A and 1.39 g of sodium iodide were reacted to obtain 3.9 g of the desired product.

| IR Spectrum: (CHCl$_3$) | |
|---|---|
| OH at position 5 | 3508 cm$^{-1}$ |
| 17-keto | 1733 cm$^{-1}$ |
| Aromatic | 1609, 1575, 1508 cm$^{-1}$ |

Step C

[4-[3,3-(1,2-ethanediyl)-bis-oxy-5α-hydroxy-17-oxo-Δ⁹-estren-11β-yl]-phenoxy]-heptane nitrile Using the procedure of Step C of Example 40, 3.75 g of the compound of Step B and 780 mg of potassium cyanide were reacted to obtain after chromatography on silica (eluant: cyclohexane-ethyl acetate 1-1), 2.9 g of the desired product.

| IR Spectrum: (CHCl$_3$) | |
|---|---|
| OH at position 5α | 3510 cm$^{-1}$ |
| C≡N | 2248 cm$^{-1}$ |
| 17-keto | 1733 cm$^{-1}$ |
| Aromatic | 1609, 1576, 1508 cm$^{-1}$ |

Step D

[4-(3,20-dioxo-Δ⁴,⁹-estradien-11β-yl)-phenoxy]-heptane nitrile

A mixture of 2.46 g of the product of Step C, 13 ml of methanol and 4 ml of 2N hydrochloric acid was stirred for 2 hours at ambient temperature and after dilution with water, and extraction with methylene chloride, the organic phase was distilled under reduced pressure to obtain 2.2 g of crude product which was chromatographed on silica (eluant: cyclohexane-ethyl acetate 1-1) to obtain 1.875 g of the desired product melting at 176° C.

| IR Spectrum: (CHCl$_3$) | |
|---|---|
| C≡N | 2250 cm$^{-1}$ |
| 17-keto | 1735 cm$^{-1}$ |
| 3-keto | 1658 cm$^{-1}$ |
| C═C | 1609 cm$^{-1}$ |
| Aromatic | 1609, 1580, 1509 cm$^{-1}$ |

Step E

7-[4-(3-acetoxy-17β-hydroxy-Δ¹,³,⁵⁽¹⁰⁾-estratrien-11β-yl)-phenoxy]-heptane nitrile a) Aromatization

Using the procedure of Step B of Example 3, 1.693 g of the product of Step D and 1.7 ml of acetic anhydride and 0.85 ml of acetyl bromide were reacted to obtain 2.15 g of the desired crude product.

b) Reduction of the Ketone at Position 17

Using the procedure of Step B of Preparation 1, 2.15 g of the product above and 280 mg of sodium borohydride were reacted to obtain after chromatography on silica (eluant: ethyl acetate-cyclohexane 40-60), 1.12 g of the desired product.

| IR Spectrum: (CHCl$_3$) | |
|---|---|
| OH | 3612 cm$^{-1}$ |
| C≡N | 2250 cm$^{-1}$ |
| C═O | 1753 cm$^{-1}$ |
| Aromatic | 1610, 1580, 1512, 1494 cm$^{-1}$ |

Step F

7-[4-(3,17β-dihydroxy-Δ¹,³,⁵⁽¹⁰⁾-estratrien-11β-yl]-phenoxy]-heptanoic acid

Using the procedure of Step B of Example 2, 900 mg of the product of Step E were reacted to obtain after chromatography on silica (eluant: essence G-acetone 65-35 with 1% of acetic acid, then acetone only), 779 mg of the desired product.

| IR Spectrum: (CHCl$_3$) | |
|---|---|
| OH | 3602 cm$^{-1}$ |
| C═O | 1731, 1709 cm$^{-1}$ |
| Aromatic | 1610, 1581, 1512 cm$^{-1}$ |

Step G 7-(4-(3,17β-dihydroxy-Δ¹,³,⁵⁽¹⁰⁾-estratrien-11β-yl)-phenoxy)-N-methyl-N-isopropyl-heptanamide Using the procedure of Step A of Example 3, 400 mg of the product of Step F and 0.34 ml of isopropyl methylamine were reacted to obtain 511 mg of crude product (intermediate carbonate at position 3) which was saponified as in Step A of Example 2. After chromatography on silica (eluant: ethyl acetate then acetone with 1% of acetic acid) 336 mg of the desired product with a specific rotation of $[\alpha]_D = -39° \pm 2°$ (c=0.7% in ethanol) were obtained.

| IR Spectrum: (CHCl$_3$) | |
|---|---|
| OH | 3604 cm$^{-1}$ |
| C═O | 1619 cm$^{-1}$ amide III |
| aromatic | 1581, 1511 cm$^{-1}$ |

| Analysis: | C$_{35}$H$_{49}$NO$_4$; molecular weight = 547.79 | | | | | |
|---|---|---|---|---|---|---|
| Calculated: | % C | 76.74 | % H | 9.01 | % N | 2.55 |
| Found: | | 77.0 | | 9.0 | | 2.6 |

EXAMPLE 42

N-butyl-4-[3,17β-dihydroxy-19-nor-17α-Δ¹,³,⁵⁽¹⁰⁾-pregnatrien-20-yn-11β-yl]-N-methyl benzene Using the procedure of Example 21, the product of Step A of Preparation 4 was reacted to obtained 250 mg of the desired product.

| IR Spectrum: (CHCl$_3$) | |
|---|---|
| C≡CH | 3305 cm$^{-1}$ |
| OH | 3598 cm$^{-1}$ |
| C═O | 1621 cm$^{-1}$ |
| Aromatic | 1583, 1500 cm$^{-1}$ |

| Analysis: | C$_{39}$H$_{53}$NO$_3$; molecular weight = 583.86 | | | | | |
|---|---|---|---|---|---|---|
| Calculated: | % C | 80.23 | % H | 9.15 | % N | 2.4 |
| Found: | | 80.1 | | 9.3 | | 2.34 |

PREPARATION OF EXAMPLE 43

11β-(4-hydroxyphenyl-$\Delta^{4,9}$-estradien-3,17-dione

Using the procedure of Step B of Preparation 3, 1 g of the compound of Step A of the Preparation of Example 41 was reacted to obtain after chromatography on silica (eluant: methylene chloride-ethyl acetate 7-3), 703 mg of the sought product.

| IR Spectrum: (CHCl$_3$) | |
|---|---|
| OH | 3596 cm$^{-1}$ |
| C=O | 1735 cm$^{-1}$ |
| C=O | 1657 cm$^{-1}$ |
| Aromatic | 1612, 1593, 1511 cm$^{-1}$ |

PREPARATION B OF EXAMPLE 43

[(5-bromopentyl)-oxy]-N-butyl-N-methyl acetamide

Step A

Bromo-N-butyl-N-methyl acetamide

To a solution cooled to −20° C. of 11.9 ml of bromoacetyl bromide in 180 ml of ether there were added 26 g of butylmethylamine in solution in 120 ml of ether and then the temperature returned to 20° C. The mixture was stirred for 30 minutes and diluted with water and extracted with ether. The ether phase was evaporated to dryness under reduced pressure and the 27.4 g of residue were distilled under reduced pressure (0.05 mbar) at 79°/83° C. to obtain 19.36 g of the desired product.

| Analysis: C$_7$H$_{14}$BrNO; molecular weight = 208.105 | | | | | | | | |
|---|---|---|---|---|---|---|---|---|
| Calculated: | % C | 40.40 | % H | 6.78 | % N | 6.73 | % Br | 38.39 |
| Found: | | 40.3 | | 7.0 | | 6.7 | | 38.2 |

Step B

5-[[dimethyl-(1,1-dimethylethyl)-silyl]-oxy]-pentanol

To a solution of 10 g of 4-pentanol, 200 ml of methylene chloride, 19.5 ml of triethylamine and 566 mg of 4-dimethylamino pyridine, there were added with cooling, 19.14 g of tert-butyldimethylsilyl chloride. The mixture was stirred for one hour at ambient temperature, diluted with water and the decanted organic phase was washed, dried and evaporated to dryness under vacuum. The 42 g of residue were chromatographed on silica (eluant: essence G-ethyl acetate 95-5) to obtain 23.3 g of silyloxy pentene that was dissolved in 250 ml of tetrahydrofuran. 6 ml of borane-methylsulfide complex were added at 20° C. and the mixture was stirred for 30 minutes at 20° to 25° C., then for 30 minutes at 35° C. 18 ml of sodium hydroxide and then 18 ml of oxygenated water were added at 10° C. and the mixture was stirred for 30 minutes and diluted with water. The mixture was extracted with ethyl acetate and the organic phase was washed with a 10% sodium thiosulfate solution, dried and concentrated to dryness under reduced pressure. The 25.85 g of the residue were chromatographed on silica (eluant: cyclohexane-ethyl acetate 8-2) to obtain 22.7 g of product which was distilled under reduced pressure (0.06 mbar) to obtain 18.7 g of the desired compound with a boiling point of 73° to 75° C. at 0.06 mbar.

Step C

N-butyl-[(5-hydroxypentyl)-oxy]-N-methyl acetamide

To a solution of 8 g of the alcohol of Step B in 40 ml of tetrahydrofuran there were added 2.16 g of 50% sodium hydride in oil. The mixture was stirred for 30 minutes at ambient temperature and then a solution of 9.5 g of the brominated compound of Step A in 13 ml of tetrahydrofuran was added dropwise over 15 minutes. The mixture was stirred for 16 hours at ambient temperature and a saturated aqueous solution of ammonium chloride was added. The mixture was extracted with ethyl acetate and the organic phase was washed, dried and evaporated to dryness under vacuum to obtain 14.8 g of intermediate N-butyl-[5-[(dimethyl-(1,1-dimethylethyl)-silyl]-oxyl]-pentyl)-oxy]-N-methyl acetamide which was dissolved in 83 ml of tetrahydrofuran and 46 ml of a 1M solution of tetrabutyl ammonium fluoride. The mixture was stirred for 2 hours at ambient temperature and then poured into water and extracted with ethyl acetate. The organic phase was evaporated to dryness under reduced pressure and the 13.6 g of residue were chromatographed on silica (eluant: methylene chloride-isopropanol 94-6) to obtain 7.28 of the desired compound.

| IR Spectrum: (CHCl$_3$) | |
|---|---|
| —OH | 3628 cm$^{-1}$ |
| C=O | 1645 cm$^{-1}$ |

Step D

[(5-bromopentyl)-oxy]-N-butyl-N-methyl acetamide

To a solution of 7.2 g of the product of Step c in 73 ml of methylene chloride, there were added at −10° C., 13 g of tetrabromoethane and 10.3 g of triphenylphosphine and the reaction medium was stirred for one hour at 0° C. and chromatographed on silica (eluant: ethyl acetate-cyclohexane 7-3) to obtain 7.49 g of the desired compound.

| IR Spectrum: (CHCl$_3$) | | | | | | | | |
|---|---|---|---|---|---|---|---|---|
| C=O | | | | | | | 1644 cm$^{-1}$ | |
| Analysis: C$_{12}$H$_{24}$BrNO$_2$; molecular weight = 294.24 | | | | | | | | |
| Calculated: | % C | 48.98 | % H | 8.22 | % N | 4.76 | % Br | 27.15 |
| Found: | | 48.6 | | 8.2 | | 4.6 | | 26.3 |

EXAMPLE 43

N-butyl-[5-[4-(3,17β-dihydroxy-$\Delta^{1,3,5(10)}$-estratrien-11β-yl)-phenoxy]-pentyloxy]-N-methyl acetamide

Step A

N-butyl-[5-[4-(3,17-dioxo-$\Delta^{4,9}$-estradien-11β-yl)-phenoxy]-pentyloxy]-N-methyl acetamide To a solution of 2.5 g of the product of Step A of the Preparation of Example 41 in 26 ml of acetone and 6.4 ml of 2N sodium hydroxide, there were added 3.75 g of [(5-bromopentyl)-oxy]-N-butyl-N-methyl acetamide (obtained in the above preparation) in solution in 6 ml of acetone. The mixture was stirred for 5 hours at 50° C., cooled and poured into water. The mixture was acidified with 2N hydrochloric acid and extracted with ethyl acetate. After washing, drying and evaporating to dryness under reduced pressure, the 6.8 g of residue were chromatographed on silica (eluant: ethyl acetate) to obtain 2.63 g of the desired product.

| IR Spectrum: (CHCl$_3$) | |
|---|---|
| C=O | 1735 cm$^{-1}$ (17-keto) |
|  | 1657 cm$^{-1}$ |
| C=C + Aromatic | 1609, 1580, 1509 cm$^{-1}$ |

Step B

N-butyl-[5-[4-(3-hydroxy-17-oxo-$\Delta^{1,3,5(10)}$-estratrien-11$\beta$-yl)-phenoxy]-pentyloxy]-N-methyl acetamide Using the procedure of Step A of Example 2, 2.61 g of the product of Step A and 2.61 g of palladium hydroxide over magnesium oxide were reacted to obtain after chromatography on silica (eluant: ethyl acetate-essence G 9-9), 1.83 g of the desired product.

| IR Spectrum: (CHCl$_3$) | |
|---|---|
| OH | 3598 cm$^{-1}$ |
| C=O | 1732 cm$^{-1}$ (17-keto) |
|  | 1634 cm$^{-1}$ (amide III) |
| Aromatic | 1611, 1581, 1511 cm$^{-1}$ |

Step C

N-butyl-[5-[4-(3,17$\beta$-dihydroxy-$\Delta^{1,3,5(10)}$-estratrien-11$\beta$-yl)-phenoxy]-pentyloxy]-N-methyl acetamide Using the procedure of Step B of Preparation 1, 500 mg of the product of Step B 66 mg of sodium borohydride were reacted. The 514 mg of residue were chromatographed on silica (eluant: methylene chloride-isopropanol 95-5), then a second time (eluant: ethyl acetate) to obtain 343 mg of the desired product with a specific rotation of $[\alpha]_D = -31.1°$ (c=1% in chloroform).

| IR Spectrum: (CHCl$_3$) | |
|---|---|
| OH | 3603 cm$^{-1}$ |
| C=O | 1634 cm$^{-1}$ (amide III) |
| Aromatic | 1611, 1581, 1511 cm$^{-1}$ |

| Analysis: C$_{36}$H$_{51}$NO$_5$; molecular weight = 577.81 | | | |
|---|---|---|---|
| Calculated: | % C 74.83 | % H 8.89 | % N 2.42 |
| Found: | 74.8 | 9.0 | 2.3 |

EXAMPLE 44

N-butyl-[5[-4-(3,17$\beta$-dihydroxy-19-nor-17$\alpha$-$\Delta^{1,3,5(10)}$-pregnatrien-20-yn-11$\beta$-yl)-phenoxy]-pentyloxy]-N-methyl acetamide To a solution of 500 mg of the product of Example 43 in 4 ml of tetrahydrofuran, there were added 6 ml of a 0.44M solution of potassium acetylide in tetrahydrofuran (prepared by bubbling acetylene through a solution of potassium tert-butylate in tetrahydrofuran) and after stirring for 30 minutes, the mixture was poured into a saturated solution of ammonium chloride. After extraction with ethyl acetate, followed by washing, drying and evaporating to dryness under reduced pressure, the 504 mg of residue were chromatographed on silica (eluant: ethyl acetate-essence G 85-15), then under pressure (eluant: methylene chloride-acetone 90-10) to obtain 264 mg of desired product with a specific rotation of $[\alpha]_D = -107° \pm 2.5°$ (c=0.8% in ethanol).

| IR Spectrum: (CHCl$_3$) | |
|---|---|
| OH | 3600 cm$^{-1}$ |
| C≡CH | 3304 cm$^{-1}$ |
| C=O | 1634 cm$^{-1}$ |
| Aromatic | 1611, 1581, 1511 cm$^{-1}$ |

| Analysis: C$_{38}$H$_{51}$NO$_5$; molecular weight = 601.83 | | | |
|---|---|---|---|
| Calculated: | % C 74.83 | % H 8.54 | % N 2.32 |
| Found: | 74.8 | 8.6 | 2.2 |

PREPARATION OF EXAMPLE 45

8-[4-(3,17-dioxo-$\Delta^{4,9}$-estradien-11$\beta$-yl)-phenoxy]-octanoic acid

Step A 3-(1,2-ethanediyl) cyclic acetal of 11$\beta$-[4-[(8-hydroxyacetyl)-oxy]-phenyl]-5$\alpha$-hydroxy-$\Delta^9$-estren-3,17-dione Using the procedure of Step A of Example 43, 1.5 g of the product of Step A of the Preparation of Example 41 and 2.22 g of 8-bromo octanol were reacted to obtain after chromatography on silica (eluant: ethyl acetate-methylene chloride 6-4), 1.475 g of the desired product.

| IR Spectrum: (CHCl$_3$) | |
|---|---|
| OH | 3620, 3509 cm$^{-1}$ |
| 17-keto | 1733 cm$^{-1}$ |
| Aromatic | 1609, 1577, 1508 cm$^{-1}$ of the type —C$_6$H$_4$OH |

Step B

11$\beta$-[4-[(8-hydroxy-octyl)-oxy]-phenyl]-$\Delta^{4,9}$-estradien-3,17-dione Using the procedure of Step B of Preparation 2, 1.44 g of the product of Step A were reacted to obtain after chromatography on silica (eluant: ethyl acetate-methylene chloride 1-1), 1.049 g of the expected product.

| IR Spectrum: (CHCl$_3$) | |
|---|---|
| OH | 3620 cm$^{-1}$ |
| 17-keto | 1735 cm$^{-1}$ |
| Dienone | 1658 cm$^{-1}$ |
| C=C + Aromatic | 1609, 1580, 1509 cm$^{-1}$ |

Step C

8-[4-(3,17-dioxo-$\Delta^{4,9}$-estradien-11$\beta$-yl)-phenoxy]-octanoic acid

Using the procedure of Step C of Preparation 2, 1,008 g of the product of Step B and 1.25 ml of Heilbron-Jones reagent were reacted to obtain 1.009 g of the desired product.

| IR Spectrum: (CHCl$_3$) | |
|---|---|
| Acid (according to the OH region) with C=O: | 1710 cm$^{-1}$ |
| 17-keto | 1735 cm$^{-1}$ |
| Dienone | 1658 cm$^{-1}$ |

| IR Spectrum: (CHCl₃) | |
|---|---|
| C=C + aromatic | 1609, 1580, 1509 cm⁻¹ |

EXAMPLE 45

8-[4-(3,17β-dihydroxy-Δ$^{1,3,5(10)}$-estratrien-11β-yl)-phenoxy]-N-methyl-N-isopropyl octanamide

Step A

8-[4-(3,17β-dioxo-Δ$^{4,9}$-estradien-11β-yl)-phenoxy]-N-methyl-N-isopropyl octanamide Using the procedure of Step A of Example 3, 1 g of the product of the Preparation and 1.03 ml of N-isopropyl methylamine were reacted to obtain after chromatography on silica (eluant: ethyl acetate-methylene chloride 60-40), 722 mg of the desired product.

| IR Spectrum: (CHCl₃) | |
|---|---|
| Amide III | 1621 cm⁻¹ |
| 17-keto | 1735 cm⁻¹ |
| Dienone | 1658 cm⁻¹ |
| C=C + Aromatic | 1580, 1509 cm⁻¹ |

Step B

8-[4-(3,17β-dihydroxy-Δ$^{1,3,5(10)}$-estratrien-11β-yl)-phenoxy]-N-methyl-N-isopropyl octanamide a) Aromatization Using the procedure of Step A of Example 2, 695 mg of the product of Step A and 0.7 ml of acetic anhydride and 0.35 ml of acetyl bromide were reacted to obtain 815 mg of the crude intermediate 3-acetoxy compound.

b) Saponification

Using the procedure of Step A of Example 2, 677 mg of crude 3-hydroxy-17-keto product were obtained.

c) Reduction of the Ketone at Position 17

Using the procedure of Example 28, 767 mg of lithium tritertbutoxy alumino hydride were reacted to obtain after chromato graphy on silica (eluant: ethyl acetate-methylene chloride 6-4), then successively, under pressure, methanol-water (85-15), (75-25) and finally twice with ethyl acetate-methylene chloride (6-4), 211 mg of the desired product with a specific rotation of $[\alpha]_D = -45° \pm 2°$ (c=0.7% in ethanol).

| IR Spectrum: (CHCl₃) | |
|---|---|
| OH | 3603 cm⁻¹ |
| C=O | 1619 cm⁻¹ (amide III) |
| Aromatic | 1612, 1581, 1511 cm⁻¹ |

| Analysis: C₃₆H₅₁NO₄; molecular weight = 561.81 | | | |
|---|---|---|---|
| Calculated: | % C 76.96 | % H 9.15 | % N 2.49 |
| Found: | 77.3 | 9.3 | 2.5 |

PREPARATION OF EXAMPLE 46

8-bromo-N-butyl-N-methyl-octanamide

Using the procedure of Step A of Example 3, 5 g of 8-bromo octanoic acid and 13 ml of N-methyl butylamine were reacted to obtain after chromatography on silica (eluant: methylene chloride-acetone 95-5), 6.14 g of the expected product.

IR Spectrum: (CHCl₃) C=O (tertiary amide type): 1627 cm⁻¹

EXAMPLE 46

N-butyl-8-[4-(3,17β-dihydroxy-Δ$^{1,3,5(10)}$-estratrien-11β-yl)-phenoxy]-N-methyl octanamide

Step A

8-[4-(3,17β-dioxo-Δ$^{4,9}$-estradien-11β-yl)-phenoxy]-N-butyl-N-methyl octanamide Using the procedure of Step A of Example 43, 725 mg of the product of the Preparation of Example 43 and 0.2 ml of 8-bromo-N-butyl-N-methyl octanamide obtained in the above preparation were reacted to obtain after chromatography on silica (eluant: essence G-ethyl acetate 4-6), 540 mg of the expected product.

| IR Spectrum: (CHCl₃) | |
|---|---|
| 17-keto | 1735 cm⁻¹ |
| 3-keto | 1657 cm⁻¹ |
| Amide III | 1628 cm⁻¹ |
| Aromatic bands | 1580, 1509 cm⁻¹ of the type —O—C₆H₅ |

Step B

8-[4-(3-hydroxy-17-oxo-Δ$^{1,3,5(10)}$-estratrien-11β-yl)-phenoxy]-N-butyl-N-methyl octanamide Using the procedure of Step A of Example 2, 470 mg of the product of Step A and 260 mg of palladium hydroxide over magnesium oxide were reacted to obtain after chromatography on silica (eluant: ethyl acetate-essence G 1-1), 360 mg of the desired compound.

| IR SPectrum: (CHCl₃) | |
|---|---|
| OH | 3596 cm⁻¹ |
| C=O | 1732 cm⁻¹ |
| Amide III | 1623 cm⁻¹ |
| Aromatic bands | 1581, 1511 cm⁻¹ |

Step C

N-butyl-8-[4-(3,17β-dihydroxy-Δ$^{1,3,5(10)}$-estratrien-11β-yl)-phenoxy]-N-methyl octanamide Using the procedure of Step B of Preparation 1, 360 mg of the product of Step B and 72 mg of sodium borohydride were reacted to obtain the desired product.

| IR Spectrum: (CHCl₃) | |
|---|---|
| OH | 3602 cm⁻¹ |
| C=O | 1623 cm⁻¹ (amide III) |
| Aromatic | 1581, 1511 cm⁻¹ |

EXAMPLE 47

N-butyl-8-[4-(3,17β-dihydroxy-19-nor-17α-Δ$^{1,3,5(10)}$-pregnatrien-20-yn-11β-yl)-phenoxy]-N-methyl octanamide

Step A

N-butyl-8-[4-(17β-hydroxy-3-oxo-19-nor-17α-Δ$^{4,9}$-pregnadien-20-yl-11β-yl)-phenoxy]-N-methyl octanamide Using the procedure of Step A of Example 43, 1.975 g of 17β-hydroxy-11β-(4-hydroxyphenyl)-19-nor-17-Δ$^{4,9}$-pregnadien-20-yn-3-one (prepared according to French Patent No. 2,522,328) and 1.9 ml of 8-bromo-N-butyl-N-methyl octanamide (Preparation A of Example 46) were reacted to obtain after chromatography on silica (eluant: ethyl acetate-cyclohexane 7-3), 2.45 g of the expected product.

| IR Spectrum: (CHCl$_3$) | |
| --- | --- |
| OH | 3598 cm$^{-1}$ |
| C≡CH | 3305 cm$^{-1}$ |
| C=O | 1644 and 1628 cm$^{-1}$ amide III |
| C=C + Aromatic | 1611, 1508 cm$^{-1}$ |

Step B

N-butyl-N-methyl-8-[4-[3-oxo-17β-(tetrahydro-2H-2-pyranyloxy]-19-nor-17α-Δ$^{4,9}$-pregnadien-11β-yl)-phenoxy]-octanamide To a solution of 2.45 g of the compound of Step A in 25 ml of anhydrous tetrahydrofuran and 5 ml of dihydropyran, there were added 75 mg of p-toluene sulfonic acid and the mixture was stirred for 2 hours at ambient temperature. 1 ml of triethylamine was added and the mixture was diluted with a sodium bicarbonate solution. Extraction was effected with ethyl acetate and the organic phase was washed, dried, and evaporated to dryness under reduced pressure. The 4.3 g of residue were chromatographed on silica (eluant: ethyl acetate-cyclohexane 7-3) to obtain 2.61 g of the expected compound.

| IR Spectrum: (CHCl$_3$) | |
| --- | --- |
| Absence of OH | |
| C≡CH | 3304 cm$^{-1}$ |
| C=O | 1644, 1628 cm$^{-1}$ |
| C=C and Aromatic | 1610, 1508 cm$^{-1}$ |

Step C

N-butyl-8-[4-(3,17β-dihydroxy-19-nor-17α-Δ$^{1,3,5(10)}$-pregnatrien-20-yl-11β-yl)-phenoxy]-N-methyl octanamide Using the procedure of Example 8, 515 mg of the product of Step B and 0.5 ml of acetic anhydride and 0.25 ml of acetyl bromide were reacted and for the saponification, 1 ml of sodium hydroxide was used. After chromatography on silica (eluant: essence G-ethyl acetate 1-1), 460 mg of the desired product were obtained.

| IR Spectrum: (CHCl$_3$) | |
| --- | --- |
| OH | 3599 cm$^{-1}$ |
| C≡CH | 3304 cm$^{-1}$ |
| C=O | 1623 cm$^{-1}$ amide III |
| Aromatic | 1611, 1581, 1511, 1502 cm$^{-1}$ (ep) |

| Analysis: C$_{39}$H$_{53}$NO$_4$ | | | |
| --- | --- | --- | --- |
| Calculated: | % C 78.09 | % H 8.90 | % N 2.33 |
| Found: | 78.0 | 8.9 | 2.1 |

PREPARATION OF EXAMPLE 48

9-bromo-N-butyl-N-methyl-7-nonynamide

Step A 6-bromo-N-butyl-N-methyl hexanamide

Using the procedure of Step A of Example 3, 4.88 g of 6-bromohexanoic acid and 4.36 ml of N-methylbutylamine were reacted to obtain 7.0 g of the expected product which was used as is for the following step.

Step B

N-butyl-9-hydroxy-N-methyl-7-nonynamide

A solution of 1.77 ml of propargyl alcohol, 30 ml of tetrahydrofuran and 7.5 ml of hexamethyl phosphotriamide cooled to −60° C. was admixed with 37.5 ml of a 1.6M solution of butyllithium in hexane and after stirring for 45 minutes at −30° C., 7 g of the product of Step A in solution in 7 ml of tetrahydrofuran were added. The mixture was stirred for 16 hours at ambient temperature and then poured into a saturated solution of ammonium chloride and extracted with ethyl acetate. The organic phase was washed with 2N hydrochloric acid and with a saturated solution of sodium bicarbonate, dried and evaporated to dryness. The 5.78 g of residue were chromatographed on silica (eluant: methylene chloride-ethyl acetate 70-30, then methylene chloride-isopropanol 95-5) to obtain 1.65 g of the desired product.

| IR Spectrum: (CHCl$_3$) | |
| --- | --- |
| OH | 3611 cm$^{-1}$ |
| C=O | 1627 cm$^{-1}$ amide |

Step C 9-bromo-N-butyl-N-methyl-7-nonynamide

To a solution of 1.65 g of the product of Step B in 16.5 ml of methylene chloride cooled to −5° C. there were added 2.85 g of carbon tetrabromide and 2.25 g of triphenylphosphine. The reaction solution was stirred for 30 minutes at 0° C. and chromatogaphed on silica (eluant: methylene chloride-ethyl acetate 90-10) to obtain 1.82 g of the desired product.

| IR Spectrum: (CHCl$_3$) | |
| --- | --- |
| C=O | 1628 cm$^{-1}$ amide |
| C≡C | 2230 cm$^{-1}$ |

EXAMPLE 48

N-butyl-9-[4-(3,17β-dihydroxy-Δ$^{1,3,5(10)}$-estratrien-11β-yl)-phenoxy]-N-methyl-7-nonynamide

Step A

N-butyl-9-[4-(3,17-dioxo-Δ$^{1,3,5(10)}$-estratrien-11β-yl)-phenoxy]-N-methyl-7-nonynamide Using the procedure of Step A of Example 43, 816 mg of the compound of Preparation of Example 43 and 1.25 g of 9-bromo-N-butyl-N-methyl-7-nonynamide (above preparation) were reacted to obtain 2.2 g of crude product to which was added 270 mg of a previous lot. The mixture was chromatographed on silica (eluant: ethyl acetate-essence G 75-25) to obtain 1.126 g of the expected product.

| IR Spectrum: (CHCl$_3$) | |
|---|---|
| C≡C | 2220 cm$^{-1}$ |
| C=O | 1735 cm$^{-1}$ (17-keto) |
| | 1657 cm$^{-1}$ (3-keto) |
| Amide III | 1628 cm$^{-1}$ |
| C=C + Aromatic | 1610, 1582, 1508 cm$^{-1}$ |

Step B

N-butyl-9-[4-(3,17β-dihydroxy-Δ$^{1,3,5(10)}$-estratrien-11β-yl)-phenoxy]-N-methyl-7-nonynamide Using the procedure of Steps B and C of Example 3, 1.1 g of the product of Step A and 1.1 ml of acetic anhydride and 0.55 ml of acetyl bromide were reacted to obtain the 3-acetoxy. 2.8 ml of 2N sodium hydroxide were used for the saponification at the 3-position and 142 mg of sodium borohydride were used for the reduction of the 17-keto. After successive chromatography on silica (eluant: ethyl acetate-essence G 70-30), microbondapack C$_{18}$ (eluant: methanol-water 80-20), then again on silica (eluant: ethyl acetate-essence G 70-30), 540 mg of desired product with a specific rotation of [α]$_D$= −67°±2° (c=0.83% in chloroform) were obtained.

| IR Spectrum: (CHCl$_3$) | | |
|---|---|---|
| OH | 3606 cm$^{-1}$ | |
| C≡C | 2220 cm$^{-1}$ | |
| C=O | 1620 cm$^{-1}$ | |
| Aromatic | 1582, 1510 cm$^{-1}$ | |
| Analysis: C$_{38}$H$_{51}$NO$_4$; molecular weight = 585.83 | | |
| Calculated: | % C 77.91 | % H 8.77 | % N 2.39 |
| Found: | 78.0 | 9.0 | 2.3 |

EXAMPLE 49

N-butyl-9-[4-(3,17β-dihydroxy-Δ$^{1,3,5(10)}$-estratrien-11β-yl)-phenoxy]-N-methyl nonanamide

A solution of 212 mg of the product of Example 48 and 42 mg of Wilkinson catalyst in solution in 2 ml of toluene and 2 ml of ethanol were hydrogenated under 1900 mbars for one hour and after filtering, the filtrate was evaporated under reduced pressure. The 265 mg of residue were chromatographed on silica (eluant: ethyl acetate-essence G 70-30) to obtain 168 mg of the desired compound with a specific rotation of [α]$_D$= −32° (c=0.49% in CHCl$_3$).

| IR Spectrum: (CHCl$_3$) | | |
|---|---|---|
| OH | 3603 cm$^{-1}$ | |
| C=O | 1624 cm$^{-1}$ | |
| Aromatic | 1581, 1511 cm$^{-1}$ | |
| Analysis: C$_{38}$H$_{55}$NO$_4$ | | |
| Calculated: | % C 77.37 | % H 9.4 | % N 2.38 |
| Found: | 77.4 | 9.6 | 2.4 |

PREPARATION OF EXAMPLE 50

17β-acetyloxy-11β-(10-hydroxy-decyl)-Δ$^{4,9}$-estradien-3-one

Step A 3-(1,2-ethanediyl cyclic acetal) of 11β-[11-[[(1,1-dimethylethyl)-silyl]-oxy]-decyl]-5α-hydroxy-Δ$^9$-estrene-3,17-dione Using the procedure of Step A of Preparation 5, 19.5 g of the epoxide of EP No. 0,057,115 (Example 7) and 113.5 ml of a 0.59M solution of 10-(dimethyl-tert-butyl-silyloxy)-decyl magnesium compound were reacted to obtain 43.78 g of crude product to which was added 11.3 g of a previous preparation. The mixture was chromatographed on silica (eluant: cyclohexane-ethyl acetate 7-3) to obtain 23.15 g of the desired product.

| IR Spectrum: (CHCl$_3$) | |
|---|---|
| OH | 3616 cm$^{-1}$ (at position 17) |
| | 3508 cm$^{-1}$ (at position 5) |
| C=O | 1732 cm$^{-1}$ (17-keto) |

Step B (1,2-ethanediyl cyclic acetal) of 5α,17β-dihydroxy-11β-[[10-[dimethyl-(1,1-dimethylethyl)-silyl]-oxy]-decyl]-Δ$^9$-estren-3-one Using the procedure of Step B of Preparation 5, 23.57 g of the product of Step A and 1.447 g of sodium borohydride were reacted to obtain 22.342 g of the desired product. 103 mg of the product were chromatographed on silica (eluant: cyclohexane-ethyl acetate 1-1) to obtain 96.8 mg of pure product.

| IR Spectrum: (CHCl$_3$) | |
|---|---|
| OH | 3612, 3510 cm$^{-1}$ |
| t-butyldimethylsilyloxy | 1255, 836 cm$^{-1}$ |

Step C (1,2-ethanediyl cyclic acetal) of 17β-acetyloxy-11β-[[10-[dimethyl-(1,1-dimethylethyl)-silyl]-oxy]-decyl]-5α-hydroxy-Δ$^9$-estrene-3-one Using the procedure of Step C of Preparation 5, 22.225 g of the product of Step B and 44.5 ml of pyridine and 22.25 ml of acetic anhydride were reacted to obtain 23.74 g of the expected product.

Step D

17β-acetyloxy-11β-(10-hydroxy-decyl)-Δ$^{4,9}$-estradien-3-one

Using the procedure of Step D of Preparation 5, 23.74 g of the product of Step C and 100 ml of 2N hydrochloric acid were reacted and chromatographed on silica (eluant: cyclohexane-ethyl acetate 1-1) to obtain 15.238 g of the expected product.

| IR Spectrum: (CHCl$_3$) | |
|---|---|
| OH | 3616 cm$^{-1}$ |
| Dienone | 1654, 1600 cm$^{-1}$ |

EXAMPLE 50

17β-hydroxy-N-methyl-N-isopropyl-3-oxo-Δ$^{4,9}$-estradien-11β-decanamide

Step A

17β-acetoxy-3-oxo-Δ$^{4,9}$-estradien-11β-decanoic acid

Using the procedure of Step E of Preparation 5, 942 mg of 17β-acetoxy-3-oxo-Δ$^{4,9}$-estradien-11β-decanol (obtained in the above preparation) and 1.1 ml of Heilbron-Jones reagent were reacted to obtain 964 mg of the expected product which was used as is for the next step.

Step B

17β-acetoxy-N-methyl-N-isopropyl-3-oxo-Δ$^{4,9}$-estradien-11β-decanamide

Using the procedure of Step A of Example 3, 940 mg of the product of Step A and 0.41 ml of methylisopropylamine were reacted to obtain after chromatography on silica (eluant: essence G-ethyl acetate 1-1), 705 mg of the desired product.

| IR Spectrum: (CHCl$_3$) | |
|---|---|
| OAC | 1728 cm$^{-1}$ |
| Dienone | 1653 cm$^{-1}$ |
| Amide III | 1622 cm$^{-1}$ |

Step C

17β-hydroxy-N-methyl-N-isopropyl-3-oxo-Δ$^{4,9}$-estradien-11β-decanamide

Using the procedure of Step B of Example 1, 194 mg of the compound of Step B and 0.3 ml of 2N sodium hydroxide were reacted to obtain after chromatography of silica (eluant: ethyl acetate), 165 mg of the expected product.

| IR Spectrum: (CHCl$_3$) | | |
|---|---|---|
| OH | 3613 cm$^{-1}$ | |
| Dienone | 1644 cm$^{-1}$ | |
| Amide III | 1621 cm$^{-1}$ | |
| Analysis: C$_{32}$H$_{51}$NO$_3$; molecular weight = 497.77 | | |
| Calculated: | % C 77.21 % H 10.32 | % N 2.81 |
| Found: | 77.1 10.3 | 2.8 |

EXAMPLE 51

3,17β-dihydroxy-N-methyl-N-isopropl-Δ$^{1,3,5(10)}$-estratrien-11β-decanamide

Using the procedure of Example 2, 0.5 g of the compound of Example 50 and 0.5 ml of acetic anhydride and 0.25 ml of acetyl bromide were reacted during aromatization and 1.6 ml of 2N sodium hydroxide were used for the saponification. After chromatography on silica (eluant: ethyl acetate-essence G 7-3) 357 mg of the expected product were obtained. After crystallization from ethyl acetate, 318 mg of the desired product melting at 150° C. were obtained.

| IR Spectrum: (CHCl$_3$) | | |
|---|---|---|
| OH | 3605 cm$^{-1}$ | |
| C=O (amide) | 1617 cm$^{-1}$ | |
| Aromatic | 1583, 1498 cm$^{-1}$ | |
| Analysis: C$_{32}$H$_{51}$NO$_3$; molecular weight = 497.77 | | |
| Calculated: | % C 77.21 % H 10.32 | % N 2.81 |
| Found: | 77.4 10.5 | 2.9 |

EXAMPLE 52

10-(17β-hydroxy-3-oxo-Δ$^{4,9}$-estradien-11β-yl)-decyl methyl isopropyl carbamate

Step A 10-(17β-acetoxy-3-oxo-Δ$^{4,9}$-estradien-11β-yl)-decyl methyl isopropyl carbamate To a solution of 470 mg of 17β-acetoxy-3-oxo-Δ$^{4,9}$-estradien-11β-decanol (obtained in the Preparation of Example 50) in 4 ml of toluene and 122 mg of dimethylamino pyridine at 0° C., 118 mg of triphosgene were added and the mixture was stirred for 30 minutes at ambient temperature. 312 ml of methylisopropylamine were added and the mixture was stirred for 30 minutes at ambient temperature and then poured into 0.1N hydrochloric acid. The mixture was extracted with ethyl acetate and the organic phase was washed, dried and evaporated to dryness. The 642 mg of residue were chromatographed on silica (eluant: essence G-ethyl acetate 6-4) to obtain 545 mg of the desired product.

| IR Spectrum: (CHCl$_3$) | |
|---|---|
| C=O (OAC) | 1728 cm$^{-1}$ |
| C=O (amide) | 1672 cm$^{-1}$ |
| C=O (dienone) | 1657 cm$^{-1}$ |
| C=C conjugated | 1601 cm$^{-1}$ |

Step B 10-(17β-hydroxy-3-oxo-Δ$^{4,9}$-estradien-11β-yl)-decyl methyl-isopropyl-carbamate Using the procedure of Step B of Example 1, 293 mg of the product of Step A and 1 ml of 2N sodium hydroxide were reacted to obtain after chromatography on silica (eluant: essence G-ethyl acetate 1-1), 244 mg of the desired product.

| IR Spectrum: (CHCl$_3$) | | |
|---|---|---|
| Carbamate | 1672 cm$^{-1}$ | |
| Dienone | 1657, 1600 cm$^{-1}$ | |
| OH | 3615 cm$^{-1}$ | |
| Analysis: C$_{33}$H$_{53}$NO$_4$; molecular weight = 527.79 | | |
| Calculated: | % C 75.10 % H 10.12 | % N 2.65 |
| Found: | 74.9 10.1 | 2.7 |

EXAMPLE 53

10-(3,17β-dihydroxy-Δ$^{1,3,5(10)}$-estratrien-11β-yl)-decyl methyl isopropyl carbamate

Step A 10-(3,17β-diacetoxy-Δ$^{1,3,5(10)}$-estratrien-11β-yl)-decyl methyl isopropyl carbamate Using the procedure of Step A of Example 8, 230 mg of the compound of Step A of Example 52 and 230 ml of acetic anhydride and 115 ml of acetyl bromide were reacted to obtain 234 mg of the expected product.

| IR Spectrum: (CHCl$_3$) | |
|---|---|
| C=O | 1730 cm$^{-1}$ (OAC at position 17) |
| | 1750 cm$^{-1}$ (OAC at position 3) |
| | 1680 cm$^{-1}$ (carbamate) |

Step B 10-(3,17β-dihydroxy-Δ$^{1,3,5(10)}$-estratrien-11β-yl)-decyl methyl isopropyl carbamate Using the procedure of Step B of Example 8, 260 mg of the product of Step A were reacted to obtain after chromatography on silica (eluant: essence G-ethyl acetate 6-4), 245 mg of the desired product.

| Analysis: C$_{33}$H$_{53}$NO$_4$; molecular weight = 527.79 | | | |
|---|---|---|---|
| Calculated: | % C 75.10 | % H 10.12 | % N 2.65 |
| Found: | 75.6 | 10.5 | 2.6 |

| IR Spectrum: (CHCl$_3$) | |
|---|---|
| OH | 3606 cm$^{-1}$ |
| >=O | 1672 cm$^{-1}$ |
| Aromatic | 1619, 1610, 1583, 1498 cm$^{-1}$ |

EXAMPLE 54

3,17β-dihydroxy-17α-methyl-N-methyl-isopropyl-Δ$^{1,3,5(10)}$-estratrien-11β-undecanamide

Step A 3-hydroxy-N-methyl-N-isopropyl-17-oxo-Δ$^{1,3,5(10)}$-estratrien-11β-undecanamide One agitated under reflux for 30 minutes 1 g of the product of Step A of Example 15 with 200 ml of methanol as well as 2.2 g of palladium hydroxide on magnesium compound were refluxed with stirring for 30 minutes and was then filtered. Evaporation of the solvents under reduced pressure yielded 985 mg of product which was chromatographed on silica (eluant: acetonitrile) to obtain 543 mg of the desired product with a specific rotation of [α]$_D$= +121°±3° (c=0.5% in ethanol).

| IR Spectrum: (CHCl$_3$) | |
|---|---|
| OH | 3598 cm$^{-1}$ |
| C=O | 1732 cm$^{-1}$ (17-keto) |
| | 1619 cm$^{-1}$ |
| Aromatic | 1582, 1499 cm$^{-3}$ |

Step B 3,17β-dihydroxy-N-methyl-N-isopropyl-19-nor-17α-Δ$^{1,3,5(10)}$-pregnatrien-20-yn-11β-undecanamide To a solution of 0.5 g of the product of Step A in 10 ml of anhydrous tetrahydrofuran at 20° C., 13.7 ml of 0.6M ethyl magnesium bromide were added and the mixture was stirred for 2 hours then poured into an ammonium chloride solution. The mixture was extracted with methylene chloride, dried and evaporated to dryness under reduced pressure. The 466 mg of residue were chromatographed on silica (eluant: methylene chloride-acetone 9-1) to obtain 225 mg of the expected product melting at 148° C. and with a specific rotation of [α]$_D$= +83°±2.5° (c=0.5% in ethanol).

| IR Spectrum: (CHCl$_3$) | |
|---|---|
| OH | 3640 cm$^{-1}$ |
| >C=O | 1617 cm$^{-1}$ (amide III) |
| Aromatic | 1582, 1498 cm$^{-1}$ |

| Analysis: C$_{32}$H$_{55}$NO$_3$; molecular weight = 525.82 | | | |
|---|---|---|---|
| Calculated: | % C 77.66 | % H 10.54 | % N 2.66 |
| Found: | 77.9 | 10.8 | 2.5 |

EXAMPLE 55

3,17β-dihydroxy-N-methyl-N-isopropyl-19-nor-17α-Δ$^{1,3,5(10)}$-pregnatrien-20-yn-11β-undecanamide Using the procedure of Step C of Example 21, 0.954 g of the product of Step A of Example 54 and 1.470 g of lithium acetylide-ethylene diamine complex were reacted to obtain after chromatography on silica (eluant: methylene chloride-acetone 9-1), 284 mg of the desired product with a specific rotation of [α]$_D$= +43.5°±3° (c=0.2% in ethanol).

| IR Spectrum: (CHCl$_3$) | |
|---|---|
| OH | 3600 cm$^{-1}$ |
| C≡C | 3305 cm$^{-1}$ |
| Aromatic | 1582, 1499 cm$^{-1}$ |

| Analysis: | | | |
|---|---|---|---|
| C$_{35}$H$_{53}$NO$_3$; molecular weight = 535.82 | | | |
| Calculated: | % C 78.46 | % H 9.97 | % N 2.61 |
| Found: | 78.5 | 9.9 | 2.4 |

EXAMPLE 56

3-hydroxy-11β-(11-(methyl-isopropyl-amino)-11-oxo-undecyl)-Δ$^{1,3,5(10)}$-estratrien-17β-yl propanoate

Step A

11β-N-methyl-N-isopropyl-Δ$^{1,3,5(10)}$-estratrien-undecanamide 3,17β-dipropanoate To a solution of 0.511 g of the product of Step B of Example 16 in 5.1 ml of pyridine, 0.3 ml of propionyl chloride were added and the mixture was stirred for 105 minutes and 0.1 ml of propionyl chloride was added and the mixtures was stirred for 90 minutes, then poured into 30 g of water and ice. The mixture was extracted with ethyl acetate and the organic phase was washed, dried and distilled to dryness under reduced pressure to obtain 0.848 g of the product that was chromatographed on silica (eluant: cyclohexane-ethyl acetate 6-4).

| IR Spectrum: (CHCl₃) | |
|---|---|
| Absence of OH | |
|  | 1750 cm⁻¹ |
| | 1725 cm⁻¹ |
| | 1624 cm⁻¹ (amide III) |
| Aromatic | 1496 cm⁻¹ |

Step B 3-hydroxy-11β-(11-(methyl-isopropyl amino)-11-oxo-undecyl)-$\Delta^{1,3,5(10)}$-estratrien-17β-yl propanoate To a solution of 0.34 g of the product of Step A in 4 ml of methanol, there were added 55 mg of potassium bicarbonate in solution in 0.4 ml of above. The mixture was stirred for 22 hours at ambient temperature and water was added. The mixture was extracted with methylene chloride and the organic phase was washed, dried and evaporated to dryness under reduced pressure. The 0.304 g of residue were chromatographed on silica (eluant: cyclohexane-ethyl acetate 6-4) to obtain 0.285 g of the desired product.

| IR Spectrum: (CHCl₃) | | |
|---|---|---|
| OH | 3600 cm⁻¹ | |
| Carbamate | 1720 cm⁻¹ | |
| C=O (amide) | 1617 cm⁻¹ | |
| Aromatic | 1582, 1498 cm⁻¹ | |
| Analysis: | | |
| C₃₆H₅₇NO₄; molecular weight = 567.86 | | |
| Calculated: % C 76.14 | % H 10.12 | % N 2.47 |
| Found: 76.4 | 10.3 | 2.3 |

EXAMPLE 57

N,N-bis-isopropyl-17β-hydroxy-3-oxo-$\Delta^{4,9}$-estradien-11β-undecanamide

Step A

N,N-bis-isopropyl-17β-acetyloxy-3-oxo-$\Delta^{4,9}$-estradien-11β-undecanamide

Using the procedure of Step A of Example 3, 1.44 g of 17β-acetyloxy-3-oxo-11-$\Delta^{4,9}$-estradien-undecanoic acid of Step E of Preparation 5 and 2.1 ml of diisopropylamine were reacted to obtain after chromatography on silica (eluant: cyclohexane-ethyl acetate 1-1), 0.533 g of the desired product.

| IR Spectrum: (CHCl₃) | |
|---|---|
| OAC | 1728 cm⁻¹ |
| Dienone | 1654 cm⁻¹ |

Step B

N,N-bis-isopropyl-17β-hydroxy-3-oxo-$\Delta^{4,9}$-estradien-11β-undecanamide

Using the procedure of Step B of Example 1, 248 mg of the compound of Step A were reacted to obtain after chromatography on silica (eluant: cyclohexane-ethyl acetate 1-1), 91 mg of the desired product.

| IR Spectrum: (CHCl₃) | | |
|---|---|---|
| OH | 3618 cm⁻¹ | |
| C=O | 1552, 1442 cm⁻¹ | |
| Amide III | 1620 cm⁻¹ | |
| Analysis: | | |
| C₃₅H₅₇NO₃; molecular weight = 539.85 | | |
| Calculated: % C 77.87 | % H 10.64 | % N 2.59 |
| Found: 77.6 | 10.7 | 2.5 |

EXAMPLE 58

N,N-bis-isopropyl-3,17β-dihydroxy-$\Delta^{1,3,5(10)}$-estratrien-11β-undecanamide Using the procedure of Example 8, 0.952 g of the product of Step A of Example 57 were reacted to obtain after chromatography on silica (eluant: cyclohexane-ethyl acetate 1-1), 302 mg of the desired product.

| IR Spectrum: (CHCl₃) | |
|---|---|
| OH | 3607 cm⁻¹ |
| C=O | 1617 cm⁻¹ (amide III) |
| Aromatic | 1582, 1498 cm⁻¹ |

EXAMPLE 59

3,17β-dihydroxy-α-N-dimethyl-N-isopropyl-$\Delta^{1,3,5(10)}$-estratrien-11β-undecanamide Step A 3,17β-bis-(tetrahydropyranyloxy)-N-methyl-N-isopropyl-$\Delta^{1,3,5(10)}$-estratrien-11β-undecanamide For one hour, a mixture of 1.045 g of the product of Step B of Example 16, 50 ml of ether, 3.75 ml of dihydropyran and 30 mg of p-toluene sulfonic acid was stirred and was then poured into 100 ml of a saturated solution of sodium bicarbonate and was extracted with ether. The ether extract was evaporated to dryness under reduced pressure to obtain 2.216 g of resin which was chromatographed on silica (eluant: methylene chloride-acetone 95-5) to obtain 1.38 g of the desired product.

| IR Spectrum: (CHCl₃) | |
|---|---|
| Absence of OH | |
| C=O | 1621 cm⁻¹ (amide III) |
| Aromatic | 1573, 1497 cm⁻¹ |

Step B 3,17β-dihydroxy-α-N-dimethyl-N-isopropyl-$\Delta^{1,3,5(10)}$-estratrien-11β-undecanamide Using the procedure of Step B of Example 39, 435 mg of the product of Step A were reacted to obtain 430 mg of product, the pyranyls of which were hydrolyzed by stirring in a mixture of 4 ml of ethanol and 4 ml of 2N hydrochloric acid. After concentration to half volume under reduced pressure, and extraction with methylene chloride, and chromatography on silica (eluant: methylene chloride-methanol 95-5), 0.178 g of the desired product having a specific rotation of $[\alpha]_D = +90° \pm 2°$ (c=0.15% in ethanol) were obtained.

| IR Spectrum: (CHCl₃) | |
|---|---|
| OH | 3605 cm⁻¹ |
| C=O | 1615 cm⁻¹ (amide III) |
| Aromatic | 1582, 1498 cm⁻¹ |

EXAMPLE 60

3,17β-dihydroxy-α,α-dimethyl-N-methyl-N-isopropyl-$\Delta^{1,3,5(10)}$-estratrien-11β-undecanamide Using the procedure of Step C of Example 39, 210 mg of product of Step A of Example 59 were reacted to obtain after chromatography on silica (eluant:methylene chloride-acetone 96-5), 103 mg of the desired product with a specific rotation of $[\alpha]_D = +72° \pm 2.5°$ (c=0.5% in ethanol).

| IR Spectrum: (CHC₃) | | | |
|---|---|---|---|
| OH | 3604 cm⁻¹ | | |
| C=O | 1600 cm⁻¹ | | |
| Aromatic | 1580, 1498 cm⁻¹ | | |
| Analysis: | | | |
| C₃₅H₅₇NO₃ | | | |
| Calculated: | % C 77.87 | % H 10.64 | % N 2.59 |
| Found: | 77.9 | 10.8 | 2.5 |

EXAMPLE 61

1-(11-(17β-hydroxy-3-oxo-$\Delta^{4,9}$-estradien-11β-yl)-1-oxo-undecyl)-4-methyl-piperazine

Step A 1-(11-(17β-acetyloxy-3-oxo-$\Delta^{4,9}$-estradien-11β-yl)-1-oxo-undecyl)-4-methyl piperazine Using the procedure of Step A of Example 3, 3.886 g of the acid of Step E of Preparation 5 and 4.33 ml of N-methyl piperazine were reacted to obtain after chromatography on silica (eluant: ethyl acetate-methanol 95-5, then 90-10), 3.14 g of the desired product.

| IR Spectrum: (CHCl₃) | |
|---|---|
| C=O | 1730 cm⁻¹ (OAC) |
| Dienone + N—C=O | 1646 cm⁻¹ |

Step B 1-(11-(17β-hydroxy-3-oxo-$\Delta^{4,9}$-estradien-11β-yl)-1-oxo-undecyl)-4-methyl piperazine Using the procedure of Step B of Example 1, 1.398 g of the product of Step A were reacted to obtain after chromatography on silica (eluant: methylene chloride-methanol 95-5), 1.012 g of the expected product with a specific rotation of $[\alpha]_D = -36° \pm 2.5°$ (c=0.5% in ethanol).

| IR Spectrum: (CHCl₃) | | | |
|---|---|---|---|
| OH | 3615 cm⁻¹ | | |
| C=O | 1642 cm⁻¹ | | |
| Analysis: | | | |
| C₃₄H₅₄N₂O₃; molecular weight = 538.82 | | | |
| Calculated: | % C 75.78 | % H 10.10 | % N 5.20 |
| Found: | 75.9 | 10.1 | 5.1 |

EXAMPLE 62

4-[11-(3,17β-dihydroxy-$\Delta^{1,3,5(10)}$-estratrien-11β-yl)-1-oxo-undecyl]-4-methyl piperazine Using the procedure of Example 2, 1.619 g of the product of Step A of Example 61 were reacted to obtain after two successive chromatographies on silica (eluant: methylene chloride-methanol 95-5), 466 mg of the desired product with a specific rotation of $[\alpha]_D = +70.5° \pm 2.5°$ (c=0.5% in ethanol).

| IR Spectrum: (CHCl₃) | | | |
|---|---|---|---|
| OH | 3610 cm⁻¹ | | |
| Amide III | 1622 cm⁻¹ | | |
| Aromatic | 1582, 1498 cm⁻¹ | | |
| Analysis: | | | |
| C₃₄H₅₄N₂O₃; molecular weight = 538.82 | | | |
| Calculated: | % C 75.78 | % H 10.10 | % N 5.20 |
| Found: | 76.0 | 10.0 | 5.1 |

EXAMPLE 63

N-(2-chloro-2-methylpropyl)-17β-hydroxy-3-oxo-$\Delta^{4,9}$-estradien-11β-undecanamide

Step A

N-(2-chloro-2-methylpropyl)-17β-acetyloxy-3-oxo-$\Delta^{4,9}$-estradien-11β-undecanamide Using the procedure of Step A of Example 3, 2.35 g of the compound of Step E of Preparation 5 and 2.5 ml of 2,2-dimethylaziridine were reacted to obtain after chromatography on silica (eluant: methylene chloride-acetone 92.5-7.5) 0.08 g of the desired product.

| IR Spectrum: (CHCl₃) | |
|---|---|
| =C—NH | 3445 cm⁻¹ |
| OAC | 1728 cm⁻¹ |
| Dienone + Amide II | 1657 cm⁻¹ |
| Amide II | 1517 cm⁻¹ |

Step B

N-(2-chloro-2-methylpropyl)-17β-hydroxy-3-oxo-$\Delta^{4,9}$-estradien-11β-undecanamide Using the procedure of Step B of Example 1, 720 mg of the product of Step A were reacted to obtain after chromatography on silica (eluant: cyclohexane-ethyl acetate 1-1), 420 mg of the desired product with a specific rotation of $[\alpha]_D = -38° \pm 1°$ (c=0.7% in ethanol).

| IR Spectrum: (CHCl₃) | |
|---|---|
| OH | 3610 cm⁻¹ |
| =C—NH | 3444 cm⁻¹ |
| C=O | 1657 cm⁻¹ |
| | (amide II + dienone) |
| Amide II | 1517 cm⁻¹ |

EXAMPLE 64

N-(2-chloro-2-methylpropyl)-3,17beta-dihydroxyestra-1,3,5(10)-trien-11beta-undecanamide

Stage A

N-(2-chloro-2-methylpropyl)-3,17beta-diacetyloxyestra-1,3,5(10)-trien-11beta-undecanamide One operates as in Stage A of Example 8 starting with 970 mg of the product obtained in Example 63 using 1 $cm^3$ of acetyl bromide and 2 $cm^3$ of acetic anhydride. After chromatography on silica (eluant: cyclohexane-ethyl acetate 7-3), one obtains 650 mg of desired product.

| IR Spectrum: (CHCl$_3$) | |
|---|---|
| NH | 3445 $cm^{-1}$ |
| OAc | 1748, 1727 $cm^{-1}$ |
| $\diagdown$C=O$\diagup$ | 1668 $cm^{-1}$ |
| amide II | 1516 $cm^{-1}$ |
| aromatic | 1614, 1580, 1494 $cm^{-1}$ |

Stage B

N-(2-chloro-2-methylpropyl)-3,17beta-dihydroxyestra-1,3,5(10)-trien-11beta-undecanamide.

One operates as in Stage B of Example 8 starting with 640 mg of the product obtained in Stage A above. After chromatography on silica (eluant:cyclohexane-ethyl acetate 6-4) one obtains 512 mg of expected product. [alpha]$_D$= +83°±3° (c=0.5% ethanol)

| IR Spectrum: (CHCl$_3$) | |
|---|---|
| OH | 3604 $cm^{-1}$ |
| =C—NH | 3441 $cm^{-1}$ |
| $\diagdown$C=O$\diagup$ | 1665 $cm^{-1}$ |
| amide II + aromatic | 1619, 1610, 1521, 1499 $cm^{-1}$ |

EXAMPLE 65

3,17beta-dihydroxy-N-methoxy-N-methyl-estra-1,3,5(10)-trien-11beta-undecanamide

Stage A

17beta-acetyloxy-N-methoxy-N-methyl-3-oxo-estra-4,9-dien-11beta-undecanamide

One operates as in Stage A of Example 3 starting with 1.93 g of the product obtained as in Stage E of preparation 5 using 1.3 $cm^3$ of N-O-dimethylhydroxylamine. After chromatography on silica (eluant: cyclohexane-ethyl acetate 1-1), one obtains 1.867 g of the expected product.

| IR Spectrum: (CHCl$_3$) | |
|---|---|
| OAC | 1728 $cm^{-1}$ |
| conjugated ketone + amide III | 1653 $cm^{-1}$ |
| C=C | 1601 $cm^{-1}$ |

Stage B 3,17bis-(acetyloxy)-N-methoxy-N-methyl-estra-1,3,5(10)-trien-11beta-undecanamide One operates as in Stage A of Example 8 starting with 935 mg of the product obtained above using 0.75 $cm^3$ of acetyl bromide and 1.5 $cm^3$ of acetic anhydride. After chromatography on silica (eluant: cyclohexane-ethyl acetate 7-3), one obtains 898 mg of the desired product.

| IR Spectrum: (CHCl$_3$) | |
|---|---|
| acetate | 1727, 1746 $cm^{-1}$ |
| amide III | 1647 $cm^{-1}$ |
| aromatic | 1583, 1494 $cm^{-1}$ |

Stage C 3,17beta-dihydroxy-N-methoxy-N-methyl-estra-1,3,5(10)-trien-11beta-undecanamide One operates as in Stage B of Example 8 starting with 850 mg of product obtained in Stage B above. After chromatography on silica (eluant: cyclohexane-ethyl acetate 6-4), one obtains 630 mg of the desired product. [alpha]$_D$= +92°±2° (c=1% ethanol)

| IR Spectrum: (CHCl$_3$) | | | |
|---|---|---|---|
| OH | 3604 $cm^{-1}$ | | |
| amide III | 1643 $cm^{-1}$ | | |
| aromatic | 1583, 1498 $cm^{-1}$ | | |
| Analysis: C$_{31}$H$_{49}$NO$_4$: 499.74 | | | |
| Calculated: | C % 74.51 | H % 9.88 | N % 2.80 |
| Found: | 74.4 | 10.1 | 2.7 |

EXAMPLE 66

17beta-hydroxy-N-methoxy-N-methyl-3-oxo-estra-4,9-dien-11beta-undecanamide

One operates as in Stage B of Example 1 starting with 770 mg of the product obtained in Stage A of Example 65. After chromatography on silica (eluant: cyclohexane-ethyl acetate 1-1) one obtains 690 mg of the desired product. [alpha]$_D$= -38°±1° (c=0.65% ethanol)

| IR Spectrum: (CHCl$_3$) | | | |
|---|---|---|---|
| OH | 3614 $cm^{-1}$ | | |
| dienone + amide III | 1652 $cm^{-1}$ | | |
| C=C | 1601 $cm^{-1}$ | | |
| Analysis: C$_{31}$H$_{49}$NO$_4$: 499.74 | | | |
| Calculated: | C % 74.51 | H % 9.88 | N % 2.80 |
| Found: | 74.5 | 9.8 | 2.6 |

PREPARATION OF EXAMPLE 67

17beta-acetyloxy-11beta-(11-hydroxy-indecyl)-estra-4,9-dien-3-one

One operates as in preparation 5 (Stages B, C, D) starting with 5.8 g of product obtained in Stage A of preparation 8. After chromatography on silica (eluant: cyclohexane-ethyl acetate 6-4), one obtains 2.847 g of the expected product.

| IR Spectrum: (CHCl$_3$) | |
|---|---|
| OH | 3624 cm$^{-1}$ |
| C=O | 1730 cm$^{-1}$ (OAC) |
| dienone | 1654, 1601 cm$^{-1}$ |

EXAMPLE 67

17beta-hydroxy-N-methyl-N-(1-methylethyl)-3-oxo-estra-4,9-dien-11beta-dodecanamide

Stage A

17beta-acetyloxy-N-methyl-N-(1-methylethyl)-3-oxo-estra-4,9-dien-11beta-dodecanamide One operates as in Stage A of Example 1 starting with 2.847 g of product obtained in the above preparation using 4.8 cm$^3$ of Heilbron-Jones reagent. One obtains 2.787 g of intermediate acid. One carries out the amidification starting with 2 g of this crude acid using 1.6 cm$^3$ of N-methyl isopropylamine. After chromatography on silica (eluant: methylene chloride-acetone 95-5), one obtains 1.8 g of desired product.

| IR Spectrum: (CHCL$_3$) | |
|---|---|
| C=O | { 1728 cm$^{-1}$ (OAC) |
|  | { 1653 cm$^{-1}$ (dienone) |
| C=O | 1621 cm$^{-1}$ (amide III) |

Stage B

17beta-hydroxy-N-methyl-N-(1-methylethyl)-3-oxo-estra-4,9-dien-11beta-dodecanamide One operates as in Stage B of Example 1 starting with 545 mg of the product obtained above. After chromatography on silica (eluant: toluene-triethylamine 95-5), one obtains 420 mg of expected product. [alpha]$_D$= −25°±2° (c=0.5% ethanol)

| IR Spectrum: (CHCl$_3$) | | |
|---|---|---|
| OH | 3613 cm$^{-1}$ | |
| C=O | { 1643 cm$^{-1}$ (dienone) | |
|  | { 1621 cm$^{-1}$ (amide III) | |
| Analysis: C$_{34}$H$_{55}$NO$_3$: 525.82 | | |
| Calculated: | C % 77.46  H % 10.54 | N % 2.66 |
| Found: | 77.4  10.6 | 2.5 |

EXAMPLE 68

3,17beta-dihydroxy-N-methyl-N-(1-methylethyl)-estra-1,3,5(10)-trien-11beta-dodecanamide One operates as in Example 2 starting with 1.276 g of the product obtained in Stage A of Example 67. After chromatography on silica (eluant: toluene-triethylamine 9-1), one obtains 735 mg of desired product. [alpha]$_D$= +86.5°±2.5° (c=0.6% ethanol)

| IR Spectrum: (CHCl$_3$) | |
|---|---|
| OH | 3605 cm$^{-1}$ |
| C=O | 1617 cm$^{-1}$ (amide III) |
| aromatic | 1582, 1498 cm$^{-1}$ |

EXAMPLE 69

(E) 12-(3,17beta-dihydroxy-N-methyl-N-(1-methylethyl)-estra-1,3,5(10)-trien-11beta-yl)-2-dodecanamide

Stage A 10-(17beta-acetoxy-3-oxo-estra-4,9-dien-11beta-yl)-decanal

To a solution of 0.18 cm$^3$ of oxalyl chloride and 5 cm$^3$ of methylene chloride, cooled to −70° C., one adds, drop by drop, a solution of 0.29 cm$^3$ of dimethylformamide in 5 cm$^3$ of methylene chloride. One agitates for 15 minutes at −60° to −70° C. and adds 650 mg of the product obtained in the preparation of Example 50, in solution in 5 cm$^3$ of methylene chloride. One agitates for 30 minutes at −60° C. and adds 2 cm$^3$ of triethylamine. One brings the mixture to ambient temperature, dilutes with water, extracts with methylene chloride, washes with water, dries and evaporates to dryness under reduced pressure. One chromatographs on silica (eluant: cyclohexane-ethyl acetate 7-3) and obtains 580 mg of desired product.

| IR Spectrum: (CHCl$_3$) | |
|---|---|
| C=O aldehyde + acetate | 1723 cm$^{-1}$ |
| dienone | 1655, 1601 cm$^{-1}$ |

Stage B (E) 12-(17beta-acetoxy-N-methyl-N-(1-methylethyl)-3-oxo-estra-4,9-dien-11beta-yl)-2-dodecanamide Preparation of the Phosphorane To a solution of 1 cm$^3$ of N-methyl-N-isopropyl bromacetamide in 20 cm$^3$ of ether one adds 2 g of triphenylphosphine. One agitates the mixture for 3 hours, separates the precipitate by decantation, triturates it in ether, separates it again by decantation, and takes it up in water. One washes the solution obtained with ether and alkalizes it with 2N soda, one extracts with ether, dries and evaporates to dryness under reduced pressure. One obtains 980 mg of expected phosphorane. From the ethereal liquors one recovers an additional 1.190 g of phosphorane.

Condensation

To a solution of the aldehyde obtained in Stage A above in 5 cm$^3$ of tetrahydrofuran one adds a solution of 653 mg of phosphorane, obtained previously, in 6 cm$^3$ of tetrahydrofuran. One leaves the mixture for 43 hours at ambient temperature, evaporates the solvent and chromatographs the residue on silica (eluant: cyclohexane-ethyl acetate 1-1). One obtains 580 mg of the desired product.

| IR Spectrum: (CHCl₃) | |
|---|---|
| OAC | 1728 cm⁻¹ |
| dienone | 1655 cm⁻¹ |
| conjugated amide | 1600 cm⁻¹ |

Stage C (E)
12-(3,17beta-dihydroxy-N-methyl-N-(1-methylethyl)-estra-1,3,5(10)-trien-11beta-yl)-2-dodecanamide One operates as in Example 8 starting with 580 mg of the compound obtained in Stage B. After chromatography on silica (eluant: ethyl acetate-cyclohexane 1-1), one obtains 430 mg of desired product.

| IR Spectrum: (CHCl₃) | | | |
|---|---|---|---|
| OH | 3604 cm⁻¹ | | |
| conjugated amide III | 1655, 1597 cm⁻¹ | | |
| aromatic bands | 1498 cm⁻¹ | | |
| Analysis: C₃₄H₅₃NO₃: 523.81 | | | |
| Calculated: | C % 77.96 | H % 10.19 | N % 2.67 |
| Found: | 77.8 | 10.3 | 2.4 |

PREPARATION OF EXAMPLE 70

3-(1,2-ethanediyl cyclic acetal) of 5alpha-hydroxy-11beta-(12-hydroxy-dodecyl)-estr-9-en-3,17-dione One agitates, for 3 hours, 4.2 g of the compound obtained in Stage A of preparation 8 with 29 cm³ of a 1M solution of tetrabutylammonium fluoride. One adds 200 cm³ of a sodium bicarbonate solution, agitates for 30 minutes, then extracts with methylene chloride. One evaporates to dryness and chromatographs the residue (6.27 g) on silica (eluant: methylene chloride-acetone 9-1). One obtains 2.43 g of the desired product.

| IR Spectrum: (CHCl₃) | |
|---|---|
| OH | 3602 cm⁻¹ |
| C=O | 1733 cm⁻¹ |

EXAMPLE 70

3,17beta-dihydroxy-N-methyl-N-(1-methylethyl)-estra-1,3,5(10)-trien-11beta-tridecanamide Stage A (5alpha, 11beta)-3-(1,2-ethanediyl cyclic acetal) of 5-hydroxy-11-[12-[phenylmethyl sulphonyloxy]-dodecyl]-estr-9-en-3,17-dione One operates as in Stage A of Example 40 starting with 3.65 g of the compound obtained in the above preparation using 5 g of paratoluenesulphonyl chloride. After chromatography on silica (eluant: methylene chloride-acetone 9-1) one obtains 3.54 g of expected product, used just as it is for the following stage.

Stage B (5alpha,11beta)-3-(1,2-ethanediyl cyclic acetal) of 5-hydroxy-11-[12-[iodo]-dodecyl]-estr-9-en-3,17-dione One operates as in Stage B of Example 40 starting with 3.5 of the product obtained in Stage A using 1.17 g of sodium iodide. One obtains 4.199 g of the desired product.

| IR Spectrum: (CHCl₃) | |
|---|---|
| OH | 3506 cm⁻¹ |
| C=O | 1733 cm⁻¹ |

Stage C

13-[(5alpha,11beta)-3-(1,2-ethanediyl cyclic acetal) of 5-hydroxy-11beta-yl]-tridecane nitrile One operates as in Stage C of Example 40 starting with 4.19 g of the compound obtained in Stage B above using 1.1 g of potassium cyanide. After chromatography on silica (eluant: cyclohexane-ethyl acetate 6-4), one obtains 2.423 g of the expected product.

| IR Spectrum: (CHCl₃) | |
|---|---|
| OH | 3504 cm⁻¹ |
| C≡N | 2388 cm⁻¹ |
| C=O | 1733 cm⁻¹ |

Stage D

13-[11beta-yl-estra-4,9-dien-3,17-dione]-tridecane nitrile

One operates as in Stage B of preparation 2 starting with 2.4 g of the product obtained in Stage C above. One obtains 2.11 g of the desired compound.

Stage E

13-[3-acetyloxy-17-oxo-1,3,5(10)-trien-11beta-yl]-tridecanediyl

One operates as in Stage B of Example 3 starting with 2.04 g of the product obtained in the previous Stage D. After chromatography on silica (eluant: cyclohexane-ethyl acetate 5-5), one obtains 2 fractions, A=1.1 g and B=0.817 g, of desired product.

| IR Spectrum: (CHCl₃) on fraction A | |
|---|---|
| C≡N | 2240 cm⁻¹ |
| C=O | 1735 cm⁻¹ |
| | 1758 cm⁻¹ (ep) |
| aromatic | 1607, 1581, 1493 cm⁻¹ |

Stage F 3-isobutylcarbonyloxy-N-butyl-N-methyl-17-oxo-estra-1,3,5(10)-trien-11beta-tridecanamide One operates as in Stage E of Example 40 starting with 0.817 g of the product B obtained in the previous stage using 0.54 cm³ of N-methylisobutylamine. After chromatography on silica (eluant: cyclohexane-ethyl acetate 7-3), one obtains 603 mg of the desired product.

| IR Spectrum: (CHCl₃) | |
|---|---|
| C=O | 1753, 1735, 1621 cm⁻¹ |

Stage G 3-isobutylcarbonyloxy-17beta-hydroxy-N-butyl-N-methyl-1,3,5(10)-trien-11beta tridecanamide One operates as in a) of Stage F of Example 40 starting with 573 mg of the compound obtained in Stage F above using 406 mg of tritertbutoxy alumino hydride. After chromatography on silica (eluant: cyclohexane-ethyl acetate 7-3), one obtaines 325 mg of desired product.

| IR Spectrum: (CHCl$_3$) | |
|---|---|
| C=O | 1756 cm$^{-1}$ |
| amide III | 1621 cm$^{-1}$ |
| aromatic | 1494 cm$^{-1}$ |

Stage H 3,17beta-dihydroxy-N-methyl-N-(1-methylethyl)-estra-1,3,5(10)-trien-11beta-tridecanamide One operates as in Stage B of Example 2 starting with 283 mg of the product obtained in Stage G above. After chromatography on silica (eluant: cyclohexane-ethyl acetate 4-6), one obtains 215 mg of the expected product. [alpha]$_D$=−17°±1° (c=1% ethanol)

| Analysis: C$_{35}$H$_{57}$NO$_3$: 539.85 | | | |
|---|---|---|---|
| Calculated: | C % 79.38 | H % 9.54 | N % 2.50 |
| Found: | 79.3 | 9.7 | 2.5 |

PREPARATION OF EXAMPLE 71

[(8-bromooctyl)-oxy]-dimethyl-(1,1-dimethylethyl)-silane

One operates as in preparation 13 starting with 3.97 g of 8-bromooctanol, 19 cm$^3$ of dimethylformamide, 1.55 g of imidazole and 3.32 g of dimethyl tertbutyl chlorosilane. After chromatography on silica (eluant: cyclohexane-toluene 8-2), one obtains 5.4 g of the expected product.

PREPARATION B OF EXAMPLE 71 bromo-N-methyl-N-(1-methyl-ethyl-acetamide

To a solution of 10 cm$^3$ of acetyl bromide in 150 cm$^3$ of ether, cooled to −20° C., one adds a solution of 26 cm$^3$ of methylisopropylamine in 100 cm$^3$ of ether. One leaves the mixture to return to 20° C. and agitates it for 30 minutes at 20° C. One dilutes with water, decants, extracts with ether, dries and separates by distillation. One obtains 13 g of expected product. B.p.=71°/72° under 1 mmHg.

PREPARATION C OF EXAMPLE 71

11beta-(8-hydroxyethyl)-estra-4,9-dien-3,17-dione

Stage A 3-(1,2-ethanediyl) cyclic acetal of 11beta-[8-(dimethylethyl)(1,1-dimethylethyl)-silyloxy]-octyl-5alpha-hydroxy-estr-9-en-3,17-dione One operates as in Stage A of preparation 1 starting with 3.96 g of 3-(1,2-ethanediyl) cyclic acetal) of 5alpha, 10alpha-epoxy-estr-9,11-en-3,17-dione obtained according to EP 0057115 (Ex. 7) using 5.4 g of [(8-bromooctyl)-oxy]-dimethyl-(1,1-dimethylethyl)-silane (preparation A of Example 71), 1 g of magnesium turnings and 0.4 g of copper chloride. After chromatography on Lichrosorb Rp18 (eluant: methanol-water 9-1), one obtains 3.85 g of the expected compound used just as it is for the following stage.

Stage B

11beta-(8-hydroxyoctyl)-estra-4,9-dien-3,17-dione

One operates as in Stage A of preparation 6 starting with 1.77 g of the product obtained above. After chromatography on silica (eluant: methylene chloride-ethyl acetate 1-1), one obtains 1.08 g of the desired compound.

| IR Spectrum: (CHCl$_3$) | |
|---|---|
| OH | 3624 cm$^{-1}$ |
| C=O | 1735 cm$^{-1}$ (17-keto) |
| | 1656, 1602 cm$^{-1}$ (dienone) |

EXAMPLE 71

[[8-(3,17beta-dihydroxy-estra-1,3,5(10)-trien-11beta-yl)-octyl]-oxy]-N-methyl-N-(1-methylethyl)-acetamide

Stage A

[[8-(3,17-dioxo-estra-4,9-dien-11beta-yl)-octyl]-oxy]-N-methyl-N-(1-methylethyl)-acetamide To a solution of 570 mg of the compound obtained in the above preparation in 10 cm$^3$ of tetrahydrofuran one adds 1.4 cm$^3$ of bromo-N-methyl-N-(1-methylethyl)-acetamide (obtained in preparation B of Example 71) and 285 mg of sodium iodide, then 140 mg of 50% sodium hydride in oil. One agitates for one hour, pours the mixture into an N hydrochloric acid solution at 0° C. and extracts with methylene chloride. One evaporates to dryness and chromatographs the residue (2 g) on silica (eluant: ethyl acetate-ether 8-2). One obtains 350 mg of the desired product.

| IR Spectrum: (CHCl$_3$) | |
|---|---|
| 17-keto | 1736 cm$^{-1}$ |
| 3-keto | 1655 cm$^{-1}$ |
| amide III | 1628 cm$^{-1}$ |
| C=C | 1603 cm$^{-1}$ |

Stage B

[[8-(3,17beta-dihydroxy-estra-1,3,5(10)-trien-11beta-yl)-octyl]-oxy]-N-methyl-N-(1-methylethyl) acetamide One operates as in Stages B and C of Example 3 starting with 850 mg of the product obtained in Stage A above. After chromatography on silica (eluant: ethyl acetate-hexane 75-25), one obtains 442 mg of product that one recrystallizes from ethyl acetate. One collects in this way 402 mg of desired product. M.p.=126° C.

| IR Spectrum: (CHCl$_3$) | | |
|---|---|---|
| OH | 3605 cm$^{-1}$ | |
| C=O | 1626 cm$^{-1}$ | |
| aromatic | 1583, 1498 cm$^{-1}$ | |
| Analysis: C$_{32}$H$_{51}$NO$_4$: 513.77 | | |
| Calculated: | C% 74.81 H% 10.0 | N% 2.72 |
| Found: | 74.5 9.8 | 2.5 |

PREPARATION OF EXAMPLE 72

Stage A (1,2-ethanediyl cyclic acetal) of 5alpha, 17betadihydroxy-11beta-[11-[dimethyl-(1,1-dimethylethyl)-silyl]-oxy]-undecyl-17alpha-pregna-9-en-20-yne One operates as in Stage C of Example 21 starting with 4 g of the product obtained in Stage A of preparation 5 using 80 cm$^3$ of ethylenediamine and 5.97 g of lithium acetylide-ethylenediamine complex. After chromatography on silica (eluant: methylene chloride-acetone 95-5), one obtains 2.024 g of desired product.

| IR Spectrum: (CHCl$_3$) | |
|---|---|
| OH in position 5 and 17 | 3600, 3500 cm$^{-1}$ |
| C≡C | 3305 cm$^{-1}$ |
| OSi band | 836 cm$^{-1}$ |

Stage B

17beta-hydroxy-11beta-(11-hydroxyundecyl)-17alpha-pregna-4,9-dien-20-yn-3-one

One operates as in Stage A of preparation 6 starting with 1.05 g of product obtained in Stage A above. After chromatography on silica (eluant: methylene chloride-acetone 9-1), one obtains 0.712 g of desired product.

| IR Spectrum: (CHCl$_3$) | |
|---|---|
| OH | 3608 cm$^{-1}$ |
| C≡CH | 3304 cm$^{-1}$ |
| dienone | 1652, 1598 cm$^{-1}$ |

EXAMPLE 72

17beta-hydroxy-N-methyl-N-(1-methylethyl)-3-oxo-17alpha-pregna-4,9-dien-20-yn-11beta-undecanamide One operates as in Stage A of Example 1 starting with 1.3 g of the product obtained in Stage B of the above preparation using 2.5 cm$^3$ of Heilbron-Jones reagent, 3.11 g of barium carbonate, then 0.9 cm$^3$ of isopropylmethylamine. After chromatography on silica (eluant: methylene chloride-acetone 9-1), one obtains 0.336 g of the desired product.

| IR Spectrum: (CHCl$_3$) | | | |
|---|---|---|---|
| OH | 3600 cm$^{-1}$ | | |
| C≡CH | 3305 cm$^{-1}$ | | |
| C=O | 1651, 1621 cm$^{-1}$ | | |
| Analysis: C$_{35}$H$_{53}$NO$_3$: 535.82 | | | |
| Calculated: | C% 78.46 | H% 9.97 | N% 2.61 |
| Found: | 78.5 | 9.9 | 2.4 |

EXAMPLE 73

N-butyl-17beta-hydroxy-3-methoxy-N-methyl-estra-1,3,5(10)-trien-11beta-undecanamide To a solution of 194 mg of the product obtained in Example 13 in 3 cm$^3$ of acetone one adds 0.2 cm$^3$ of 2N soda. One agitates for 10 minutes at ambient temperature, then one adds 0.5 cm$^3$ of an acetone solution of dimethyl sulphate prepared with 0.3 cm$^3$ of dimethyl sulphate and enough acetone for 10 cm$^3$. One agitates for 10 minutes at ambient temperature and adds 0.5 cm$^3$ of dimethyl sulphate solution. After 20 minutes, one adds 0.2 cm$^3$ of 2N soda then 1 cm$^3$ of dimethyl sulphate solution. After 20 minutes, one adds another 0.2 cm$^3$ of 2N soda then 1 cm$^3$ of dimethyl sulphate solution. One agitates again for 30 minutes, dilutes with an ammonium chloride solution and extracts with ethyl acetate. One evaporates to dryness and chromatographs the residue (220 mg) on silica (eluant: cyclohexane-ethyl acetate 1-1) and one obtains 190 mg of desired product.

| IR Spectrum: (CHCl$_3$) | | | |
|---|---|---|---|
| OH | 3612 cm$^{-1}$ | | |
| C=O | 1626 cm$^{-1}$ | | |
| aromatic | 1574, 1500 cm$^{-1}$ | | |
| Analysis: C$_{35}$H$_{57}$NO$_3$: 539.85 | | | |
| Calculated: | C% 77.87 | H% 10.64 | N% 2.59 |
| Found: | 77.7 | 10.8 | 2.5 |

EXAMPLE 74

N-butyl-4-(17beta-hydroxy-3-methoxy-estra-1,3,5(10)-trien-11beta-yl)-N-methyl benzene octanamide To a solution of 862 mg of the product obtained in Example 8 in 8.6 cm$^3$ of hexamethylphosphotriamide one adds 1.54 cm$^3$ of N soda, then drop by drop 218 mg of methyl iodide. One agitates for one hour at ambient temperature, one adds 1.5 cm$^3$ of N soda, dilutes with water, extracts with ethyl acetate, washes, dries and brings to dryness under reduced pressure. One collects 1.017 g of product that one chromatographs on silica (eluant: toluene-triethylamine 9-1) and obtains 592 mg of desired product. [alpha]$_D$= −38.5°±2.5° (c=0.5% ethanol)

| IR Spectrum: (CHCl$_3$) | | | |
|---|---|---|---|
| OH | 3610 cm$^{-1}$ | | |
| C=O | 1626 cm$^{-1}$ | | |
| aromatic | 1570, 1501 cm$^{-1}$ | | |
| Analysis: C$_{38}$H$_{55}$NO$_3$: 573.87 | | | |
| Calculated: | C% 79.53 | H% 9.66 | N% 2.43 |
| Found: | 79.3 | 9.9 | 2.4 |

PREPARATION OF EXAMPLE 75

N-heptafluorobutyl-N-methylamine hydrochloride

One cools to 0° C. 100 cm$^3$ of anhydrous ether, 100 cm$^3$ of anhydrous tetrahydrofuran, then bubbles through methylamine for 10 minutes. Over half an hour, one introduces 44.98 g of heptafluorobutyric anhydride, continuing to gently bubble the methylamine through it. One agitates the mixture for 2 hours, leaving it to return to ambient temperature. One distils to a small volume under reduced pressure, takes up in 200 cm$^3$ of anhydrous tetrahydrofuran and slowly introduces 30 cm$^3$ of diborane-dimethyl sulphide complex. One refluxes the mixture for 16 hours, then cools to it ambient temperature and slowly introduces 200 cm$^3$ of methanol. Next one bubbles through gaseous hydrochloric acid for 15 minutes. One refluxes for one hour then distils the solvents under reduced pressure. One takes up the residue in 200 cm$^3$ of methanol. Again one bubbles through gaseous hydrochloric acid for 10 minutes then refluxes for 2 hours. One distils the solvent, agitates for 10 minutes in 100 cm$^3$ of ice-cooled 6N hydrochloric acid. One separates, washes with 2N hydrochloric acid, dries and obtains 22.699 g of expected product. The hydrochloride obtained above is purified by crystallization from 140 cm$^3$ of ethanol. One then adds 140 cm$^3$ of ether, agitates for half an hour, separates, washes with ether and dries under reduced pressure. One obtains 21.7 g of desired product (sublimating at about 200° C.).

Analysis: $C_5H_6F_7N \cdot HCl$: 249.56

| | C% | H% | Cl% | F% | N% |
|---|---|---|---|---|---|
| Calculated: | 24.06 | 2.83 | 14.20 | 53.29 | 5.61 |
| Found: | 24.0 | 2.8 | 14.4 | 52.3–52.1 | 5.6 |

EXAMPLE 75

3,17beta-dihydroxy-N-(2,2,3,3,4,4,4-heptafluorobutyl)-N-methyl-estra-1,3,5(10)-trien-11beta-undecanamide

Stage A 3,17-dioxo-N-(2,2,3,3,4,4,4-heptafluorobutyl)-N-methyl-estra-4,9-dien-11beta-undecanamide One operates as in Stage A of Example 3 starting with 500 mg of the compound obtained in Stage B of preparation 6 using 0.370 cm³ of N-methylmorpholine, 0.173 cm³ of isobutyl chloroformate and 412 mg of heptafluorobutylmethylamine hydrochloride (preparation of Example 75). After chromatography on silica (eluant:essence G-ethyl acetate 6-4, pure ethyl acetate, then ethyl acetate with 1% acetic acid) one obtains 180 mg of the desired product.

| IR Spectrum: (CHCl₃) | |
|---|---|
| C=O | 1736 cm⁻¹ (17-keto) |
| | 1657 cm⁻¹ (dienone + amide III) |
| C=C | 1602 cm⁻¹ |

Stage B 3-acetoxy-17-oxo-N-(2,2,3,3,4,4,4-heptafluorobutyl)-N-methyl-estra-1,3,5(10)-trien-11beta-undecanamide One operates as in Stage B of Example 3 starting with 345 mg of the product obtained in Stage A above using 0.4 cm³ of acetic anhydride and 0.2 cm³ of acetyl bromide. One obtains 323 mg of expected product.

Stage C 3,17beta-dihydroxy-N-(2,2,3,3,4,4,4-heptafluorobutyl)-N-methyl-estra-1,3,5(10)-trien-11beta-undecanamide One operates as in Stage C of Example 3 starting with 323 mg of the product obtained above using 20 mg of boron and sodium hydride and 0.3 cm³ of 2N soda. After chromatography on silica (eluant:essence G-ethyl acetate 1-1), one obtains 230 mg of the expected product.

| IR Spectrum: (CHCl₃) | |
|---|---|
| OH | 3604 cm⁻¹ |
| C=O | 1655 cm⁻¹ |
| aromatic | 1610, 1584, 1498 cm⁻¹ |

Analysis: $C_{34}H_{48}F_7NO_3$: 651.76

| | C% | H% | N% | F% |
|---|---|---|---|---|
| Calculated: | 62.66 | 7.42 | 2.15 | 20.4 |
| Found: | 62.7 | 7.6 | 2.0 | 20.04 |

EXAMPLE 76

N-butyl-(5-(4-(3,17beta-dihydroxy-19-nor-17alpha-pregna-1,3,5(10)-trien-20-yn-11beta-yl)-phenoxy)-pentylthio)-N-methyl acetamide One operates as in Example 43 starting with 11beta-4-(hydroxyphenyl)-estra-4,9-dien-3,17-dione and (5-bromopentyl)-thio-N-butyl-N-methyl acetamide, to obtain N-butyl(5-(4-(3-hydroxy-17-oxo-estra-1,3,5(10)-trien-11beta-yl)-phenoxy)-pentylthio)-N-methyl acetamide. The addition of acetylene in the presence of potassium tertbutylate leads to the expected product. [alpha]$_D$ = −98.5° (c=1% CHCl₃)

| IR Spectrum: (CHCl₃) | |
|---|---|
| OH | 3599 cm⁻¹ |
| ethynyl | 3305 cm⁻¹ |
|  | 1628 cm⁻¹ |
| aromatic | 1581, 1512 cm⁻¹ |
| Ultra violet: (EtOH) | |
| max 281 nm epsilon = 4000 | |
| max 287 nm epsilon = 3800 | |
| (EtOH + NaOH N/10) | |
| max 280 nm epsilon = 3300 | |
| max 287 nm epsilon = 3500 | |
| max 300 nm epsilon = 3200 | |

EXAMPLE 77

N-butyl-(5-(4-(3,17beta-dihydroxy-estra-1,3,5(10)-trien-11beta-yl)-phenoxy)-pentylthio)-N-methyl acetamide One reduces the N-butyl-(5-(4-(3-hydroxy-17-oxo-estra-1,3,5(10)-trien-11beta-yl)-phenoxy)-pentylthio)-N-methyl acetamide obtained in Example 76 using sodium borohydride in methanol. In this way one obtains the expected product. [alpha]$_D$ = −32.5° (c=0.1% CHCl₃)

| IR Spectrum: (CHCl₃) | |
|---|---|
| OH | 3603 cm⁻¹ + associated OH |
|  | 1627 cm⁻¹ |
| aromatic | 1581, 1511 cm⁻¹ |
| Ultra violet (EtOH) | |
| max 281 nm epsilon = 3800 | |
| max 287 nm epsilon = 3700 | |
| (EtOH + NaOH N/10) | |
| max 280 nm epsilon = 3100 | |
| max 287 nm epsilon = 3200 | |
| max 300 nm epsilon = 2700 | |

Pharmaceutical Compositions

One prepared tablets corresponding to the following formula:

| Product of Example 21 | 50 mg |
|---|---|
| Excipient (talc, starch, magnesium stearate) q.s. for a tablet completed at | 120 mg |

Pharmaceutical Compositions

Compressed tablets were prepared containing 50 mg of the product of Example 21 and sufficient excipient of talc, starch, magnesium stearate for a tablet weighing 120 mg.

PHARMACOLOGICAL DATA

A-Activity on Hormonal Receptors

Mineralocorticoid Receptor of the Rats' Kidney

Male Sprague-Dawley EOPS rats weighing 140 to 160 g were subjected to supraenalectomy 4 to 8 days earlier and were sacrificed and their kidneys were perfused in situ with 50 ml of a 10 mM Tris, 0.25M saccharose, HCl buffer pH 7.4. The kidneys were then removed, decapsulated and homogenized at 0° C. with the aid of a Potter teflon-glass (1 g of tissue for 3 ml of buffer). The homogenate was centrifuged for 10 minutes at 800 mg and 0° C. and then to eliminate the fixation of the tritiated aldosterone upon the glucocorticoid receptor, 11$\beta$-,17$\beta$-dihydroxy-21-methyl-$\Delta^{1,4,6}$-pregnatrien-20-yn-3-one which was fixed uniquely upon the glucocorticoid receptor was added to the supernatant at a final concentration of $10^{-6}$M. This supernatant was ultracentrifuged at 105,000 g for 60 minutes at 0° C. and aliquotes of the supernatant thus obtained were incubated at 0° C. with a constant concentration (T) of tritiated aldosterone in the presence of increasing concentrations (0–2500.$0^{-9}$M) of the cold aldosterone or the cold product to be studied. After an incubation time (t), the concentration of bound tritiated aldosterone (B) was measured by the adsorption on dextran carbon technique.

Androgen Receptor of Rat's Prostate

Male Sprague Dawley EPOS rats weighing 160 to 200 g were castrated and 24 hours after the castration, the animals were killed. Their prostates were removed, weighed and homogenized at 0° C. using a Potter teflon-glass in a TS buffered solution (Tris 10 mM, saccharose 0.25M, HCl pH 7.4) (1 g of tissue for 5 ml of TS). The homogenate was ultracentrifuged (105,000 g for 60 minutes) at 0° C. and aliquots of the supernatant were incubated at 0° C. for an incubation time E with a constant concentration (T) of tritiated testosterone in the presence of increasing concentrations (0–1000.$10^{-9}$M) either of cold testosterone or of the product to be tested. The concentration of bound tritiated testosterone (B) was then measured in each incubate by the adsorption on dextran carbon technique.

Progestogen Receptor of Rabbit's Uterus

Impuberal rabbits weighing about 1 kg received a cutaneous application of 25 μg of estradiol and 5 days after this treatment, the animals were killed. The uteri were removed, weighed and homogenized at 0° C. using a Potter teflon-glass in a TS buffered solution (Tris 10 mM, Saccharose 0.25M, HCl pH 7.4) (1 g of tissue for 50 ml of TS). The homogenate was then ultracentrifuged (150,000 g×90 minutes) at 0° C. and aliquots of the supernatant were incubated at 0° C. for a time t, with a constant concentration (T) of the tritiated product R (17,21-dimethyl-19-nor-$\Delta^{4,9}$-pregnandiene-3,20-dione in the presence of increasing concentrations (0–2500.$10^{-9}$M) either of cold R or of cold progesterone, or of the cold product to be tested. The concentration (B) of bound tritiated R was subsequently measured in each incubate by the technique of adsorption on dextran charcoal.

Glucocorticoid Receptor of Rat Thymus

Male Sprague Dawley EOPS rats weighing 160 to 200 g were subjected to suprarenalectomy and 4 to 8 days after this intervention, the animals were killed. The thymuses were removed and homogenized at 0° C. in a 10 mM Tris, 0.25M saccharose, 2 mM dithithreitol, HCL pH 7.4 buffer, with the aid of a Potter polytetrafluoroethylene-glass (1 g of tissue for 10 ml of TS). The homogenate was subsequently ultracentrifuged (105,000 g×90 min) at 0° C. and aliquots of the supernatant were incubated at 0° C. for a time (t) with a constant concentration (T) of tritiated dexamethasone in the presence of increasing concentrations (0–2,500.$10^{-9}$M) either of cold dexamethasone, or of cold product to be tested. The concentration (B) of the bound tritiated dexamethasone was measured in each incubate by the adsorption technique on dextran carbon.

Estrogenic Receptor of Mouse Uterus

Impuberal female mice aged from 18 to 21 days were killed and their uteri were removed, then homogenized at 0° C. with the aid of a Potter teflon-glass in a TS buffered solution (10 mM Tris, 0.25M saccharose, HCL pH 7.4) (1 g of tissue for 25 ml of TS). The homogenate was ultracentrifuged (105,000 g×90 min) at 0° C. and aliquots of the supernatant were incubbated at 0° C. or at 25° C. for a time (t) with a constant concentration (T) of tritiated estradiol in the presence of increasing concentrations (0–1000×$10^{-9}$M) either of cold estradiol, or of the cold product to be tested. The concentration (B) of bound tritiated estradiol was measured in each incubate by the technique of adsorption on dextran carbon.

Calculation of the Relative Affinty of the Bond

The calculation of the Relative Affinity of the Bond (RAB) was identical for all the receptors. The following 2 curves were traced; the percentage of the bound tritiated hormone B/T was a function of the logarithm of the concentration of the cold reference hormone and B/T as a function of the logarithm of the concentration of the cold product tested.

One determined the straight line of the equation $$I_{50} = (B/T\max + B/T\min)/2.$$

B/T max = percentage of the bound tritiated hormone for an incubation of this tritiated hormone at the concentration (T).

B/T min = percentage of the bound tritiated hormone for an incubation of this tritiated hormone at the concentration (T) in the presence of a great excess of cold hormone (2500×$10^{-9}$M).

The intersections of the straight line $I_{50}$ and of the curves make it possible to evaluate the concentrations of the cold reference hormone (CH) and of the tested cold product (CX) which inhibit to an extent of 50% the binding of the tritiated hormone upon the receptor. The relative affinity of the bond (RAB) of the tested product is determined by the equation $$RAB = 100(CH)/(CX)$$

The results obtained are as follows:

| Incubation period at 0° C. | Mineralo corticoid | | Androgen | | Progestogen | | Glucocoticoid | | Oestrogen | |
|---|---|---|---|---|---|---|---|---|---|---|
| Product Examples | 1 H | 24 H | 0.5 H | 25 H | 2 H | 24 H | 4 H | 24 H | 2 H | 5 H |
| 8 | 0.09 | 0.09 | 0 | 0.06 | 2.3 | 9 | 4.5 | 8 | 0.12 | 23 |
| 13 | 0.19 | 0.08 | 0 | 0.12 | 0.8 | 1.8 | 7 | 7 | 0.13 | 27 |
| 16 | 0 | 0 | 0 | 0.4 | 0.5 | 2 | 12 | 11 | 0.5 | 50 |
| 21 | 0.4 | 0.5 | 0 | 0 | 0.3 | 1 | 2 | 2.5 | 0.05 | 7.4 |
| 24 | 0 | 0 | 0 | 0.4 | 0 | 0 | 2 | 3 | 0.02 | 13 |
| 17 | 2 | 0.5 | 0.12 | 1.2 | 8 | 15 | 3 | 6 | 0.1 | <0.01 |
| 19 | 0.7 | 0.1 | 11 | 11 | 6 | 7 | 5 | 4.5 | 0.3 | 0.8 |
| 22 | 0 | 0 | 0.8 | 0 | 12 | 21 | 7 | 14 | <0.01 | <0.01 |
| 35 | | | | | | | | | 0.13 | 12 |
| 37 | | | | | | | | | 0.6 | 28 |
| 43 | | | | | | | | | 4.0 | 3,0 |
| 46 | | | | | | | | | 0.3 | 65 |
| 55 | | | | | | | | | 1.2 | 45 |
| 71 | | | | | | | | | 0.6 | 50 |

Conclusion

The products studied, particularly the products of Examples 8, 13, 16, 37, 46, 55 and 71 had a marked affinity for the estrogen receptors at the second time. The product of Example 19 had a moderate affinity for the androgen receptor and the products of Examples 17 and 22 for the pregesterone receptor. Furthermore, the majority of the products are free of uterotrophic activity.

B. Anti-Proliferative Activity of the Products of the Invention Upon the Growth of MCF-7 Mammary Tumoral Cells

Description of the Test a) Cell Culture

The MCF-7 strains were kept under culture in FCS(1) medium at 37° C. under a humid atmosphere containing 5% $CO_2$ and the cells at subconfluence were harvested by trypsination (0.05% trypsine, 0.02% EDTA), then rinsed by gentle centrifugation. A sample of the cells in suspension was counted on Malassez cell.

b) Growth Study

The cells, resuspended in FCS medium, were seeded at a rate of 30,000 cells per pit in multi-pit plates (24 pits of 2.5 cm$^2$) and twenty four hours after seeding (DO), the product to be tested was added to the medium in ethanolic solution (final concentration in ethanol: 0.1%), at a concentration of $10^{-12}$ to $10^{-6}$M, the control pits receiving the same concentration of ethanol. The media were renewed every 48 hours and at the end of the experiment (D6), the medium was sucked off and the cells were immediately fixed with 150 microliters of methanol to estimate the DNA. The anti-proliferative activity of the products was evaluated by their capacity to inhibit the increase of DNA.

c) Measurement of DNA

The DNA was measured by a fluorimetric method employing DABA (3,5-diaminobenzoic acid) (2): 150 microliters of DABA were added to each of the pits and the plates were then incubated for 45 minutes at 56° C., then 2 ml of 1N HCl were added. The fluorescence was measured with the aid of a fluorimeter (length of the exiting wave: 408 nm, length of the emitting wave: 501 nm). The quantity of DNA per pit was evaluated with reference to a standard scale obtained by treating a standard DNA from calf thymus under the same conditions.

Results

The concentration in nM which inhibited the growth of MCF$_7$ to an extent of 50% ($IC_{50}$) was determined in the manner indicated below:

Results

Product of Example 8: $IC_{50}$=0.04 nM
Product of Example 13: $IC_{50}$=0.5 nM
Product of Example 16: $IC_{50}$=0.02 nM
Product of Example 21: $IC_{50}$=0.02 nM
Product of Example 24: $IC_{50}$=0.06 nM
Product of Example 35: $IC_{50}$=0.04 nM
Product of Example 37: $IC_{50}$=0.03 nM
Product of Example 43: $IC_{50}$=0.002 nM
Product of Example 46: $IC_{50}$=0.006 nM
Product of Example 55: $IC_{50}$=0.01 nM
Product of Example 71: $IC_{50}$=0.1 nM Furthermore, the maximum inhibitor effect of the products reached about 90%.

(1) The fetal calf serum (FCS) culture medium was prepared as follows: MEM medium (minimal essential medium) to which were added:
Non-essential amino acids (GIBCO),
Peni-strepto (100 U/ml penicillin, 0.1 mg/ml streptomycin),
Fungizone 0.1%
Insulin (50 ng/ml),
Fetal calf serum containing no steroids (10% final concentration).

(2) Puzas and Goodman, Analytical Biochemistry, Vol. 86, pp. 50, 1978.

Various modifications of the products and method of the invention may be made without departing from the spirit or scope thereof and it is to be understood that the invention is intended to be limited only as defined in the appended claims.

What we claim is:
1. Novel 19-nor-steroids of the formula

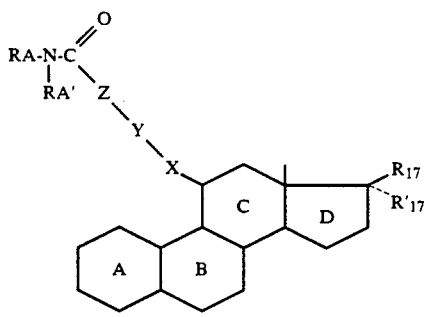

wherein the A and B rings have a structure

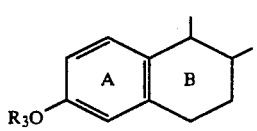

$R_3$ is selected from the group consisting of hydrogen, alkyl of 1 to 4 carbon atoms and acyl of an organic carboxylic acid of 1 to 7 carbon atoms, $R_{17}$ and $R'_{17}$ together form =O or $R_{17}$ is —OH or acyloxy and $R'_{17}$ is selected from the group consisting of hydrogen, alkyl of 1 to 8 carbon atoms and alkenyl and alkynyl of 2 to 8 carbon atoms, all optionally substituted with at least one member of the group consisting of halogen, alkoxy, alkylthio, —$NH_2$, mono- or dialkylamino, optionally oxidized amino-alkyl, dialkylaminoalkyl, dialkylaminoalkoxy, —OH, acyloxy, free or esterified carboxy, —CN, —$CF_3$, phenyl, furyl, thienyl, benzyl, X is selected from the group consisting of —$CH_2$—, —$CH_2O$—, phenylene and phenylenoxy linked to the C ring through a carbon atom, Y is selected from the group consisting of a simple bond and saturated and unsaturated aliphatic of 1 to 18 carbon atoms optionally interrupted with at least one member of the group consisting of phenylene, —O— and optionally oxidized —S— and optionally terminated with phenylene, Z is a simple bond or —$CH_2$—O— linked to Y by a carbon atom, $R_A$ and $R'_A$ being individually selected from the group consisting of hydrogen and alkyl of 1 to 8 carbon atoms optionally substituted with at least one member of the group consisting of aryl, alkylamino, dialkylamino, —OH, halogen and esterified carboxyl with the proviso 1) that both of $R_A$ and $R'_A$ are not hydrogen and 2) when Z and Y are both simple bonds, X is not —$CH_2$— or —$CH_2$—O—.

2. A compound of claim 1 wherein Z is a simple bond.

3. A compound of claim 1 wherein $R_{17}$ is —OH.

4. A compound of claim 1 wherein $R_{17}'$ is hydrogen or ethynyl or propynyl.

5. A compound of claim 1 wherein X is —$CH_2$— and Y is linear alkylene of 5 to 10 carbon atoms optionally interrupted by —O—.

6. A compound of claim 1 wherein X is phenylene and Y is an aliphatic linear chain of 3 to 10 carbon atoms optionally interrupted by —O—.

7. A compound of claim 1 wherein X is phenylenoxy and Y is a linear alkylene of 3 to 10 carbon atoms optionally interrupted by —O— or —S—.

8. A compound of claim 1 wherein $R_A$ and $R_A'$ are both methyl or $R_A$ is methyl and $R_A'$ is selected from the group consisting of isopropyl, dimethylaminoethyl, benzyl and heptafluorobutyl or $R_A'$ is butyl and $R_A$ is hydrogen or methyl.

9. A antiestrogenic composition comprising an antiestrogenically effective amount of at least one compound of claim 1 and an inert pharmaceutical carrier.

10. A method of inducing hormonal activity in warm-blooded animals comprising administering to warm-blooded animals an antiestrogenically effective amount of at least one compound of claim 1.

11. A compound of claim 1 selected from the group consisting of N-butyl-4-(3,17β-dihydroxy-$\Delta^{1,3,5(10)}$-estratrien-11β-yl)-N-methyl-benzene octanamide; 3,17β-dihydroxy-N-methyl-N-isopropyl-$\Delta^{1,3,5(10)}$-estratrien-11β-yl-undecananide; N-butyl-N-methyl-3,17β-dihydroxy-19-nor-17α-$\Delta^{1,3,5,(10)}$-pregnatrien-20-yne-11β-yl-undecanamide; N-methyl-N-isopropyl-3,17β-dihydroxy-19-nor-17α-$\Delta^{1,3,5,(10)}$-pregnatrien-20-yne-11β-yl-undecanamide; [(8-1 (3,17β-dihydroxy-$\Delta^{1,3,5(10)}$estratrien-11β-yl)-octyl)-oxy]-N-methyl-N-isopropylacetamide; N-butyl-8-[4-(3,17β-dihydroxy-$\Delta^{1,3,5(10)}$-estratrien-11β-yl)-phenoxy]-N-methyl octanamide; N-butyl-[5-[4-(3,17β-dihydroxy-$\Delta^{1,3,5(10)}$-estratrien-11β-yl)-phenoxy]-pentyloxy]-N-methylacetamide; 2-[[7-[4-(3,17β-dihydroxy-$\Delta^{1,3,5(10)}$-estratrien-11β-yl)-phenyl]-6-heptylyl]-oxy]-N-butyl-N-methyl acetamide; 3,17β-dihydroxy-N-(2,2,3,3,4,4,4-heptafluorobutyl)-N-methyl-$\Delta^{1,3,5(10)}$-estratrien-11β-yl undecanamide and 8-[4-(3,17β-dihydroxy-$\Delta^{1,3,5(10)}$-estratrien-11β-yl)-phenyl]-N-butyl-N-methyl octynamide.

* * * * *